United States Patent [19]
Solomon et al.

[11] Patent Number: 5,939,431
[45] Date of Patent: Aug. 17, 1999

[54] NAPHTHYRIDINES WHICH AFFECT IL-4 AND G-CSF

[75] Inventors: Daniel M. Solomon, Edison; Michael J. Grace, Hamiltown; Jay S. Fine, Bloomfield; Loretta A. Bober, Linden; Margaret H. Sherlock, Bloomfield, all of N.J.

[73] Assignee: Schering Corporation, Kenilworth, N.J.

[21] Appl. No.: 08/878,860

[22] Filed: Jun. 19, 1997

Related U.S. Application Data

[60] Provisional application No. 60/022,173, Jun. 20, 1996.

[51] Int. Cl.$^6$ ............... A61K 31/435; C07D 471/04
[52] U.S. Cl. ............... 514/300; 546/122; 546/143
[58] Field of Search ............... 546/143, 122; 514/300, 310

[56] References Cited

U.S. PATENT DOCUMENTS

| | | | |
|---|---|---|---|
| 4,694,000 | 9/1987 | Timmerman et al. | 514/187 |
| 4,942,163 | 7/1990 | Behrens | 514/254 |

FOREIGN PATENT DOCUMENTS

| | | |
|---|---|---|
| 2550575 | 5/1977 | Germany. |
| 1545767 | 5/1979 | United Kingdom. |

OTHER PUBLICATIONS

Oster et al, *Blood*, 73 (1989), pp. 64–67.
Hestdal, et al, *J. Immunol.*, 147 (1991), pp. 22–28.
Springer et al, *Euro. J. Immunol.*, 9 (1979), pp. 301–306.
Demetri et al, *Blood*, 78 (1991), pp. 2791–2808.
"FICOLL–PAQUE for in vitro isolation of lymphocytes", Pharmacia booklet.
de Zwart et al, *J. Med. Chem.*, 32 (1989), pp. 487–493.
de Zwart et al, *J. Med. Chem.*, 31 (1988), pp. 716–722.
Chemical Abstracts, 61, 7 (1964), abstract 8285c.

*Primary Examiner*—Bernard Dentz
*Attorney, Agent, or Firm*—Palaiyur S. Kalyanaraman; Anita W. Magatti

[57] ABSTRACT

Compounds of formula

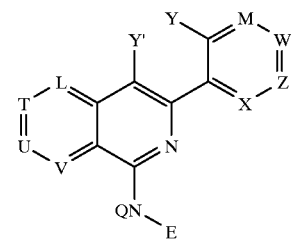

I or pharmaceutically acceptable salts thereof, wherein E, Q, T, U, V, L, Z, X, W, M, Y and Y' are as set forth herein, are described. These compounds are useful as agents in the treatment of allergy, inflammation, autoimmune diseases, B-cell lymphomas, tumors, and the after effects of bone marrow transplantation.

16 Claims, No Drawings

NAPHTHYRIDINES WHICH AFFECT IL-4 AND G-CSF

This application claims priority from Verified Provisional Application No. 60/022,173 filed Jun. 20, 1996.

SUMMARY OF THE INVENTION

The invention relates to compounds of the formula

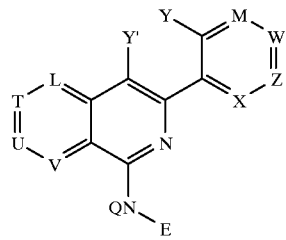

I wherein E is

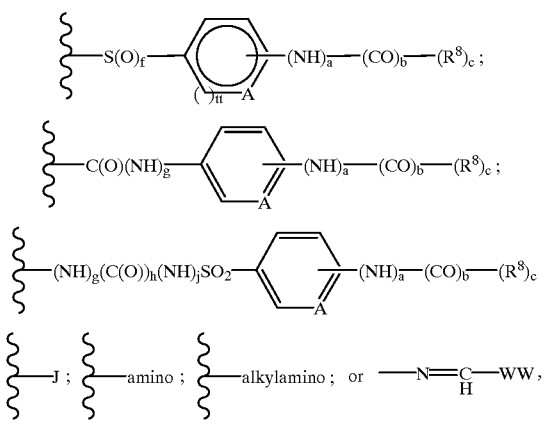

wherein WW is aryl or heteroaryl; and
wherein A is CH, S, N or $^{N \to O}$ wherein L, M, X, Z, W, T, U, and V are each independently CH, N or $^{N \to O}$, with the proviso that only one of L, T, U, and V can be N or $^{N \to O}$; and with the further proviso that only one of M, X, Z, and W, can be N or $^{N \to O}$;

Y is H or —CH$_3$;

Y' is H, lower alkyl, phenyl, phenyl-lower alkyl;

Q is H, lower alkyl O(O)CCH$_2$—, lower alkyl, or lower alkyl (O)C—, a, b, c, g, h, and j is each independently 0 or 1;

f is 1 or 2;

n is 1 to 6;

tt is 0 or 1;

$R^8$ is H, OH, halo when a and b are both 0, $C_1$–$C_{10}$ alkyl, $C_1$–$C_6$ alkoxy, —OCH$_2$Ph, —CH$_2$Ph, —CH$_2$CH$_2$Ph, cyclohexyl, CH$_2$C(O)OC$_2$H$_5$; —O(CH$_2$)$_2$O—(CH$_2$)$_2$OCH$_3$, —CO$_2$H when a and b are both 0; NHCH$_2$Ph, NH(CO)CH$_3$, —NH$_2$, —OH when a is 0, aryl, —CH$_2$C(O)OH, —CH$_2$C(O)ONa, phenyl, substituted phenyl,

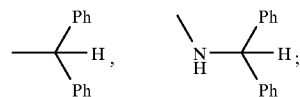

or —SO$_2$NH$_2$ when a and b are both 0;

J is SO$_2$CH$_2$CONH(CH$_2$)$_2$SO$_3^-$Na$^+$, —SO$_2$CH$_2$Ph, —SO$_2$CH$_2$C(O)NHOH, —SO$_2$CH$_2$CO$_2$H, —SO$_2$CH$_2$CO$_2$Na, —SO$_2$CH$_2$CO$_2$(CH$_2$)$_2$O(CH$_2$)$_2$CH$_3$, —SO$_2$(CH$_2$)$_2$CH$_3$, —S(O)$_2$CH$_2$CO$_2$CH$_3$, —S(O)$_2$CH$_2$C(O)NHCH$_2$C(O)OH, SO$_2$CH$_3$, —S(O)$_2$CH$_2$C(O)NHCH$_2$C(O)Na, —S(O)$_2$CH$_2$C(O)NH(CH$_2$)$_2$SO$_3$Na, —S(O)$_2$CH$_2$CO$_2$Na, —SO$_2$CH$_2$CH$_2$OH, —SO$_2$(CH$_2$)$_n$C(O)-amino acid, —SO$_2$(CH$_2$)$_n$C(O)-protected amino acid; —SO$_2$(CH$_2$)$_n$ X'; wherein X' is an ester or an amide and n is 1 to 6;

or a pharmaceutically acceptable salt thereof.

Preferred among these are compounds of the formula I

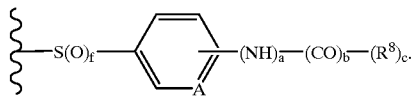

wherein E is

Also preferred among these are compounds of the formula I wherein E is

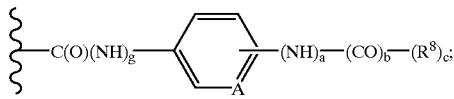

Also preferred among these are compounds of the formula I wherein E is

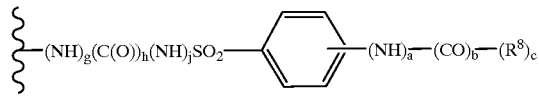

Also preferred among these are compounds of the formula I wherein E is

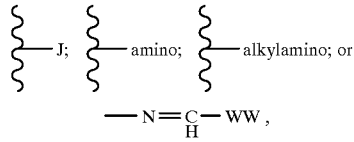

wherein WW is aryl or heteroaryl.

Also preferred are compounds of formula I wherein Z is

Also preferred are compounds of formula I'

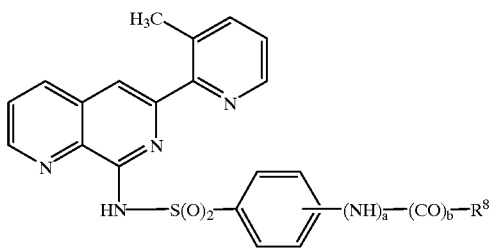

wherein a is 0 or 1;
b is 0 or 1; and
R$^8$ is C$_1$–C$_6$ alkyl, C$_1$–C$_6$ alkoxy, —OCH$_2$Ph, or —CH$_2$Ph,
or a pharmaceutically acceptable salt thereof.

Also preferred among these are compounds of the formula I' wherein a is 1, b is 1, and R$^8$ is —CH$_3$.

Also preferred among these are compounds of the formula I' wherein R$^8$ is —C$_1$–C$_6$ alkyl.

Also preferred among these are compounds of the formula I' wherein R$^8$ is —OCH$_2$Ph.

Also preferred among these are compounds of the formula I' wherein R$^8$ is —CH$_2$Ph.

Exemplary of compounds of the invention are:

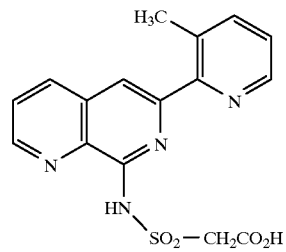

or the sodium salt of the carboxylic acid;

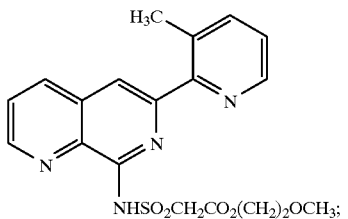

NHSO$_2$CH$_2$CO$_2$(CH$_2$)$_2$OCH$_3$;

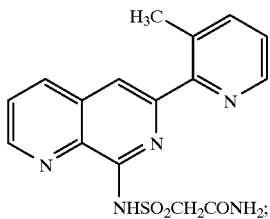

NHSO$_2$CH$_2$CONH$_2$;

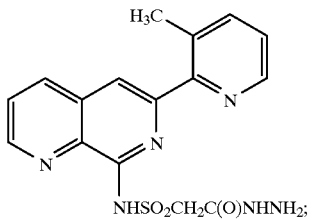

NHSO$_2$CH$_2$C(O)NHNH$_2$;

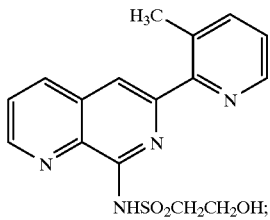

NHSO$_2$CH$_2$CH$_2$OH;

NHSO$_2$CH$_2$C(O)NH(CH$_2$)$_2$N(CH$_3$)$_2$;

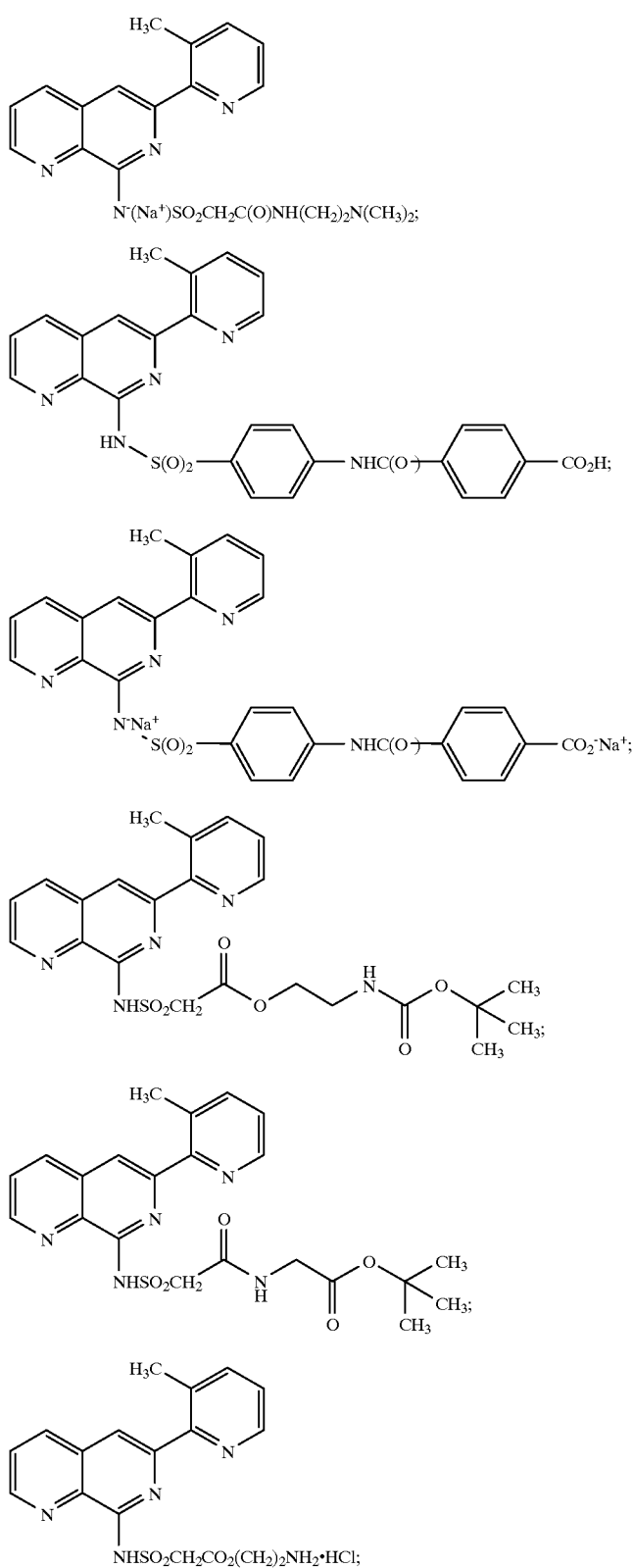

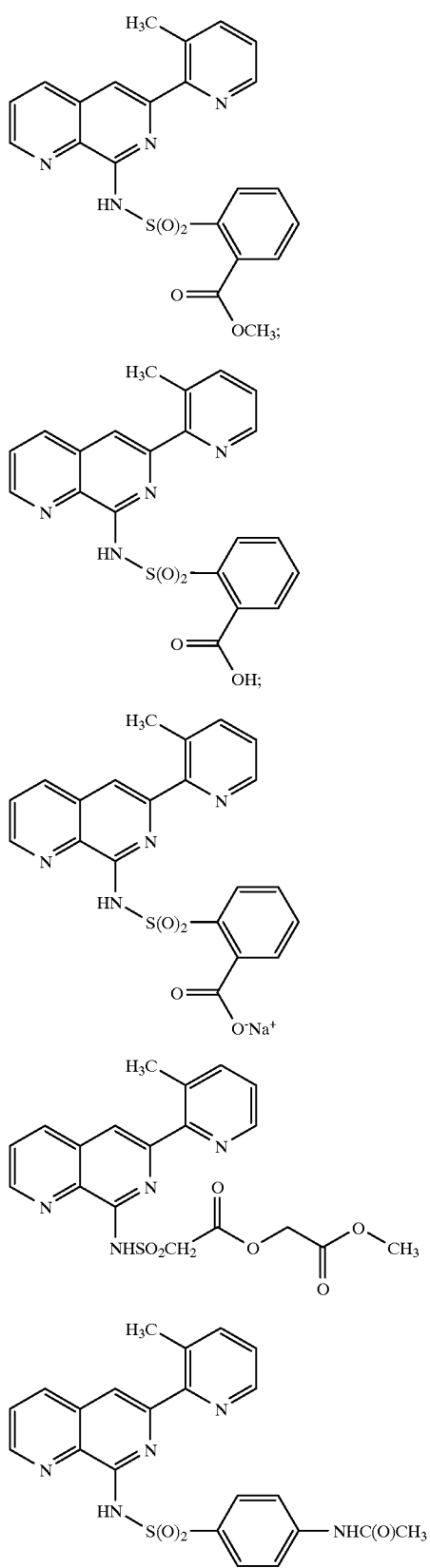

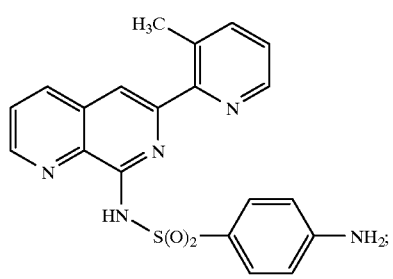
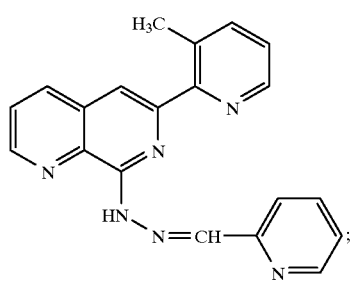
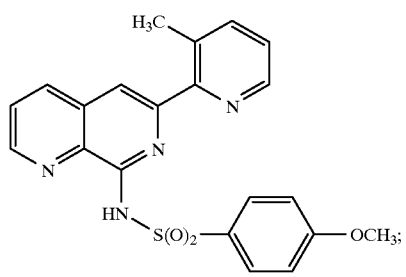
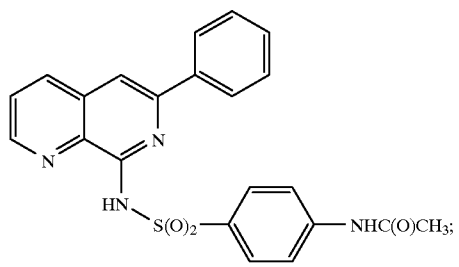
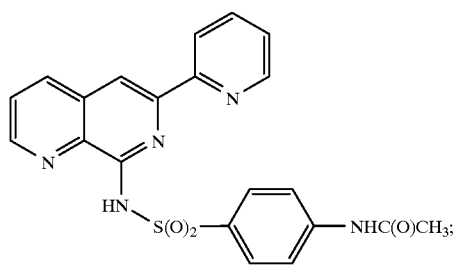
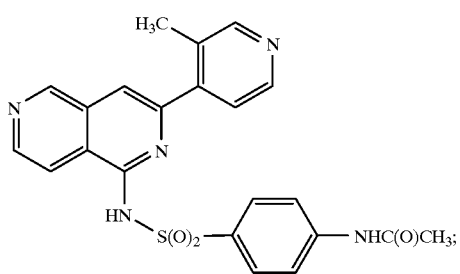

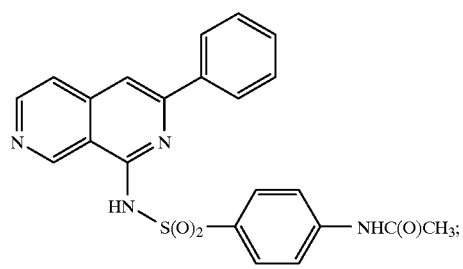
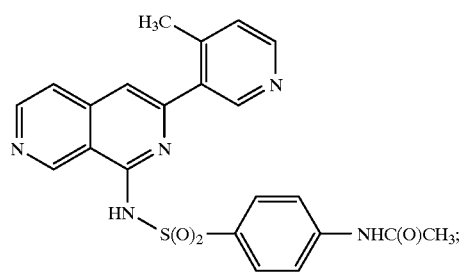
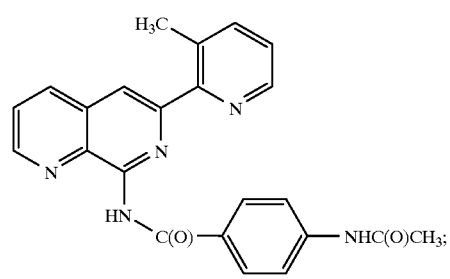
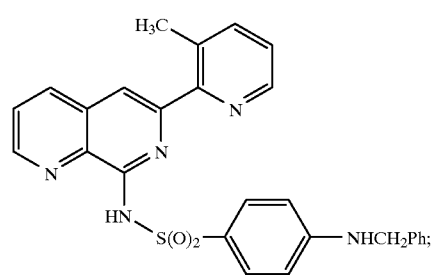
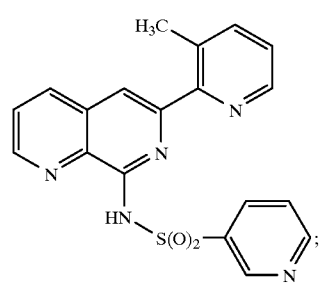
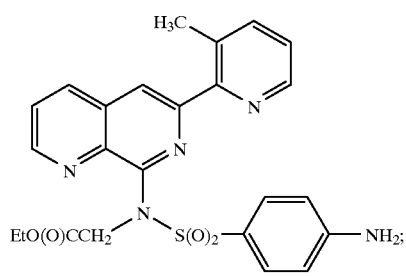

-continued
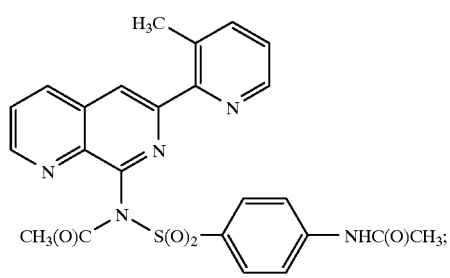
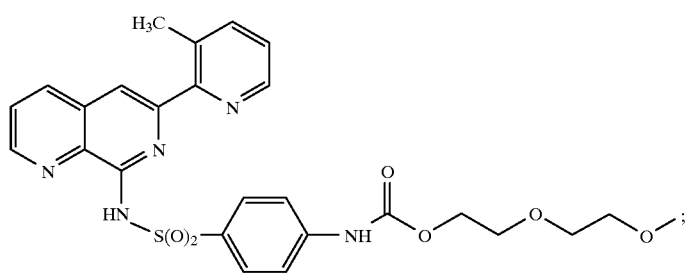
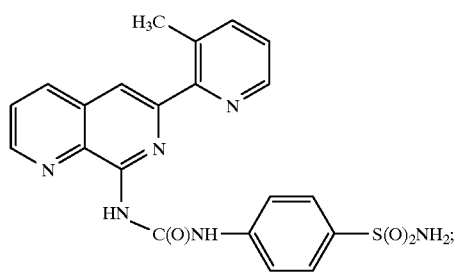
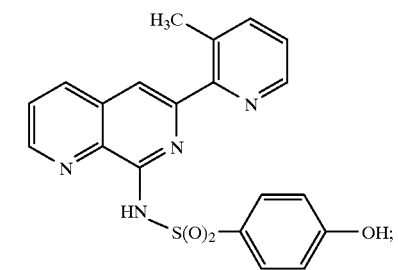
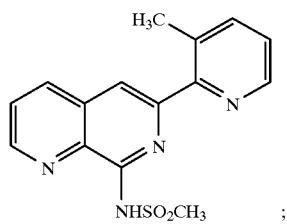
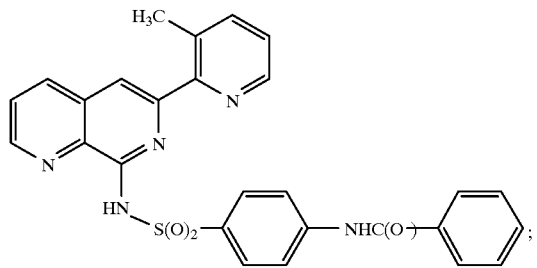

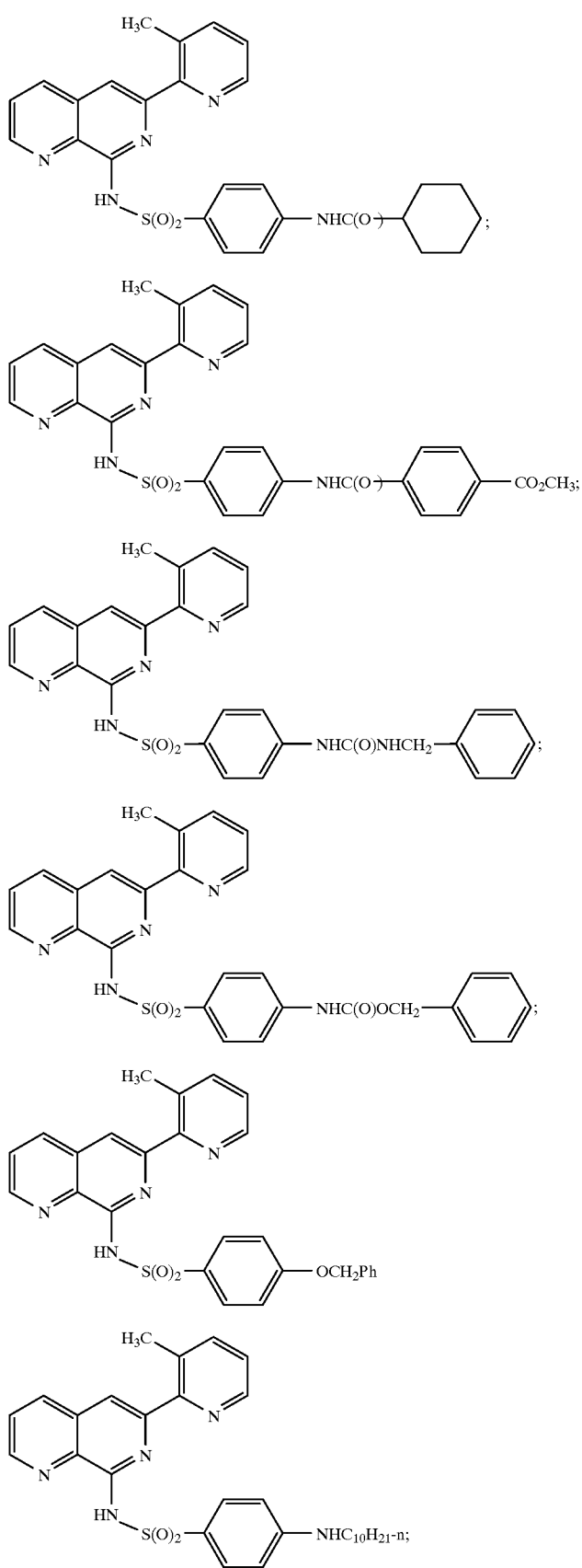

-continued
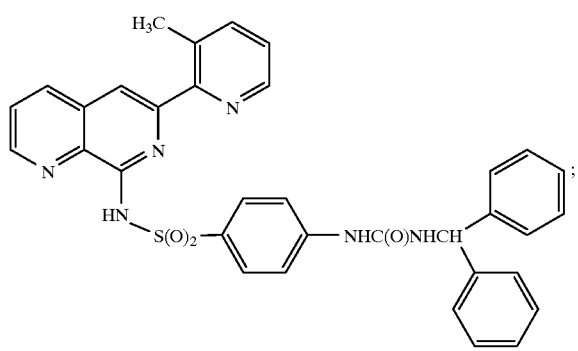
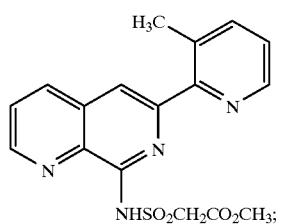
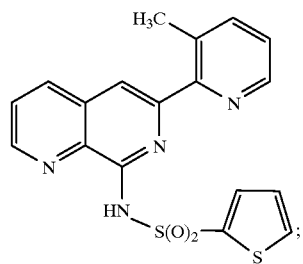
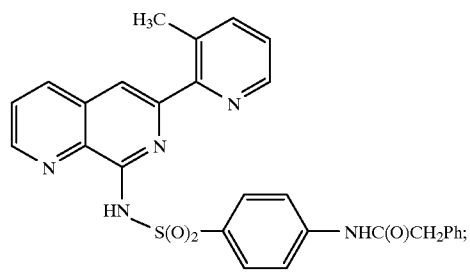
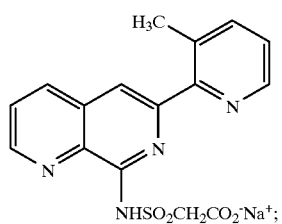
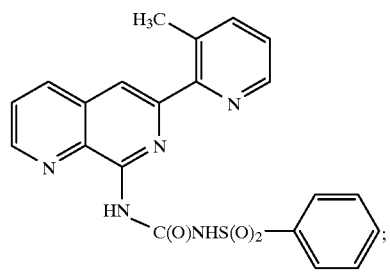

-continued
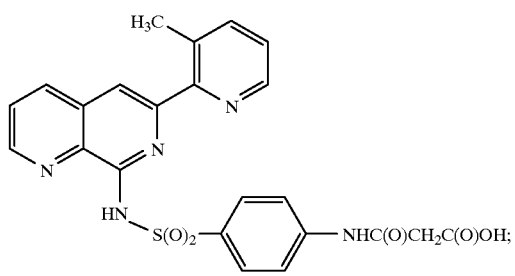
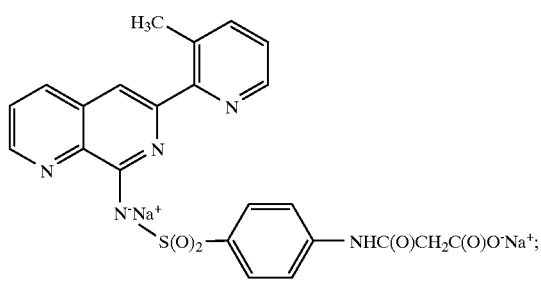
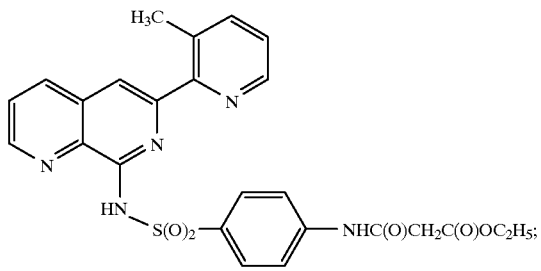
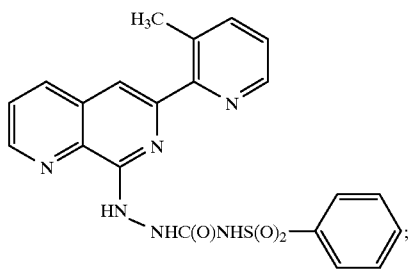
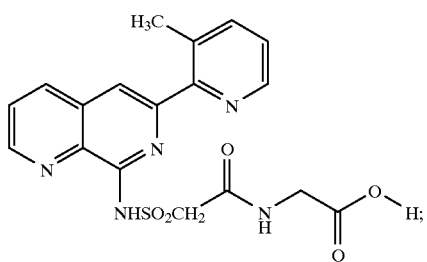
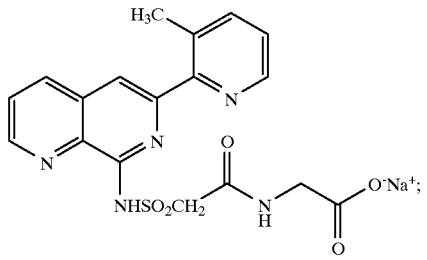

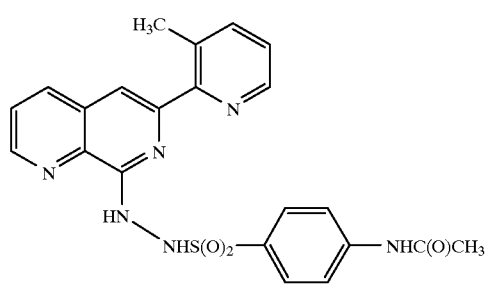
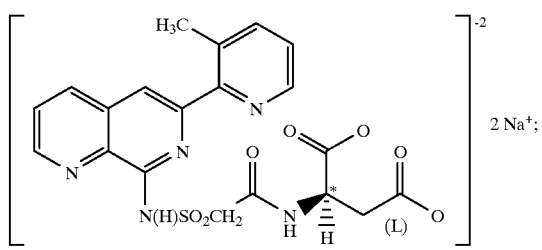
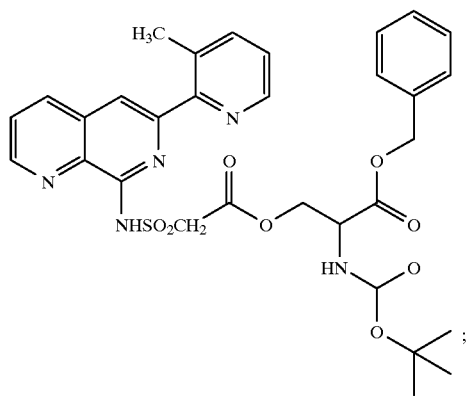
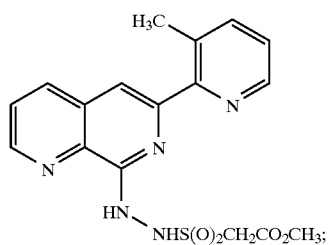
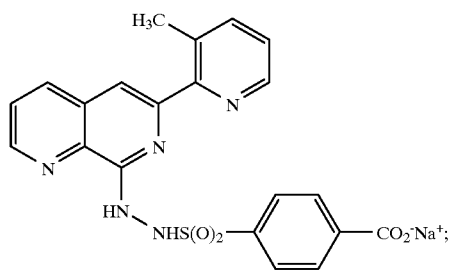

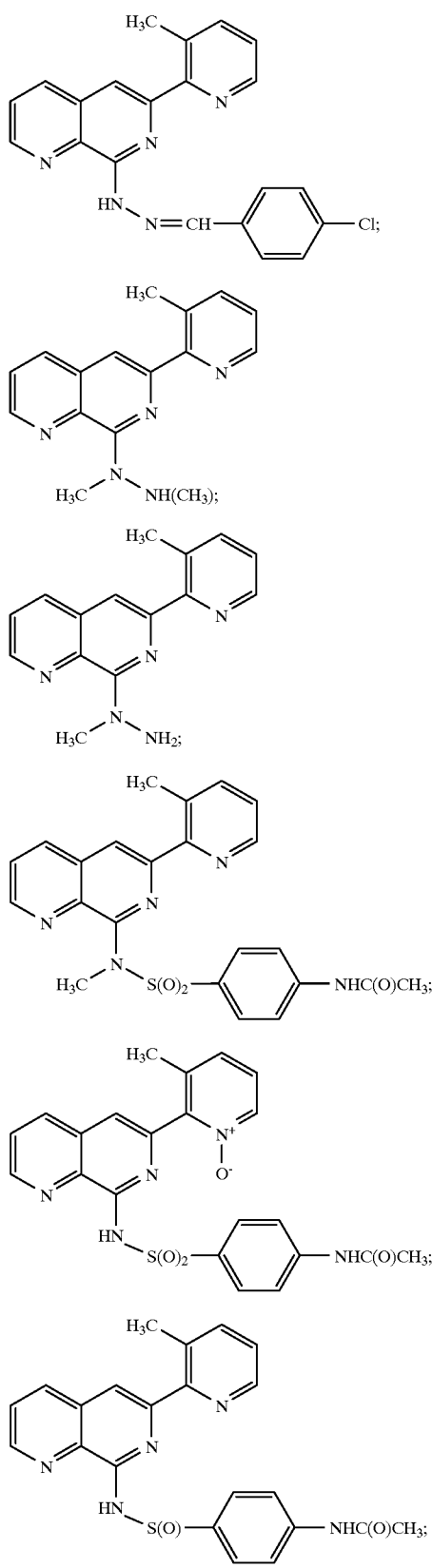

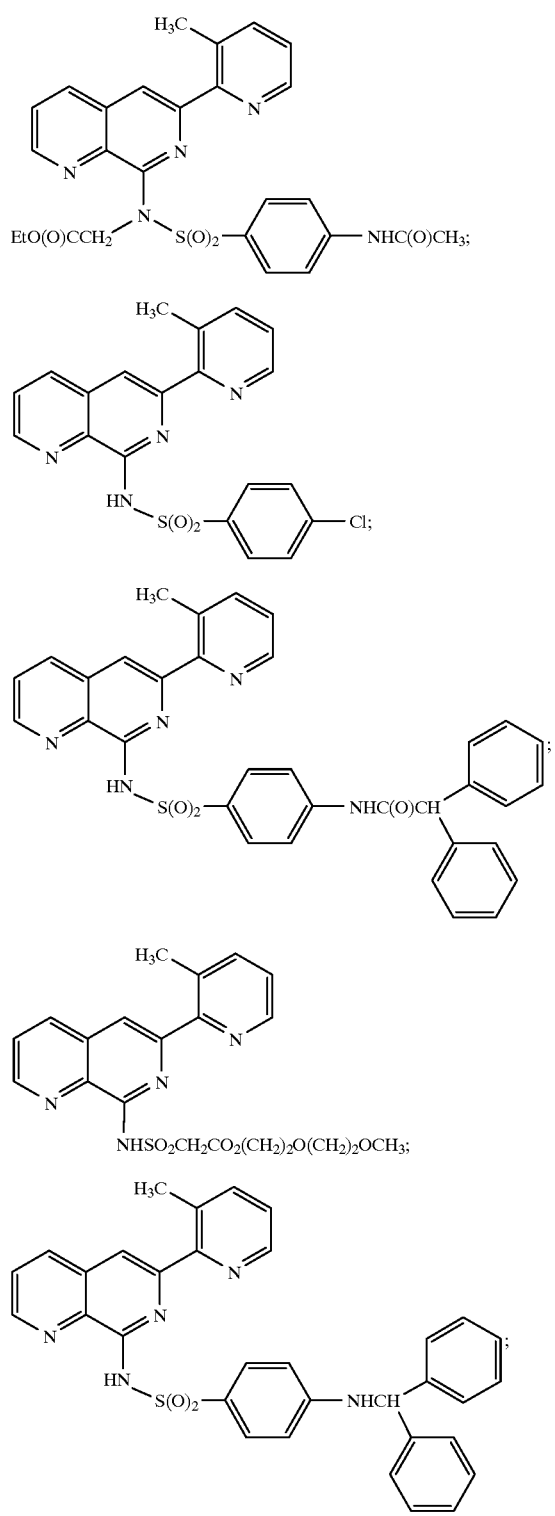

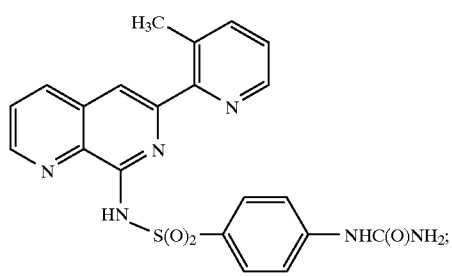
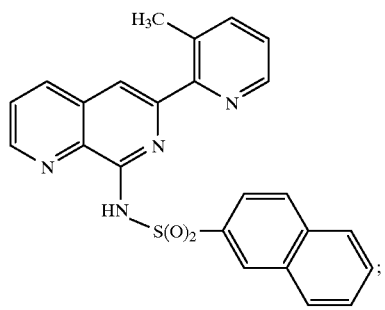
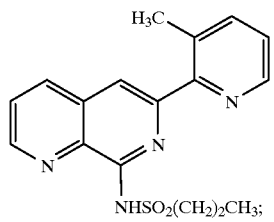
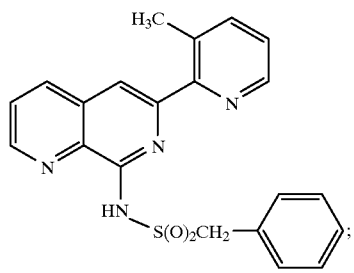
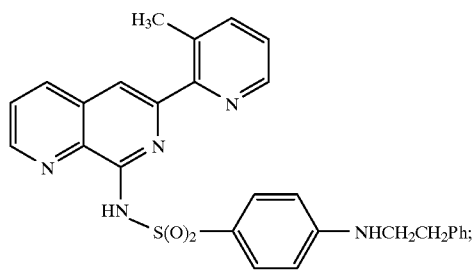
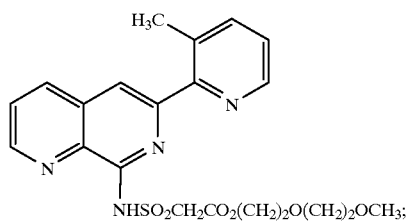

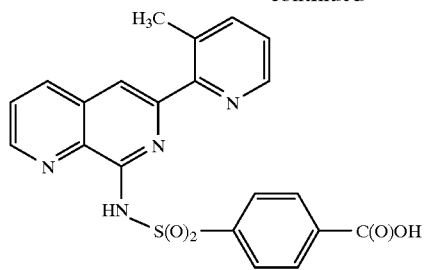
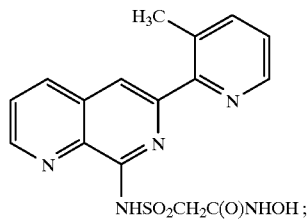
NHSO₂CH₂C(O)NHOH;
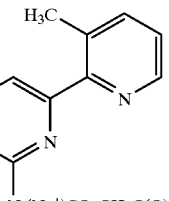
N⁻(Na⁺)SO₂CH₂C(O)NHO⁻Na⁺;
and
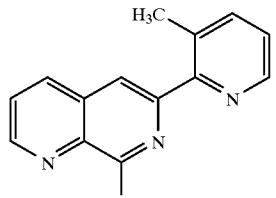
NHSO₂CH₂CONH(CH₂)₂SO₃⁻Na⁺.
Other compounds of the invention are:
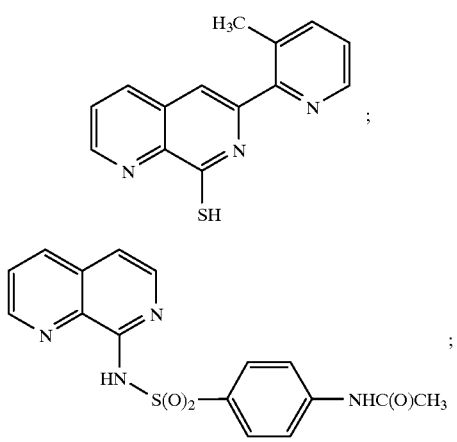
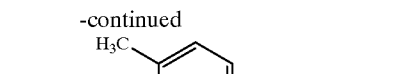
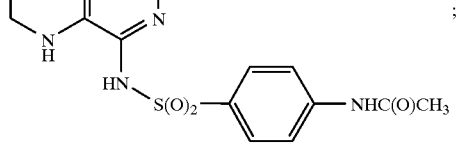
; and
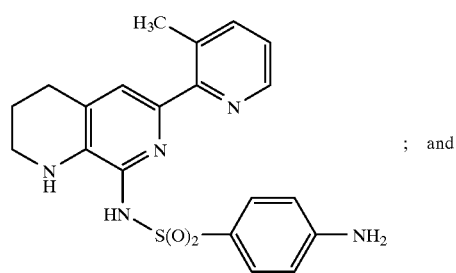

-continued

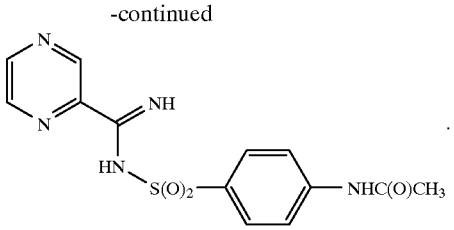

A most preferred compound of the invention is

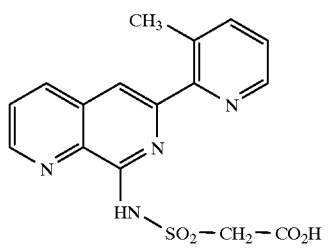

or a pharmaceutically acceptable salt thereof.

Another most preferred compound of the invention is

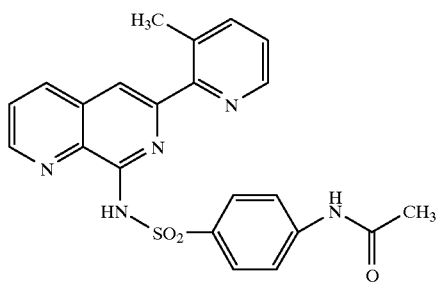

Another most preferred compound of the invention is

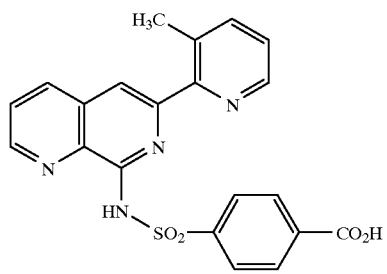

or the sodium salt of the carboxylic acid.

Compounds of formula I of the invention are antagonists of IL-4 and as such are useful as agents in the treatment of allergy, inflammation, autoimmune diseases, and certain B-cell lymphomas.

Compounds of formula I and other compounds of the invention are also stimulators of granulocyte-colony stimulating factor (G-CSF) production from human peripheral blood mononuclear cells (PBMNC) and monocyte/macrophages. As such, these compounds stimulate neutrophil granulopoiesis and are therefore useful as agents in treating cancer patients and in treating patients who have had bone marrow transplantation.

The invention also relates to a pharmaceutical composition comprising a therapeutically effective amount of a compound of formula I or other compounds of the invention in combination with a pharmaceutically acceptable carrier.

The invention also relates to a method for treating allergy, inflammation, autoimmune diseases, certain B-cell lymphomas, tumors, and the after-effects of bone marrow transplantation which comprises administering to a mammal in need of such treatment, an anti-allergy, anti-inflammation, anti-autoimmune disease; anti-B-cell lymphoma anti-tumor or anti-after effects of bone marrow transplantation effective amount of a compound of formula I or other compounds of the invention, for such purpose.

DETAILED DESCRIPTION OF THE INVENTION

Asymmetric centers exist in certain compounds of formula I of the invention. Accordingly, compounds of formula I include stereoisomers.

All such isomeric forms and mixtures thereof are within the scope of the present invention. Unless otherwise indicated, the methods of preparation disclosed herein may result in product distributions which include all possible structural isomers, although it is understood that physiological response may vary according to stereochemical structure. The isomers may be separated by conventional means such as fractional crystallization, preparative plate or column chromatography on silica, alumina, or reversed phase supports or HPLC (high performance liquid chromatography).

Enantiomers may be separated, where appropriate, by derivatization or salt formation with an optically pure reagent, followed by crystallization, for example, or other methods known in the art such as high performance liquid chromatography on a chiral support.

The compounds of formula I can exist in unsolvated as well as solvated forms, including hydrated forms, e.g. the hemihydrate. In general, the solvated forms, with pharmaceutically acceptable solvents such as water, ethanol, and the like are equivalent to the unsolvated forms for the purposes of the invention.

"Pharmaceutically acceptable salt" of a compound of the invention means nontoxic acid addition salts formed by adding to a suitable compound of the invention about a stoichiometric amount of a mineral acid, such as HCl, HBr, $H_2SO_4$ or $H_3PO_4$ or of an organic acid such as acetic, propionic, valeric, oleic, palmitic, stearic, lauric, benzoic, lactic, para-toluenesulfonic, methanesulfonic, citric, maleic, fumaric, succinic and the like, respectively.

Salts of carboxylic acids may also be formed. An example of such a salt is the sodium salt. Salts of other acidic centers may also be formed. For example, a salt of a carboxylic acid and also an NH is seen in the compound just below.

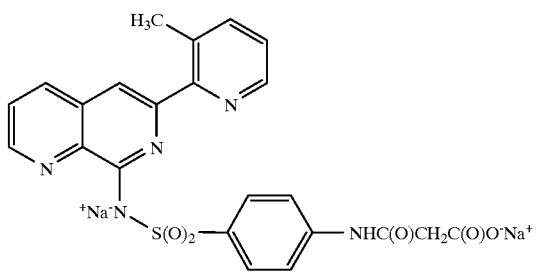

When utilized herein and in the appended claims, the following terms have the following meanings, unless otherwise specified:

"alkyl"—(including the alkyl portions of alkoxy, etc) represents a straight or branched, saturated hydrocarbon chain having from 1 to 20 carbon atoms. The number of carbon atoms may be specified. For example, "$C_1$–$C_6$ alkyl" represents a straight or branched, saturated hydrocarbon having from 1 to 6 carbon atoms. "Lower alkyl" represents a straight or branched, saturated hydrocarbon chain having from 1 to 6 carbon atoms.

"alkoxy" represents—O-alkyl, where alkyl is as described above.

"alkylamino"—represents an amine wherein one or two of the hydrogens of the amine are repaced by a a straight or branched, saturated hydrocarbon chain having from 1 to 20 carbon atoms.

"cycloalkyl"—(including the cycloalkyl portions of cycloalkylalkoxy, etc.) represents a cycloalkyl having from 3 to 8 carbon atoms. The number of carbon atoms may be designated. For example, "$C_3$–$C_6$ cycloalkyl" represents a cycloalkyl having from 3 to 6 carbon atoms.

"aryl"—represents a mono or bi-cyclic aromatic system. Examples of preferred aryl groups include those having from 6 to 10 carbon atoms. Representative examples include phenyl, 1-naphthyl, and 2-naphthyl. The aryl group may contain additional substituents selected from the group consisting of: halogen atoms (e.g., Cl, Br, F, and/or I), —OH, $CO_2H$, $CF_3$, alkoxy, alkyl, amino, —COO-lower alkyl, —COO-lower alkyl-phenyl, —$CONH_2$, —CONH-lower alkyl, —CON(lower alkyl)$_2$, and —CONH-lower alkyl-phenyl.

"arylalkyl"—represents an alkyl group as defined above in which an aryl group as defined above replaces one of the alkyl hydrogen atoms. Representative examples include —$CH_2$phenyl, —$CH_2CH_2$phenyl, 4-hdyroxybenzyl, 4-t-butyldimethylsilyloxybenzyl, and the like. "Aryl-lower alkyl" represents a lower alkyl group as defined above in which an aryl group as defined above replaces one of the lower alkyl hydrogen atoms.

As used herein "dec" means decomposition.

As used herein "h" means hours.

"Heteroaryl" (including the heteroaryl portion of heteroarylmethyl)—represents aromatic systems having at least one O, S and/or N heteroatom in the ring structure. Examples of preferred heteroaryl groups include those containing from 3 to 9 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1, 2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2- or 3-pyrrolyl, 2- or 3-N-methylpyrrolyl, and the like. Hetero aryl groups includes N-oxides of pyridyl.

"Halogen" or "halo" means chloro, fluoro, bromo, and iodo.

"acyl" (including the acyl portion of arylacyl, etc.) means a CO-alkyl, a CO-substituted alkyl, a CO-aryl or a CO-aralkyl wherein alkyl, substituted alkyl, aryl and aralkyl are as defined herein.

"Substituted" means substituted by 1 to 3 substituents independently selected from the group consisting of H, $C_1$–$C_6$ alkyl, —$CO_2H$, an ester, an amide, $CF_3$, OH, $OC_1$–$C_6$ alkyl, —$NH_2$, Cl, Br, I, F, —NH-lower alkyl, —N(lower alkyl)$_2$;

The term "amino acid" denotes the following natural amino acids; glycine and the following acids which have an L-configuration: valine, leucine, isoleucine, serine, aspartic acid, asparagine, glutamic acid, histidine, alanine, proline, phenylalanine, tryptophan, methionine, threonine, cysteine, tyrosine, glutamine, lysine and arginine which are also referred to respectively by the following abbreviations:

Gly, Val, Leu, Ile, Ser, Asp, Asn, Glu, His, Ala, Pro, Phe, Trp, Met, Thr, Cys, Tyr, Gln, Lys and Arg.

In general, amino acids are bound to the rest of the molecule via the alpha-amino terminus.

Amino acids having side-chain hydroxyl, sulfhydryl, or amino groups may be bound to the rest of the molecule via either the alpha-amino group or the side-chain heteroatoms.

The term "amino acid" also denotes corresponding amino acids having the D-configuration.

The term "protected amino acid" means an amino acid wherein the amino and/or carboxy termini are protected. Amino acids having side-chain hydroxyl, sulfhydryl, or amino groups may be bound to the rest of the molecule via either the alpha-amino group or the side-chain heteroatoms. When the protected amino acids are bound through the side-chain heteroatoms, the amino and carboxy termini may be protected by protecting groups known in the art. For example, compounds of the invention may include serine or threonine derivatives wherein the amino acid may be bound to the rest of the molecule via the side-chain hydroxyl group, while the alpha-amino group is protected by a tert-butyloxycarbonyl moiety and the carboxy goup is protected as the benzyl ester. In the case of protected amino acids lacking side-chain heteroatoms, these protected amino acids are bound to the rest of the molecule via the alpha-amino terminus, while the carboxy terminus is protected by a known protecting group.

Unless otherwise designated the term "ester" denotes (CO)$OR^\alpha$, wherein $R^\alpha$ is lower alkyl, —$(CH_2)_m$—$G_a$—$R^9$, —$(CH_2)_{m'}$COO-lower alkyl, or —$(CH_2)_m NR^{9'}$COO-lower alkyl;

$G_a$ is O or $NR^{9'}$;

m is 0 or 2 to 6;

m' is 1 to 6 a is 0 or 1;

$R^9$ H, lower alkyl, aryl or acyl, aryl lower alkyl; and $R^{9'}$ is H, lower alkyl, aryl or aryl lower alkyl.

Unless otherwise designated the term "amide" denotes —$CONR^\beta R^\gamma$, wherein $R^\beta$ is H or —$(CH_2)_m$—$G_a$—$R^9$; and $R^\gamma$ is H, lower alkyl, or $NHR^{9'}$, —$(CH_2)_m$COO-lower alkyl, or—$(CH_2)_m$NHCOO-lower alkyl.

Biological activity of the compounds of the invention was demonstrated by the assays set forth below.

Amino acids having side-chain, sulfhydryl, or amino groups may be bound to the rest of the molecule via either the alpha-amino group or the side-chain heteroatoms; in the latter case, the amino and carboxy termini may be protected by protecting groups known in the art. For example, compounds of the invention may include serine or threonine derivatives wherein the amino acid may be bound to the rest of the molecule via the side-chain hydroxyl group, while the alpha-amino group is protected by a tert-butyloxycarbonyl moiety and the carboxy group is protected as the benzyl ester.

Assay to Test for IL-4 Antagonism

Induction of a B Cell Differentiation Marker, CD 23, on Jijoye Cells

Jijoye cells ATCC) were grown routinely in RPMI containing 15% horse serum and 5% fetal bovine serum (FBS). Cells were split every third day.

For assay, Jijoye cells were placed in exponential growth 24 hours prior to initiation; 5×10$^5$ cells/ml were suspended in media with serial dilutions of test compound to a volume of 1 ml. After 24 hours, fresh media (with IL-4) was added 1:1 to a total volume of 2 ml. The total incubation time for the assay was 48 hours at 37° C. and 5% $CO_2$. At termination of the experiment, the cells were removed and washed twice in RPMI 1640 containing 5% FBS. To the pellet a 1:4 dilution of MAb 25 (anti-CD23) in RPMI 5% was added and incubated for 30 minutes at 4° C. The anti-CD23 monoclonal antibody MAb 25 was provided by Unicet. The cells were washed twice in PBS containing 1% FBS, centrifuged to a pellet, and resuspended in 100 μl of a 1:10 dilution of FITC-conjugated F(ab)$_2$ goat anti-mouse IgG. After a 30 minute incubation at 4° C., the cells were washed twice in PBS and then counted using a Becton-Dickinson FACscan Cytofluorometer.

As used herein compound AA denotes the compound of the structural formula 14988:

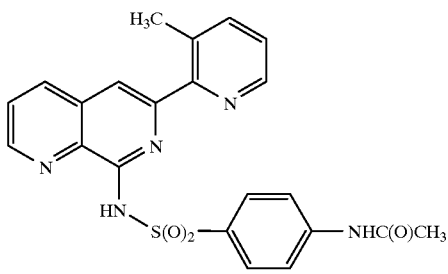

In Vitro Enhancement of G-CSF Production

In order to determine the effect of compound AA on human G-CSF production, human peripheral blood mononuclear cells (PBMNC's) were prepared (as described in Ficoll-Paque: For in vitro *isolation of lymphocytes* (booklet) 1983 Pharmacia, Uppsala Sweden; which is hereby incorporated by reference) and cultured as described (in Oster et al, 1989 Blood 73:64. which is hereby incorporated by reference) with 5 μg/ml phytohemagglutin (PHA) in the presence of varying concentrations of compound AA or vehicle (0.1% dimethylsulfoxide, DMSO). After 40 hours, culture supernatant was collected and cytokine levels measured by ELISA (R&D Systems, Minneapolis Minn.). Alternatively mRNA was prepared by standard protocols from these cells after 24 hour incubation, reverse-transcribed and subjected to polymerase chain reaction (PCR)

Addition of compound AA resulted in a 4–5-fold increase in G-CSF levels, with an effective concentrations ($EC_{50}$) of 15 μM. This effect was specific for G-CSF, since no change in the production of TNFα, TNFβ, IL-1α, IL-1β, IL-3, IL-6, IL-8, or GM-CSF was observed. Similar results were obtained with peripheral blood elutriated monocytes (prepared as described in Wahl L. M. and P.D. Smith, in *Current Protocols in Immunology*, J. Coligan et al Eds. 1991 Chapter 7, Wiley & Sons, New York which is hereby incorporated by reference) incubated with lipopolysaccharide (LPS).

Steady-state G-CSF mRNA levels were also increased in cultures of PHA-stimulated PBMNC's and LPS-stimulated monocytes, indicating modulation of transcriptional or post-transcriptional activation of the G-CSF gene by compound AA.

These data indicate that compound AA specifically enhances G-CSF production by both PBMNC's and monocytes, suggesting that this compound may possess clinical utility in accelerating recovery from neutropenia due to chemo- or radio-therapy, or after bone marrow transplantation.

In Vivo Acceleration of Recovery from Neutropenia in Cyclophosphamide-treated Mice To test the activity of compound AA in enhancing peripheral neutrophil numbers and accelerating recovery of the neutrophil compartment, BALB/cJ mice were rendered neutropenic by treatment with a single sublethal dose of CY on day 0. Mice were then treated daily, starting on day 1, with 40 mg/kg compound AA or vehicle (carboxymethyl cellulose CMC) and sacrificed on days 3, 5, 6, 8 or 10 and granulocyte populations in peripheral blood and spleen analyzed by flow cytometry. Granulocytes were detected using the RB6-8C5 antibody, specific for granulocytes (see Hestdal et al 1991 *J. Immunol.* 147:22. which is hereby incorporated by reference) and the Mac-1 antibody, specific for myeloid cells (see Springer et al *JEur. J. Immunol.* 9: 301). At each time point, vehicle or compound AA -treated animals were compared to normal, age-matched control mice which did not receive CY. Compound AA administration accelerated granulocyte recovery in both blood and spleen, with a return to normal numbers by day 5 in blood and day 4 in spleen. These granulocytes were confirmed to be exclusively segmented neutrophils by cytological examination. Neutrophil recovery was delayed by 1–2 days in CY-dosed mice given vehicle, compared to compound AA-treated animals. No changes in percentage or number of monocytes were observed. No evidence of gross toxicity or abnormalities were a observed as well.

These data indicate that compound AA does in fact accelerate recovery from neutropenia in CY-treated mice, suggesting that it would have similar activity in neutropenic patients.

Measurement of Endogenous G-CSF in CY-dosed Mice Administered Compound AA

Acceleration of neutrophil recovery by compound AA may occur by stimulating neutrophil development at the level of the bone marrow (see Demetri et al 1991 *Blood* 78: 2791). To confirm that compound AA was acting in vivo by enhancing endogenous G-CSF production, bone marrow steady-state G-CSF mRNA levels were determined by PCR. Compound AA treatment enhanced G-CSF mRNA levels.

These data indicate that this compound enhances neutrophil recovery by its G-CSF stimulating activity.

Comparison of Compound AA with rhG-CSF

Exogeneous G-CSF administration is now standard therapy for patients undergoing a neutropenic episode. In order to compare compound AA treatment with G-CSF therapy in the CY model described above, we administered either compound AA or recombinant human G-CSF daily to mice made neutropenic with CY. Granulocyte levels in peripheral blood were determined on day 5. The ability of compound AA at 40 mg/kg to enhance peripheral blood neutrophil numbers was comparable to that of 250 mg/kgrhG-CSF and was greater than that observed in animals treated with 50–125 mg/kg rhG-CSF.

These data indicate that 40 mpk SCH compound AA is as or more efficaceous in restoring blood neutrophil levels in CY-treated mice than rhG-CSF.

The compounds of this invention can be administered in any number of conventional dosage forms, e.g., topical, oral, parenteral, rectal, transdermal, and the like. Oral or rectal dosage forms include capsules, tablets, pills, powders, cachets, and suppositories. Liquid oral dosage forms include solutions and suspensions. Parenteral preparations include sterile solutions and suspensions. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives, lubricants, etc. Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into the capsules along with a pharmaceutically acceptable carrier. The active compounds of this invention can be mixed with pharmaceutically acceptable excipients or be used in finely divided powder form without excipients for inclusion into the capsules. Similarly, cachets are included. Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical, dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents. Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

A composition of the invention comprises a therapeutically effective amount of a compound of the invention in combination with a pharmaceutically acceptable carrier material. The compounds of this invention may be administered by any conventional mode of administration by employing a therapeutically effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

By using the appropriate starting materials, and by following the methods described in the examples below, one skilled in the art can prepare all of the compounds set forth in formula I. The starting materials in the examples below are commercially available or are known or can be prepared by known methods.

EXAMPLES

Example 1

8-(p-Acetamidobenzenesulfonamido)-6-(3-methyl-2-pyridinyl)-1,7-naphthyridine also known as N-[4-[[[6-(3-Methyl-2-pyridinyl)-1,7-naphthyridin-8-yl]amino]sulfonyl]phenyl]acetamide

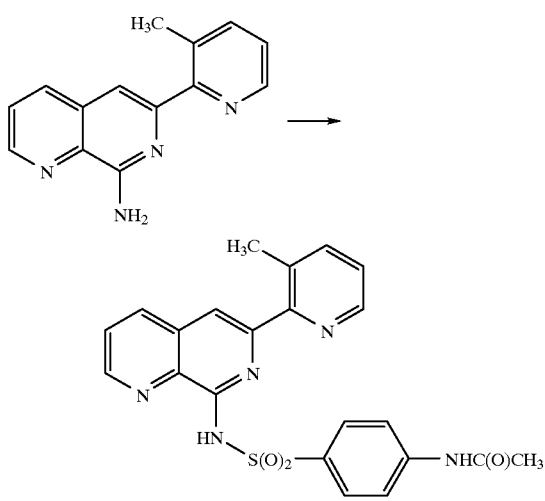

Reflux a stirred mixture of 8-amino-6-(3-methyl-2-pyridinyl)-1,7-naphthyridine (39.38 g, 0.167 mol), triethylamine (18.71 g, 0.185 mol), 4-N,N-dimethylaminopyridine (1.95 g, 0.016 mol) and N-acetylsulfanilyl chloride (42.89 g, 0.184 mol) in dry dichloromethane (1.1 L) for 55 hours, cool the reaction mixture to 10° C., filter the mixture, wash the solids with dichloromethane (150 mL) and vacuum dry. Crystallize from N,N-dimethylformamide the crude product thus obtained. Filter the crystallized product and triturate successively with diethyl ether, hot methanol, diethyl ether and dichloromethane to obtain the title compound as a 0.25 hydrate, $C_{19}H_{22}N_2O_5S \cdot 0.25\ H_2O$, mp 250–251.5° C. FABMS: MH$^+$ 434 (100%).

Example 1a
N-[4-[[(Iminopyrazinylmethyl)amino]sulfonyl]phenyl]acetamide

In a manner analogous to that described in Example 1, prepare starting with pyrazine-2-carboxamidine the title compound as a ⅙ hydrate, $C_{13}H_{13}N_5O_3S \cdot 0.167\ H_2O$, mp 270–274° C. FABMS: MH$^+$ 320 (100%).

Example 2
[[[6-(3-methyl-2-pyridinyl)-1,7-naphthyridin-8-yl]amino]sulfonyl]acetic acid, methyl ester Stir a solution containing 8-amino-6-(3-methyl-2-pyridinyl)-1,7-naphthyridine (630 mg, 2.67 mmol), triethylamine (0.45 mL, 3.20 mmol), 4-N,N-dimethylaminopyridine (13 mg) and 90% methyl (chlorosulfonyl acetate (0.61 mL, 3.20 mmol) in dry dichloromethane (50 mL) at room temperature for 26 hours. Remove volatiles under reduced pressure, triturate the residual oil with diethyl ether and filter the resultant mixture. Dissolve the filter cake in dichloromethane, wash with water (3×), and evaporate the solvent under reduced pressure. Flash chromatograph the residue on silica gel, eluting with dichloromethane-methanol-ammonium hydroxide (98:2:0.1), and crystallize the eluate from ethanol to obtain the title compound, $C_{17}H_{16}N_4O_4S$, mp 147–148.5° C. FABMS: MH$^+$ 373 (100%).

Example 3
[[[6-(3-methyl-2-pyridinyl)-1,7-naphthyridin-8-yl]amino]sulfonyl]acetic acid, sodium salt Heat a stirred solution of [[[6-(3-methyl-2-pyridinyl)-1,7-naphthyridin-8-yl]amino]sulfonyl]acetic acid, methyl ester (4.17 g, 0.011 mol) and sodium hydroxide (2.30 g., 0.058 mol) in water (330 mL) at 60° C. for 2 hours. Concentrate the solution in vacuo to 25 mL, acidify to pH 4–5 with acetic acid and chill to 4° C. Filter the resultant precipitate and wash with cold water. Dry over phosphorus pentoxide at 43° C. and crystallize the crude product from methanol-water to obtain the title compound as a hydrate, $C_{16}H_{13}N_4O_4SNa \cdot H_2O$, mp 224–226° C. (dec). FABMS: MNa$^+$ 381 (100%).

To obtain the free acid form of the title compound, acidify a solution of the sodium salt (432 mg, 1.08 mmol) in 20 mL of water with 1.08 mL of 1.00N hydrochloric acid. Filter the precipitate, wash with water and dry in vacuo at 50° C. to obtain the free acid form of the title compound, $C_{16}H_{14}N_4O_4S$, mp 182.5–184° C. (dec). FABMS: MH$^+$ 359 (100%).

Example 4
4-[[[6-(3-methyl-2-pyridinyl)-1,7-naphthyridin-8-yl]amino]sulfonyl]benzoic acid, sodium salt

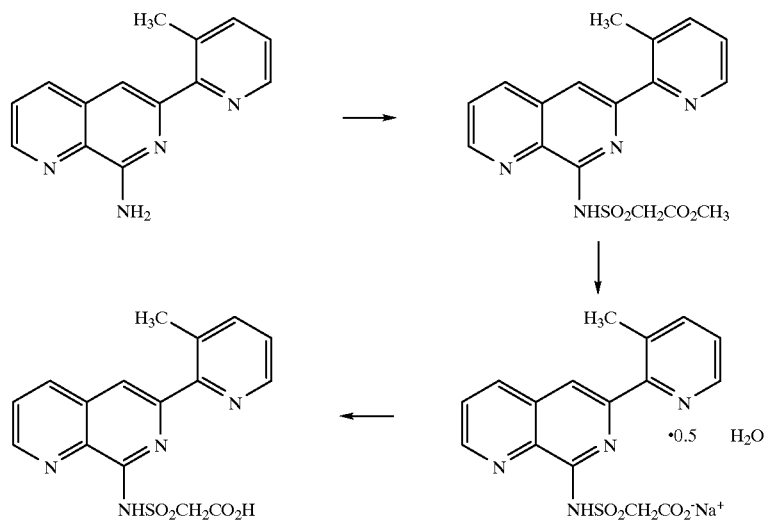

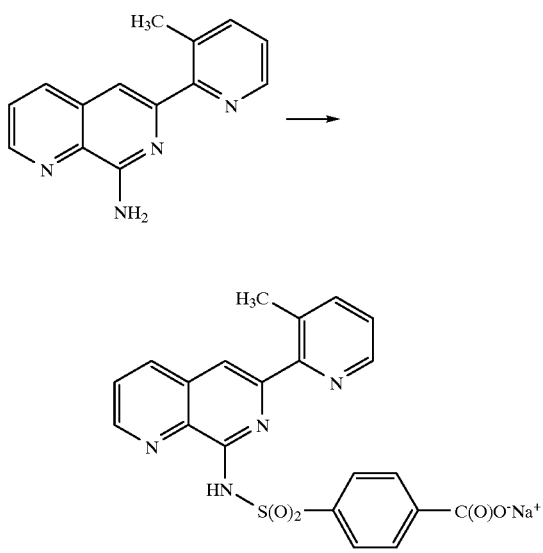

Add 4-(chlorosulfonyl)benzoic acid (3.40 g, 0.0154 mol) to a stirred solution of 8-amino-6-(3-methyl-2-pyridinyl)-1,7-naphthyridine (3.26 g, 0.0138 mol), triethylamine (5.2 mL, 0.0373 mol), 4-N,N-dimethylaminopyridine (0.3 g) in anhydrous dichloromethane (40 mL). Stir 5 days at room temperature, remove volatiles in vacuo, and chromatograph the residue on silica gel, eluting with dichloromethane-methanol-ammonium hydroxide in a stepped gradient of (90:9:0.1) to (80:18:0.1). Triturate the crude product thus obtained with hot ethanol (50–80 mL), filter, and suspend the isolated solid in water (100 mL). Adjust the pH to 12 with 6N sodium hydroxide to dissolve the solid; then acidify to pH 4.4 by addition of acetic acid. Collect the resultant precipitate and dry to obtain the free acid form of the title compound as a 0.5 hydrate, $C_{21}H_{16}N_4O_4S.0.5\ H_2O$, mp 337–8° C. (dec). FABMS: $MH^+$ 421 (100%).

To a stirred suspension of the free acid (493 mg, 1.17 mmol) in water (80 mL) add 0.100N sodium hydroxide (11.7 mL, 1.17 mmol). Warm the mixture to dissolve the solids, remove water under reduced pressure and reflux the residue in methanol (25 mL). Allow the mixture to cool to room temperature and filter to obtain the title sodium salt as a 0.25 hydrate, $C_{21}H_{15}N_4O_4SNa.0.25\ H_2O$, mp>360° C. FABMS: $MH^+$ 421 (48%); $MNa^+$ 443 (25%).

Example 5

8-[2-(2-Pyridinylmethylene)-hydrazino]-6-(3-methyl-2-pyridinyl)-1,7-naphthyridine

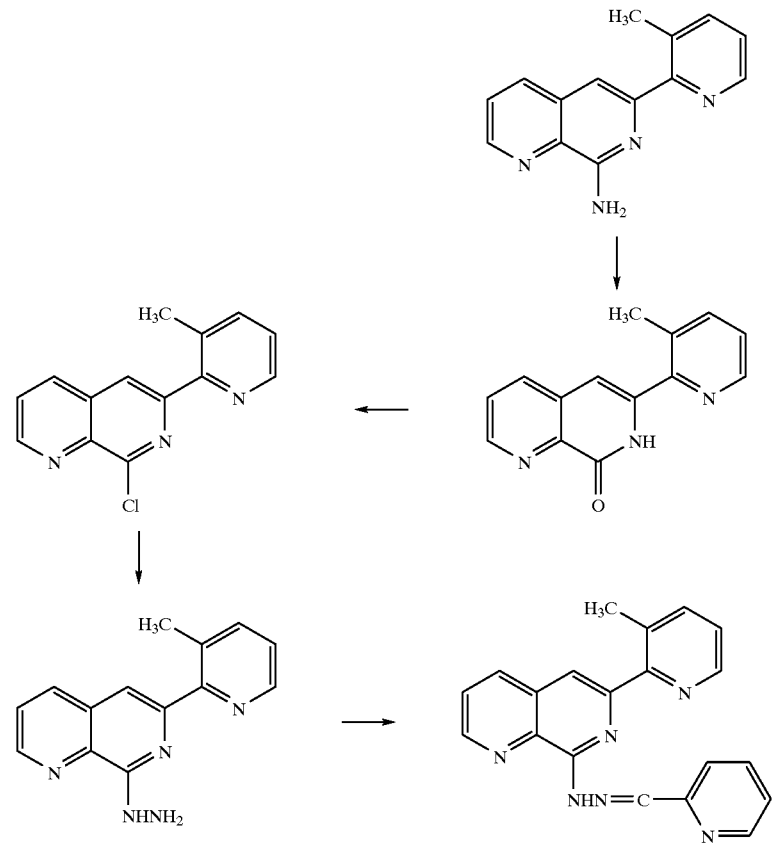

A. 8-Oxo-6-(3-methyl-2-pyridinyl)-1,7-naphthyridine

Reflux a mixture of 8-amino-6-(3-methyl-2-pyridinyl)-1,7-naphthyridine (17.3 g, 0.0732 mol) in concentrated hydrochloric acid (120 mL) for 17 hours. Concentrate to a semisolid under reduced pressure. Dissolve this residue in cold water (500 mL) and basify the solution to pH ~7.5 with concentrated ammonium hydroxide. Dilute the resultant suspension with water (50 mL) and cool in an ice-water bath. Filter the mixture, triturate the isolated solids with isopropanol, refilter and crystallize the solids from ethanol to obtain the title compound, mp 225–7° C.

B. 8-Chloro-6-(3-methyl-2-pyridinyl)-1,7-naphthyridine

Heat a mixture of 8-oxo-6-(3-methyl-2-pyridinyl)-1,7-naphthyridine (16.4 g, 69.1 mmol) in phosphorus oxychloride (200 mL) on a steam bath for 3 hours. Remove excess phosphorus oxychloride under reduced pressure, cool in an ice-water bath and add ice (100 g) and water (100 mL). Add concentrated ammonium hydroxide to neutralize the solution, while maintaining the temperature below 10° C. Filter the resultant mixture, air dry the solids and triturate with boiling benzene (1 L). Concentrate the mixture, filter and crystallize the isolated solid from benzene to obtain the title compound, mp 130–1° C.

C. 8-hydrazino-6-(3-methyl-2-pyridinyl)-1,7-naphthyridine

To a solution of 98% hydrazine hydrate (7.4 g, 0.148 mol) in ethanol (100 mL) add 8-chloro-6-(3-methyl-2-pyridinyl)-1,7-naphthyridine (8.5 g, 0.0332 mol) and reflux for 2.5 hours. Concentrate the reaction mixture under reduced pressure, triturate the residual solid with water, filter and crystallize the isolated solid from benzene-petroleum ether to obtain the title compound, mp 115–6° C.

D. 8-[2-(2-Pyridinylmethylene)-hydrazino]-6-(3-methyl-2-pyridinyl)-1,7-naphthyridine, 0.2 hydrate To a suspension of 8-hydrazino-6-(3-methyl-2-pyridinyl)-1,7-naphthyridine (5 g, 19.9 mmol) in ethanol (50 mL) add 2-pyridinecarboxaldehyde (2.7 g, 25.2 mmol). Reflux the mixture for 1 hour. Allow the mixture to cool, and remove solvent under reduced pressure. Recrystallize the residual solid from chloroform-hexane to obtain the title compound, $C_{20}H_{16}N_6$, mp 178–179° C. FABMS: MH$^+$ 341 (100%).

Example 6

8-Mercapto-6-(3-methyl-2-pyridinyl)-1,7-naphthyridine

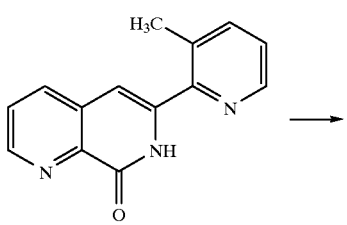

-continued

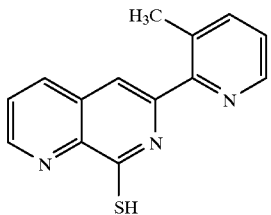

Reflux a mixture of 8-oxo-6-(3-methyl-2-pyridinyl)-1,7-naphthyridine (10.0 g, 42.1 mmol) and phosphorus pentasulfide (9.8 g, 44.1 mmol) in pyridine (250 mL) on a steam bath for 3 hours. Pour the reaction solution into boiling water (400 mL) and maintain the resultant mixture at the boiling point for 1 hour. Filter the mixture, dissolve the collected solid in hot chloroform and treat with decolorizing charcoal. Filter the charcoal, heat the filtrate to boiling and induce crystallization by the addition of diethyl ether. Recrystallize the precipitate thus obtained from chloroform to obtain the title compound, $C_{14}H_{11}N_3S$, mp 220–222.5° C. FABMS: MH$^+$ 254 (100%).

Example 7

8-(p-Aminobenzenesulfonamido)-6-(3-methyl-2-pyridinyl)-1,7-naphthyridine

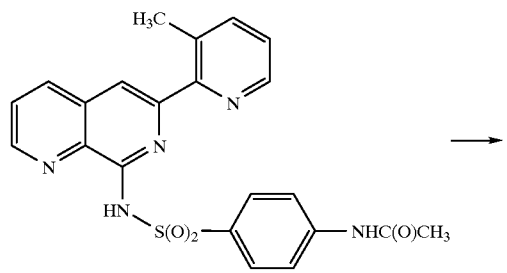

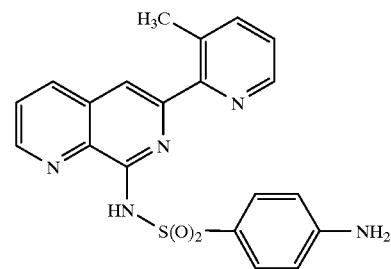

Reflux for 6 hours a stirred mixture of 8-(p-acetamidobenzenesulfonamido)-6-(3-methyl-2-pyridinyl)-1,7-naphthyridine (3.67 g, 8.47 mmol) in 2N aqueous sodium hydroxide (37 mL, 74 mmol). Cool the mixture to <15° C., acidify to pH 6 with acetic acid-water (1:4) and filter. Reflux the collected solid in methanol (125 mL), filter the hot mixture and wash the filter cake with methanol (25 mL). Dry the collected solid under high vacuum to obtain the title compound as a dihydrate, $C_{20}H_{17}N_5O_2S.2\ H_2O$, mp 278–83° C. FABMS: MH$^+$ 392 (100%).

Example 8

4-(acetylamino)-N-[6-(3-methyl-2-pyridinyl)-1,7-naphthyridin-8-yl]benzamide

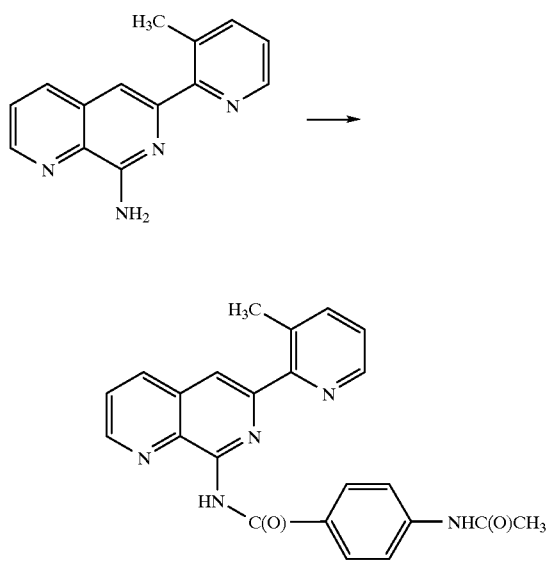

Add 8-amino-6-(3-methyl-2-pyridinyl)-1,7-naphthyridine (332 mg, 1.41 mmol) to a stirred suspension of 4-acetamidobenzoic acid (229 mg, 1.78 mmol), 1-(3-N,N-dimethylaminopropyl)-3-ethylcarbodiimide hydrochloride (DEC.HCl; 270 mg, 1.41 mmol) and 1-hydroxybenzotriazole (190 mg, 1.41 mmol) in dichloromethane (15 mL) at 18° C. Remove the cooling bath and allow the mixture to stir at room temperature for 16 hours. Dilute the reaction mixture with dichloromethane (20 mL), add another portion of DEC.HCl and stir for an additional 20 hours. Remove volatiles under reduced pressure, dissolve the residue in dichloromethane-methanol-ammonium hydroxide (95:5:0.125) and filter through Celite. Flash chromatograph the filtrate on silica gel, eluting with dichloromethane-methanol-ammonium hydroxide (90:9:0.125), and crystallize the solid thus isolated from acetonitrile to obtain the title compound as a 0.25 hydrate, $C_{23}H_{19}N_5O_2 \cdot 0.25\ H_2O$, mp 233–239.5° C. FABMS: $MH^+$ 398 (100%).

Example 9

Phenylmethyl [4-[[[6-(3-methyl-2-pyridinyl)-1,7-naphthyridin-8-yl]amino]sulfonyl]phenyl]carbamate (I) and 4-[(aminocarbonyl)amino]-N-[6-(3-methyl-2-pyridinyl)-1,7-naphthyridin-8-yl]benzenesulfonamide (II)

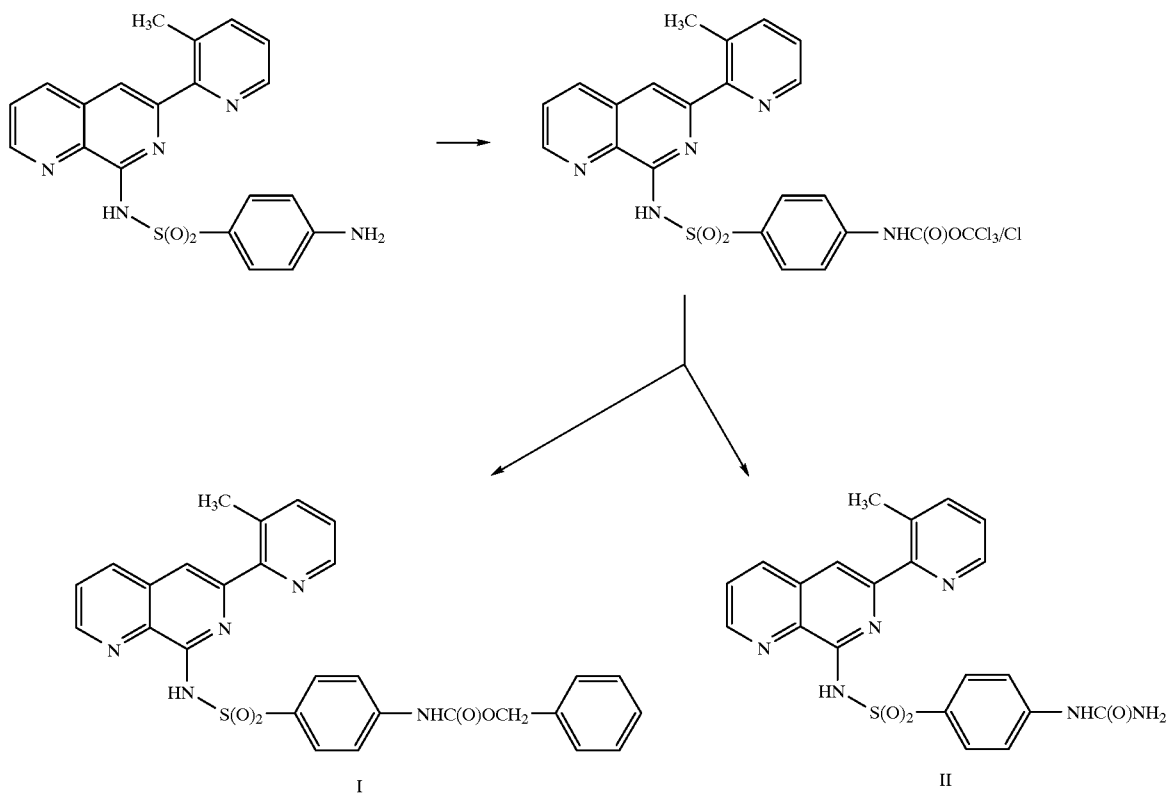

Rapidly add trichloromethylchloroformate (0.16 mL, 1.32 mmol) to a stirred suspension of 8-(p-aminobenzenesulfonamido)-6-(3-methyl-2-pyridinyl)-1,7-naphthyridine (0.43 g, 1.10 mmol), triethylamine (0.183 mL, 1.32 mmol) and 4-dimethylaminopyridine (0.03 g) in dichloromethane (25 mL) at 25° C. Stir for 1 hour at room temperature. Add this reaction mixture to a stirred solution of the lithium salt of benzyl alcohol [prepared by stirring a 1M solution (1.5 mL, 1.5 mmol) of lithium bis(trimethylsilyl)amide in tetrahydrofuran with benzyl alcohol (0.15 mL, 1.45 mmol) in dichloromethane (20 mL) for 0.5 hour]. Stir the resultant mixture for 3 days at room temperature. Introduce additional lithium salt of benzyl alcohol [prepared as described above from a 1M solution (3 mL, 3 mmol) of lithium bis(trimethylsilyl)amide in tetrahydrofuran with benzyl alcohol (0.30 mL, 2.90 mmol) in dichloromethane (1 mL)] and reflux for 24 hours. Remove solvent under reduced pressure, and flash chromatograph on a column of silica gel, eluting with a stepped gradient of dichloromethane-methanol-ammonium hydroxide (95:5:0.1→90:9:0.1) to obtain the title compounds I and II. Reflux the less polar solid thus isolated in methanol-ethanol (1:1) for 5–10 minutes, cool to room temperature, and filter to obtain title compound I as a 0.25 hydrate, $C_{28}H_{23}N_5O_4S \cdot 0.25\ H_2O$, mp 229.5–231° C. (dec). FABMS: MH$^+$ 526 (100%). Crystallize from ethanol (5 mL) the more polar solid eluted from the column to obtain title compound II as a 0.5 hydrate, $C_{21}H_{18}N_6O_3S \cdot 0.5\ H_2O$, mp 258.5–260° C. (dec). FABMS: MH$^+$ 435 (94%).

Example 10
N-[6-(3-methyl-2-pyridinyl)-1,7-naphthyridin-8-yl]-4-(phenylmethoxy)-benzenesulfonamide Under a nitrogen atmosphere, add a 1M solution (3.05 mL, 3.05 mmol) of lithium bis(trimethylsilyl)amide in tetrahydrofuran to a stirred suspension of N-[6-(3-methyl-2-pyridinyl)-1,7-naphthyridin-8-yl]-4-(hydroxy)-benzenesulfonamide (593 mg, 1.37 mmol) in N,N-dimethylformamide (25 mL) at room temperature. Stir 0.5 hour at room temperature, and add benzyl bromide (0.18 mL, 1.51 mmol). Heat at 75° C. for 0.75 hour, cool to room temperature and remove volatiles at reduced pressure. Stir the residue with water and acidify by the addition of 3M hydrochloric acid (1 mL). Filter, reflux the solids in ethanol (75 mL), cool the mixture to room temperature, and filter again. Flash chromatograph the collected solids on silica gel, eluting with dichloromethane-methanol-ammonium hydroxide (98:2:0.1), to obtain the title compound, $C_{27}H_{22}N_4O_3S$, mp 204–5° C. FABMS: MH$^+$ 483 (48%).

Example 11

N-4-[[[6-(3-methyl-2-pyridinyl)-1,7-naphthyridin-8-yl]amino]sulfonyl]phenyl]benzene acetamide

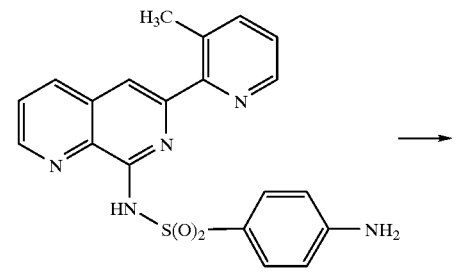

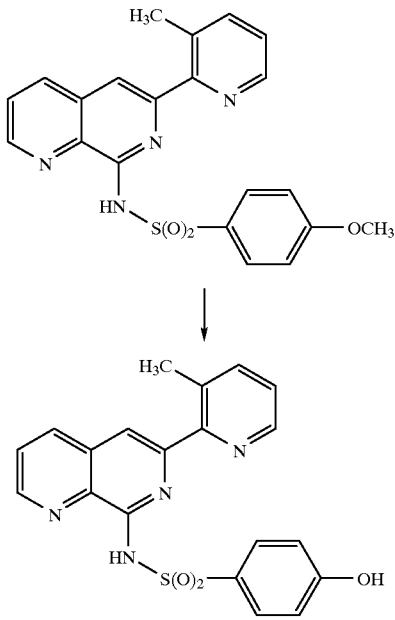

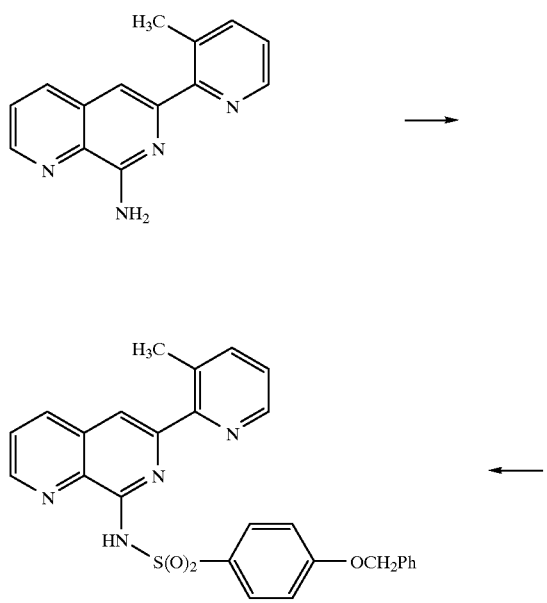

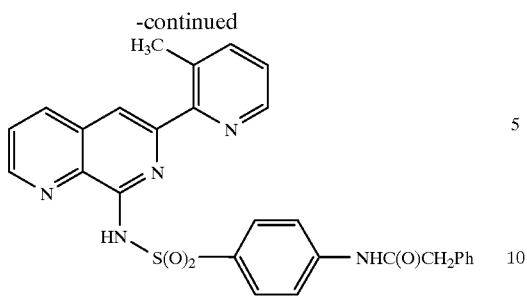

Add phenylacetyl chloride (0.35 mL, 2.7 mmol) to a stirred suspension of 8-(p-aminobenzenesulfonamido)-6-(3-methyl-2-pyridinyl)-1,7-naphthyridine (0.83 g, 2.1 mmol), triethylamine (0.37 mL, 2.7 mmol) and 4-dimethylaminopyridine (0.02 g) in dry dichloromethane (50 mL) at room temperature. Stir for 16 hours at room temperature; add additional triethylamine (0.374 mL, 5.4 mmol), followed by phenylacetyl chloride (0.35 mL, 2.7 mmol); then reflux for 18 hours and stir at room temperature for 5 days. Filter the mixture, and concentrate the filtrate under reduced pressure. Dissolve the residue in hot N,N-dimethylformamide, cool to room temperature, filter the precipitate (triethylamine hydrochloride) and concentrate the filtrate in vacuo. Flash chromatograph the residue on silica gel, eluting with dichloromethane-methanol-ammonium hydroxide (90:10:0.1), to obtain the title compound as a 0.5 hydrate, $C_{28}H_{23}N_5O_3S \cdot 0.5\ H_2O$, mp 258–9° C. (dec). FABMS: MH$^+$ 510 (100%).

Example 12
N-[6-(3-methyl-2-pyridinyl)-1,7-naphthyridin-8-yl]benzenesulfonamide

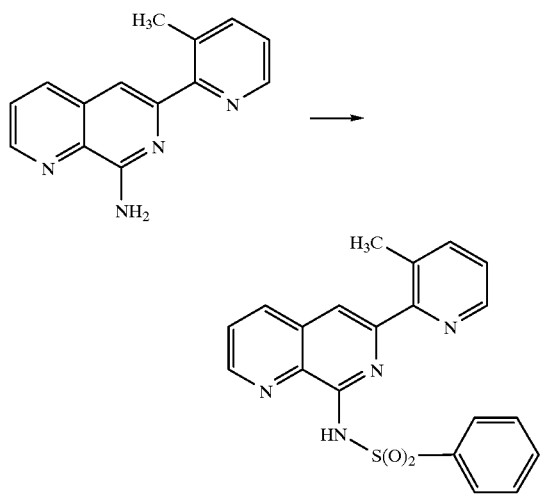

To a stirred mixture of 8-amino-6-(3-methyl-2-pyridinyl)-1,7-naphthyridine (1.06 g, 4.49 mmol), triethylamine (0.50 g, 4.94 mmol), and 4-N,N-dimethylaminopyridine (0.055 g) in dry dichloromethane (30 mL), add benzenesulfonyl chloride (0.63 mL, 4.94 mmol) and reflux for 21 hours. Cool to room temperature, filter the mixture, wash the solids with cold dichloromethane and vacuum dry to obtain the title compound $C_{20}H_{16}N_4O_2S$, mp 259.5–261.5° C. (dec). FABMS: MH$^+$ 377 (100%).

Example 13
N-[4-[[(6-phenyl-1,7-naphthyridin-8-yl)amino]sulfonyl]phenyl]acetamide

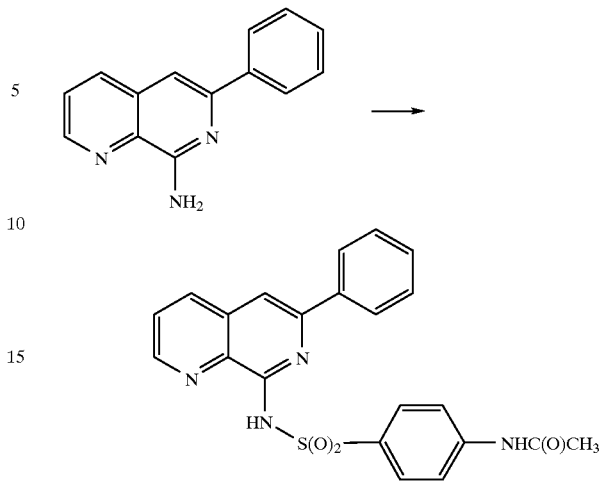

Reflux a stirred mixture of 8-amino-6-phenyl-1,7-naphthyridine (0.51 g, 2.30 mmol), triethylamine (0.26 g, 2.53 mmol), 4-N,N-dimethylaminopyridine (0.03 g) and N-acetylsulfanilyl chloride (0.59 g, 2.53 mmol) in dry dichloromethane (14 mL) for 45 hours. Cool the reaction mixture to room temperature, wash with 1.1M sodium bicarbonate solution (30 mL), followed by water (2×25 mL), dry over anhydrous magnesium sulfate, and remove solvent under reduced pressure. Flash chromatograph the residue on silica gel, eluting with dichloromethane-methanol-ammonium hydroxide (95:5:0.125) to obtain the title compound as a monohydrate, $C_{22}H_{18}N_4O_3S \cdot H_2O$, mp 135.5–137° C. (dec). FABMS: MH$^+$ 419 (100%).

Example 14
N-[4-[[[6-(2-pyridinyl)-1,7-naphthyridin-8-yl)amino]sulfonyl]phenyl]acetamide

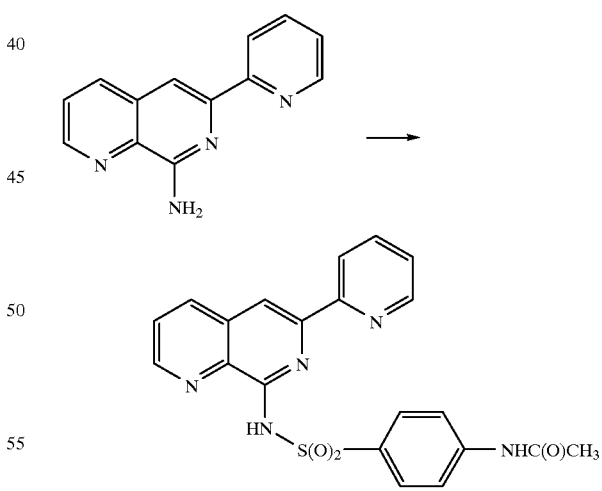

Reflux a stirred solution of 8-amino-6-(2-pyridinyl)-1,7-naphthyridine (160 mg, 0.718 mmol), triethylamine (80.5 mg, 0.795 mmol), 4-N,N-dimethylaminopyridine (8.5 mg, 0.0688 mmol) and N-acetylsulfanilyl chloride (185 mg, 0.791 mmol) in dry dichloromethane (6 mL) for 11 hours. Cool the reaction mixture and filter. Crystallize from ethanol the crude product thus obtained and filter to obtain the title compound as a 0.25 hydrate, $C_{21}H_{17}N_5O_3S \cdot 0.25\ H_2O$, mp 292–293° C. (dec). FABMS: MH$^+$ 420 (100%).

Example 15

N-[6-(3-methyl-2-pyridinyl)-1,7-naphthyridin-8-yl]-4-[(phenylmethyl)amino]benzenesulfonamide

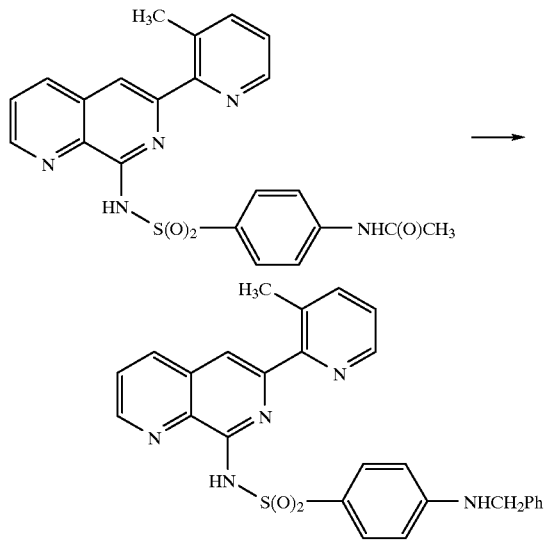

Add 60% sodium hydride dispersion in mineral oil (94.3 mg, 2.36 mmol) to a stirred suspension of 8-(p-acetamidobenzenesulfonamido)-6-(3-methyl-2-pyridinyl)-1,7-naphthyridine (929 mg, 2.14 mmol) in dry N,N-dimethylformamide (DMF; 25 mL) and stir the resultant mixture at room temperature for 45 minutes. Dilute the reaction mixture with DMF (10 mL), add another portion of sodium hydride dispersion (9.4 mg, 0.235 mmol) and stir at room temperature for another 10 minutes. To this mixture add benzyl bromide (0.28 mL, 2.35 mmol) and stir at room temperature for 16 hours. Concentrate the reaction mixture under reduced pressure, dilute the concentrate with dichloromethane (30 mL) and pour onto ice. Separate the layers and extract the aqueous phase with dichloromethane (2×10 mL). Clarify the combined dichloromethane extracts by adding a small volume of methanol, and dry over anhydrous magnesium sulfate. Remove solvent under reduced pressure, and flash chromatograph the residue on silica gel, eluting with dichloromethane-methanol-ammonium hydroxide (98:2:0.125) to obtain the title compound as a 0.125 hydrate, $C_{27}H_{23}N_5O_2S \cdot 0.125H_2O$, mp 131.5–134° C. (dec). FABMS: MH$^+$ 482 (100%).

Example 16

N-[4-[[(1,7-naphthyridin-8-yl)amino]sulfonyl]phenyl]acetamide

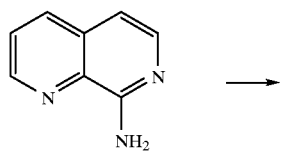

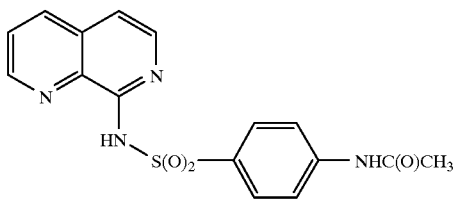

Stir a mixture of 8-amino-1,7-naphthyridine (1.00 g, 6.91 mmol), triethylamine (0.77 g, 7.60 mmol), 4-N,N-dimethylaminopyridine (0.08 g) and N-acetylsulfanilyl chloride (1.78 g, 7.60 mmol) in dry dichloromethane (25 mL) for 20 hours at room temperature. Cool the reaction mixture to 0° C. and filter. Flash chromatograph the crude solid product on silica gel, eluting with dichloromethane-methanol-ammonium hydroxide (95:5:0.125→90:9:0.125) and crystallize the chromatographed product from methanol to obtain the title compound as a 0.375 hydrate, $C_{16}H_{14}N_4O_3S \cdot 0.375\ H_2O$, mp 260–261° C. (dec). FABMS: MH$^+$ 343 (100%).

Example 17

N-[6-(3-methyl-2-pyridinyl)-1,7-naphthyridin-8-yl]-3-pyridinesulfonamide

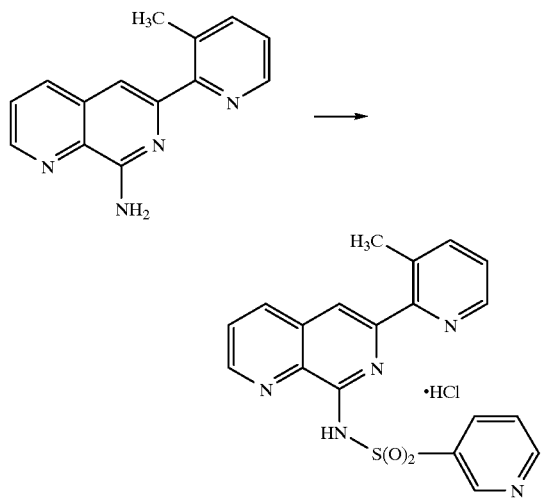

To a stirred mixture of 8-amino-6-(3-methyl-2-pyridinyl)-1,7-naphthyridine (508 mg, 2.15 mmol), triethylamine (0.66 mL, 4.74 mmol), and 4-N,N-dimethylaminopyridine (26 mg) in dry dichloromethane (18 mL), add 3-pyridinesulfonyl chloride (508 mg, 2.36 mmol) and reflux for 22 hours. Cool to room temperature and filter the mixture to obtain the free base form of the title compound, mp 267–268.5° C. (dec).

Suspend a sample of the free base of the title compound (553 mg, 1.47 mmol) in ethanol (5 mL) and acidify with 5.3M ethanolic hydrochloric acid (18.6 mL, 98.6 mmol). Remove solvent from the resultant clear yellow solution under reduced pressure. Triturate the residual oil with diethyl ether, filter the resultant solid and dry under vacuum to obtain the hydrochloride salt of the title compound $C_{19}H_{15}N_5O_2S \cdot 1.4HCl \cdot 0.5H_2O$, mp 245–247° C. (dec). FABMS: MH$^+$ 378 (100%).

Example 18

4-Methoxy-N-[6-(3-methyl-2-pyridinyl)-1,7-naphthyridin-8-yl]benzenesulfonamide

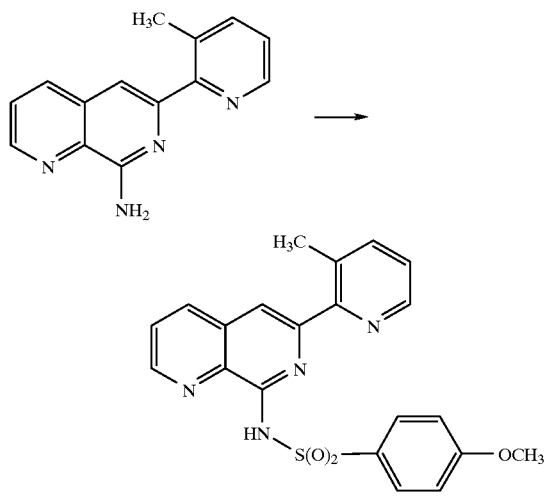

Stir a mixture of 8-amino-6-(3-methyl-2-pyridinyl)-1,7-naphthyridine (597 mg, 2.53 mmol) and 4-methoxybenzenesulfonyl chloride (575 mg, 2.78 mmol) in dry pyridine (14 mL) for 22 hours at room temperature. Add an additional portion of 4-methoxybenzenesulfonyl chloride (50 mg, 0.242 mmol) and reflux the reaction mixture. After 5 hours, add a third portion of 4-methoxybenzenesulfonyl chloride (56.3 mg, 0.273 mmol) and stir at room temperature for 24 hours. Filter the mixture. Treat the filtrate with water (70 mL) and extract with dichloromethane (3×20 mL). Combine the extracts, wash with water (3×10 mL) and dry over anhydrous sodium sulfate. Filter the drying agent, remove solvent under reduced pressure, and triturate the residue with diethyl ether. Filter and dry the isolated solids under vacuum to obtain the title compound as a 0.25 hydrate $C_{21}H_{18}N_4O_3S \cdot 0.25H_2O$, mp 180–181° C. (dec). FABMS: $MH^+$ 407 (100%).

Example 19

N-[[4-(acetylamino)phenyl]sulfonyl]-N-[6-(3-methyl-2-pyridinyl)-1,7-naphthyridin-8-yl]acetamide

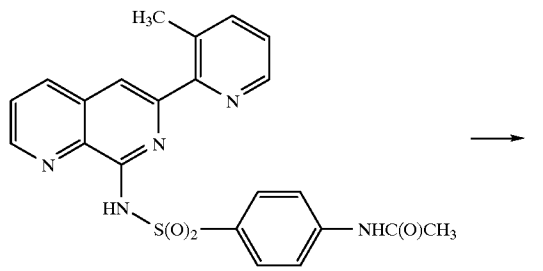

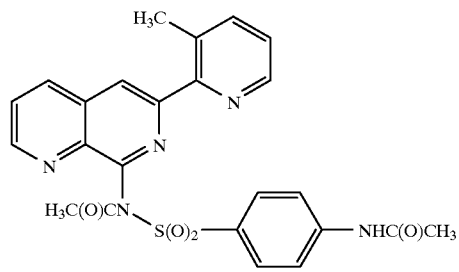

Under a nitrogen atmosphere, add 60% sodium hydride dispersion in mineral oil (50.3 mg, 1.26 mmol) to a stirred hazy solution of 8-(p-acetamidobenzenesulfonamido)-6-(3-methyl-2-pyridinyl)-1,7-naphthyridine (496 mg, 1.14 mmol) in dry N,N-dimethylformamide (DMF; 24 mL), and stir the resultant mixture at room temperature for 30 minutes. Add acetyl chloride (0.09 mL, 1.27 mmol) and stir for 24 hours at room temperature. Add a second portion of acetyl chloride (0.05 mL, 0.703 mmol) and heat at 50° C. for 22 hours. Allow the reaction mixture to cool, remove solvent under reduced pressure, triturate the residue with isopropyl ether and filter. Dissolve the isolated solid in dichloromethane-methanol-ammonium hydroxide (95:5:0.1) and flash chromatograph on silica gel, eluting with dichloromethane-methanol-ammonium hydroxide (95:5:0.1). Triturate the product thus isolated with diethyl ether and filter to obtain the title compound, $C_{24}H_{21}N_5O_4S$, mp 235.5–236.5° C. (dec). FABMS: $MH^+$ 476 (57%).

Example 20

2-(2-Methoxyethoxy)ethyl [4-[[[6-(3-methyl-2-pyridinyl)-1,7-naphthyridin-8-yl]amino]sulfonyl]phenyl]carbamate

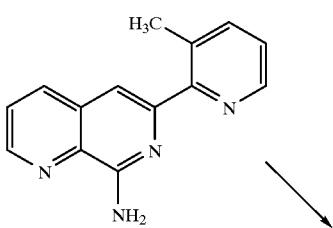

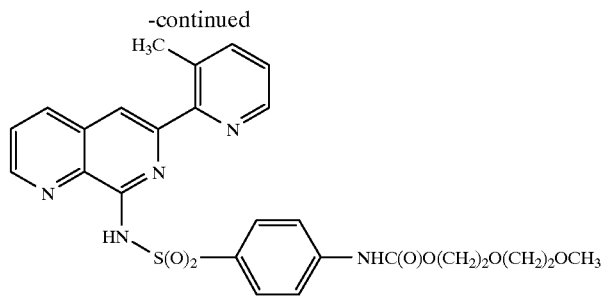

Stir at room temperature a solution of 8-amino-6-(3-methyl-2-pyridinyl)-1,7-naphthyridine (412 mg, 1.74 mmol), triethylamine (0.27 mL, 1.92 mmol), 4-N,N-dimethylaminopyridine (21 mg) and 4-[2-methoxy[2-ethoxy (ethoxy)]carbonylamino]benzenesulfonyl chloride (650 mg, 1.92 mmol) in dry dichloromethane (25 mL). After 48 hours, add a second portion (75 mg, 0.222 mmol) of the sulfonyl chloride reagent and continue to stir at room temperature for another 96 hours. Wash the reaction mixture with water (3×15 mL), dry over anhydrous magnesium sulfate, filter the drying agent and remove solvent under reduced pressure. Flash chromatograph the residue on silica gel, eluting with dichloromethane-methanol-ammonium hydroxide (95:5:0.1). Crystallize from ethanol the product thus isolated and filter to obtain the title compound, $C_{26}H_{27}N_5O_6S$, mp 182.5–185° C. (dec). FABMS: MH+ 538 (100%).

Example 21
4-Hydroxy-N-[6-(3-methyl-2-pyridinyl)-1,7-naphthyridin-8-yl]benzenesulfonamide

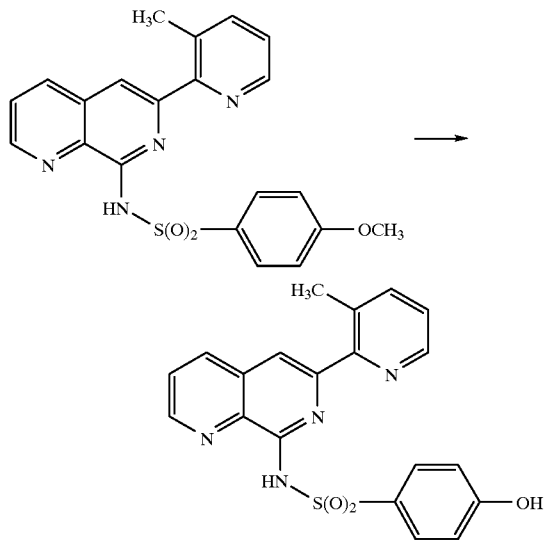

Under a nitrogen atmosphere, heat a stirred solution of 4-methoxy-N-[6-(3-methyl-2-pyridinyl)-1,7-naphthyridin-8-yl]benzenesulfonamide (229 mg, 0.563 mmol) and sodium thiomethoxide (98.6 mg, 1.41 mmol) in N,N-dimethylformamide (10 mL) at 100–110° C. for 30 minutes. Raise the temperature to 150° C., heat for 1.5 hours, then add an additional quantity (56.6 mg, 0.808 mmol) of sodium thiomethoxide and continue heating at 150° C. for 3.5 hours. Evaporate solvent under reduced pressure and flash chromatograph the residue on silica gel, eluting with dichloromethane-methanol-ammonium hydroxide (90:9:1). Crystallize from methanol-acetonitrile the product thus isolated and triturate with diethyl ether to obtain the title compound, $C_{20}H_{16}N_4O_3S$, mp 262–262.5° C. (dec).
1HNMR [DMSO, 300 MHz]: δ2.36 (s, 2.25H); 2.72 (s, 0.75H); 6.71 (d, J≈7.5 Hz, 1.5H); 6.86 (d, J≈7.5 Hz, 0.75H); 7.39 (dd; 0.75H); 7.55 (dd; 0.25H); 7.66–7.77 (m, 1H); 7.79–7.90 (m, 3.5H); 7.95 (d, J≈7.5 Hz, 0.25H); 8.41 (d, J≈7.5 Hz, 0.25H); 8.49 (m, 1.5H); 8.74 (d 0.25H); 8.91 (d, 0.25H); 9.03 (d, 0.75H); 10.31* (s, 0.25H); 10.39* (s, 0.75H); 10.71* (br s, 0.75H); 13.14* (br s, 0.25H) [*D2O-exchangeable].

Example 22
N-[6-(3-methyl-2-pyridinyl)-1,7-naphthyridin-8-yl] methanesulfonamide

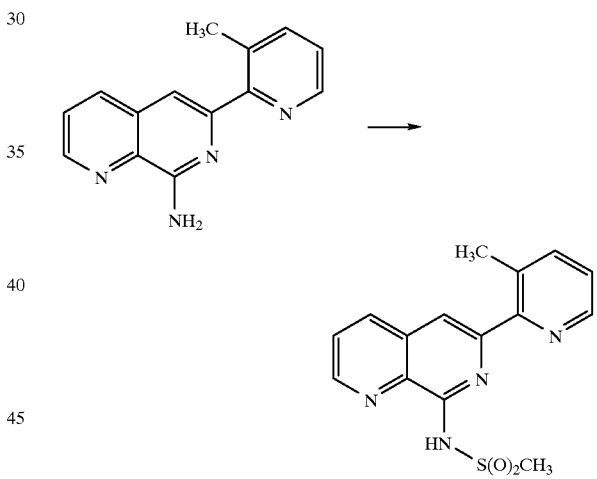

Stir at room temperature a mixture of 8-amino-6-(3-methyl-2-pyridinyl)-1,7-naphthyridine (1.05 g, 4.48 mmol), triethylamine (0.68 mL, 4.89 mmol) and methanesulfonyl chloride (0.38 mL, 4.89 mmol) in dry dichloromethane (25 mL). After 72 hours, add a second portion (0.08 mL, 1.03 mmol) of methanesulfonyl chloride and continue to stir at room temperature for another 24 hours. Filter, wash the filtrate with water (3×35 mL), dry over anhydrous sodium sulfate, filter the drying agent and remove solvent under reduced pressure. Flash chromatograph the residue on silica gel, eluting with dichloromethane-methanol-ammonium hydroxide (98:2:0.1). Crystallize from ethanol the product thus isolated and filter to obtain the title compound, $C_{15}H_{14}N_4O_2S$, mp 184.5–185.5° C. FABMS: MH+ 315 (100%).

Example 23
N-[4-[[[6-(3-methyl-2-pyridinyl)-1,7-naphthyridin-8-yl] amino]sulfonyl]phenyl]benzamide

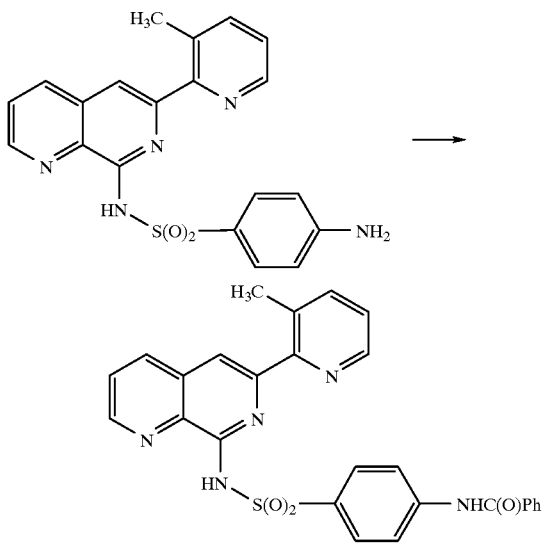

Add a solution of benzoyl chloride (0.044 mL, 0.383 mmol) in dichloromethane (5 mL) to a stirred suspension of 8-(p-aminobenzenesulfonamido)-6-(3-methyl-2-pyridinyl)-1,7-naphthyridine (136 mg, 0.348 mmol) and triethylamine (0.053 mL, 0.383 mmol) in dichloromethane (25 mL), maintained at 5° C. Allow the mixture to warm to room temperature, then reflux for 19 hours. Chill the reaction mixture to 0° C., filter, wash the solids with cold dichloromethane and vacuum dry to obtain the title compound, $C_{27}H_{21}N_5O_3S$, mp 270–272° C. (dec). FABMS: MH$^+$ 496 (75%).

Example 24
N-[4-[[[6-(3-methyl-2-pyridinyl)-1,7-naphthyridin-8-yl]amino]sulfonyl]phenyl]cyclohexanecarboxamide

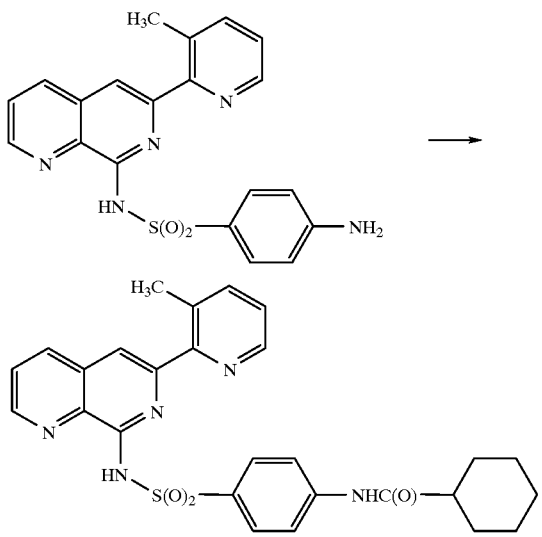

Reflux a stirred mixture of 8-(p-aminobenzenesulfonamido)-6-(3-methyl-2-pyridinyl)-1,7-naphthyridine (1.04 g, 2.65 mmol), triethylamine (0.053 mL, 0.383 mmol) and cyclohexanecarbonyl chloride (0.83 mL, 6.20 mmol) in dichloromethane (50 mL) for 5 days. Allow the reaction mixture to cool to room temperature, filter and wash the solids with dichloromethane. Crystallize from methanol and vacuum dry to obtain the title compound, $C_{27}H_{27}N_5O_3S$, mp 240–241° C. (dec). FABMS: MH$^+$ 502 (100%).

Example 25
Methyl 4-[[[4-[[[6-(3-methyl-2-pyridinyl)-1,7-naphthyridin-8-yl]amino]sulfonyl]phenyl]amino]carbonyl]benzoate

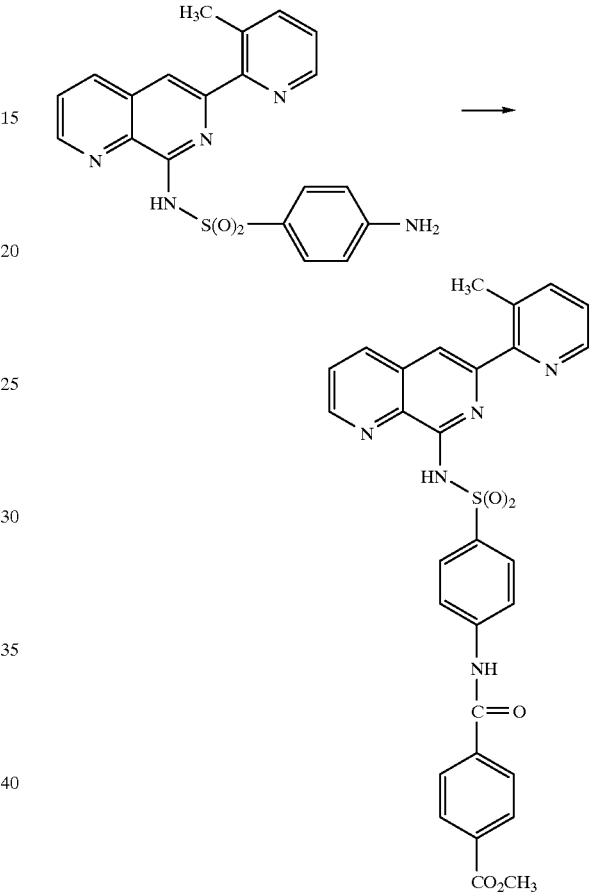

Reflux a stirred suspension of 8-(p-aminobenzenesulfonamido)-6-(3-methyl-2-pyridinyl)-1,7-naphthyridine (1.43 g, 3.65 mmol), triethylamine (1.22 mL, 0.876 mmol), terephthalic acid monomethyl ester chloride (1.74 mL, 8.76 mmol) and 4-N,N-dimethylaminopyridine (0.1 g) in dichloromethane (120 mL) for 4 days. Allow the reaction mixture to cool to room temperature, filter and wash the solids with dichloromethane. Dissolve the crude product in refluxing N,N-dimethylformamide (20 mL), filter the hot solution and concentrate the filtrate to a volume of <5 mL. Add water to the hot concentrate to the point of cloudiness, then allow the mixture to cool to room temperature. Filter and vacuum dry the solids to obtain the title compound as a 0.25 hydrate, $C_{29}H_{23}N_5O_3S \cdot 0.25H_2O$, mp 275–277° C. (dec). FABMS: MH$^+$ 554 (100%).

Example 26
N-[6-(3-methyl-2-pyridinyl)-1,7-naphthyridin-8-yl]-4-[[[(phenylmethyl)amino]carbonyl]amino]benzenesulfonamide

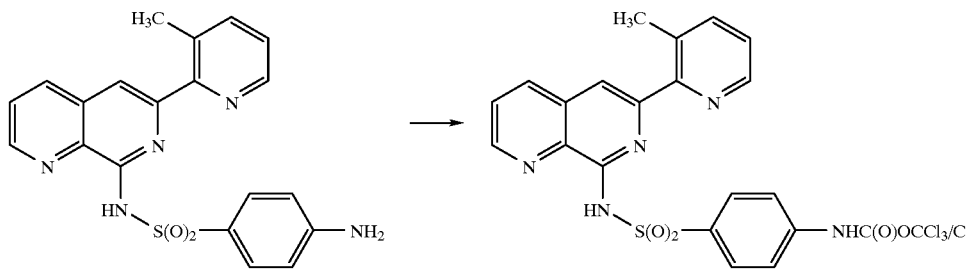

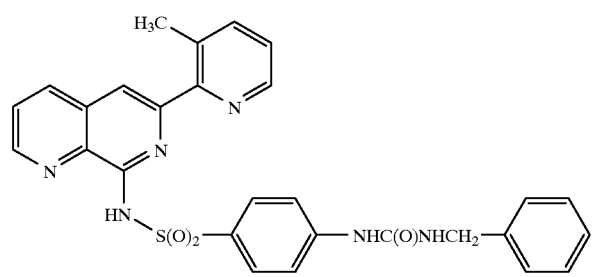

Rapidly add trichloromethylchloroformate (0.16 mL, 1.32 mmol) to a stirred suspension of 8-(p-aminobenzenesulfonamido)-6-(3-methyl-2-pyridinyl)-1,7-naphthyridine (0.43 g, 1.10 mmol), triethylamine (0.183 mL, 1.32 mmol) and 4-dimethylaminopyridine (0.03 g) in dichloromethane (25 mL) at 25° C. Stir for 1 hour at room temperature. Dilute the reaction mixture with dichloromethane (20 mL), add benzylamine (0.32 mL, 2.92 mmol) and stir at room temperature for 3 days. Add triethylamine (0.61 mL, 4.40 mmol), followed by additional benzylamine (0.16 mL, 1.46 mmol), and reflux for 2.5 hours. Cool to 0° C., filter, and crystallize from N,N-dimethylformamide-water. Filter, wash the solids with water followed by warm ethanol, and vacuum dry to obtain the title compound as a 0.25 hydrate, $C_{28}H_{24}N_6O_3S \cdot 0.25\ H_2O$, mp 274–275° C. (dec). FABMS: $MH^+$ 525 (100%).

Example 27

N-[6-(3-methyl-2-pyridinyl)-1,7-naphthyridin-8-yl]-2-thiophenesulfonamide

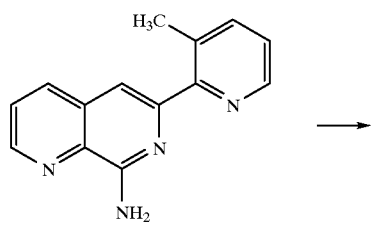

-continued

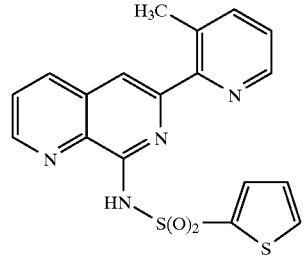

Stir at room temperature a mixture of 8-amino-6-(3-methyl-2-pyridinyl)-1,7-naphthyridine (0.97 g, 4.11 mmol), triethylamine (0.86 mL, 6.16 mmol), 4-N,N-dimethylaminopyridine (50 mg) and 2-thiophenesulfonyl chloride (1.12 g, 6.16 mmol) in dry dichloromethane (28 mL). After 48 hours, add a second portion (187 mg, 0.411 mmol) of the sulfonyl chloride reagent and triethylamine (0.14 mL, 1.0 mmol) and continue to stir at room temperature for another 96 hours. Filter the reaction mixture, wash the solids with dichloromethane and vacuum dry to obtain the title compound, $C_{18}H_{14}N_4O_2S_2$, mp 280.5–281° C. (dec). FABMS: $MH^+$ 382 (52%).

Example 28

4-Decylamino-N-[6-(3-methyl-2-pyridinyl)-1,7-naphthyridin-8-yl]-benzenesulfonamide

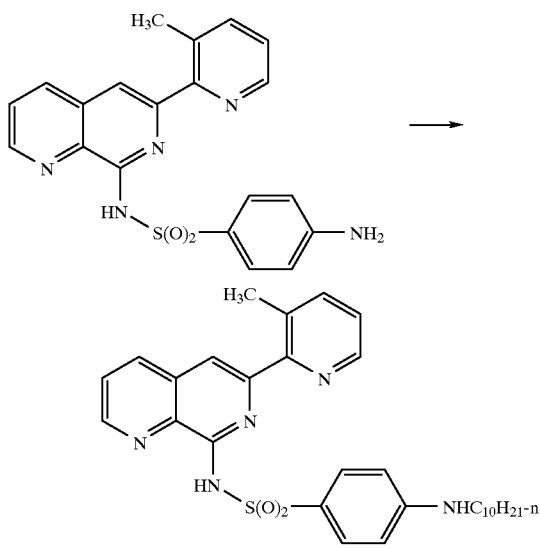

Under a nitrogen atmosphere, heat an intimate mixture of 8-(p-aminobenzenesulfonamido)-6-(3-methyl-2-pyridinyl)-1,7-naphthyridine (448 mg, 1.14 mmol) and tetrabutylammonium bromide (3.25 g, 10.1 mmol) in an oil bath maintained at 115° C. to form a molten mass. To the stirred mixture, add 1-bromodecane (0.24 mL, 1.16 mmol) and continue heating under nitrogen for 30 minutes. Add another portion (0.10 mL, 0.482 mmol) of 1-bromodecane, heat for 30 minutes, then add N,N-diisopropylethylamine (0.20 mL, 1.15 mmol) and heat for an additional 60 minutes. Allow the reaction mixture to cool to room temperature, dissolve in dichloromethane (5 mL) and flash chromatograph on silica gel, eluting with dichloromethane-methanol-ammonium hydroxide (98:2:0.1). Dissolve the product thus isolated in dichloromethane and treat with Darco G60. Filter, evaporate the filtrate under reduced pressure and crystallize the residue from ethanol. Filter and dry the solids under vacuum to obtain the title compound, $C_{30}H_{37}N_5O_2S$, mp 157–159.5° C. FABMS: MH$^+$ 532 (51%).

Example 29

2-[6-(3-methyl-2-pyridinyl)-1,7-naphthyridin-8-y]-N-(phenylsulfonyl)hydrazine carboxamide

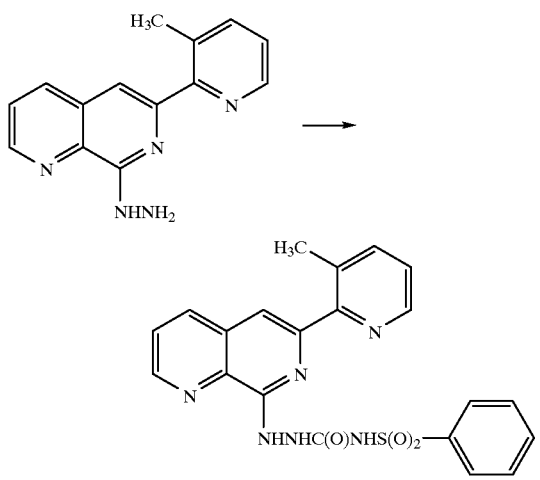

To a stirred solution of 8-hydrazino-6-(3-methyl-2-pyridinyl)-1,7-naphthyridine (162 mg, 0.645 mmol) in dichloromethane (2.5 mL) under an argon atmosphere, add benzenesulfonyl isocyanate (0.0905 mL, 124 mg, 0.678 mmol) in one portion via syringe and stir the resultant suspension at room temperature for 23 hours. Dilute the reaction mixture with diethyl ether (3.5 mL) and filter. Triturate the isolated solid in dichloromethane (4 mL)-diethyl ether (3 mL), filter, and dry under vacuum to obtain the title compound, $C_{21}H_{18}N_6O_3S$, mp 162.5–163.5° C. (dec). FABMS: MH$^+$ 435 (100%).

Example 30

4-Acetylamino-2-[6-(3-methyl-2-pyridinyl)-1,7-naphthyridin-8-yl]benzenesulfonic acid hydrazide

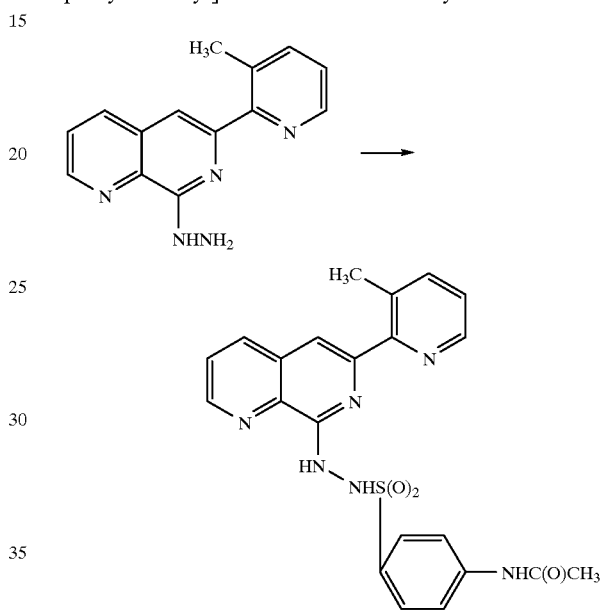

To a stirred solution of 8-hydrazino-6-(3-methyl-2-pyridinyl)-1,7-naphthyridine (162 mg, 0.645 mmol) in dichloromethane (5 mL) under an argon atmosphere, add successively 4-N,N-dimethylaminopyridine (5 mg), N-acetylsulfanilyl chloride (205 mg, 0.876 mmol) and triethylamine (0.122 mL, 88.4 mg, 0.876 mmol) and stir the resultant mixture at room temperature for 47 hours. Dilute the reaction mixture with diethyl ether 2.5 mL), stir for 5 minutes and filter. Triturate the isolated solid in water (4.5 mL), filter, wash successively with diethyl ether-acetone (85:15), then pure diethyl ether and dry under vacuum to obtain the title compound, $C_{22}H_{20}N_6O_3S \cdot H_2O$, mp 166–168° C. (dec). FABMS: MH$^+$ 449 (100%).

Example 31

N-[[[6-(3-methyl-2-pyridinyl)-1,7-naphthyridin-8-yl]amino]carbonyl]benzenesulfonamide

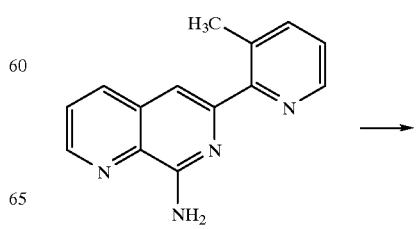

-continued

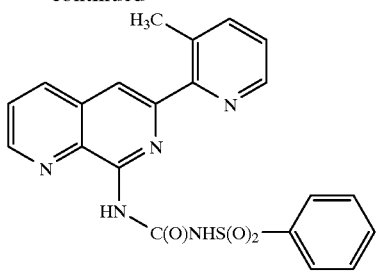

To a stirred solution of 8-amino-6-(3-methyl-2-pyridinyl)-1,7-naphthyridine (560 mg, 2.37 mmol) in dichloromethane (12 mL) under an argon atmosphere, add benzenesulfonyl isocyanate (0.334 mL, 458 mg, 0.876 mmol) and stir the resultant mixture at room temperature for 19 hours. Dilute the reaction mixture with diethyl ether (12 mL), triturate the precipitate for 10 minutes and filter. Wash the isolated solid with diethyl ether and dry under vacuum to obtain the title compound, $C_{21}H_{17}N_5O_3S$, mp 212–215° C. (dec). FABMS: MH$^+$ 420 (61%).

Example 33
3-[[4-[[[6-(3-methyl-2-pyridinyl)-1,7-naphthyridin-8-yl]amino]sulfonyl]-phenyl]amino]-3-oxopropanoic acid Heat a stirred suspension of ethyl 3-[[4-[[[6-(3-methyl-2-pyridinyl)-1,7-naphthyridin-8-yl]amino]sulfonyl]-phenyl]amino]-3-oxopropanoate (387 mg, 0.765 mmol) in 0.125 N aqueous sodium hydroxide solution at 60° C. for 2 hours. Allow the reaction solution to cool to room temperature, and adjust the pH of the solution to 4–5 by the dropwise addition of glacial acetic acid. Dilute with water (50 mL) and filter. Triturate the isolate solid with methanol (1.5 mL), dilute with water (50 mL), filter and vacuum dry to obtain the title compound as a monohydrate, $C_{23}H_{19}N_5O_5S \cdot H_2O$, mp 163–164° C. (dec). FABMS: MH$^+$ 478 (100%).

Add 18.86 mL of 0.100 N aqueous sodium hydroxide solution to a stirred suspension of the title compound (459 mg, 0.943 mmol) in water (100 mL). Lyophilize the resultant solution, triturate the residue with diethyl ether, filter and dry under vacuum to obtain the disodium salt of the title compound as a dihydrate, $C_{23}H_{17}N_5O_5SNa_2 \cdot 2H_2O$, mp 305° C. (decomposition with foaming). FABMS: MH$^+$ 478 (16%); MNa$^+$ 500 (17%).

As used throughout the specification, "dec" means decomposition

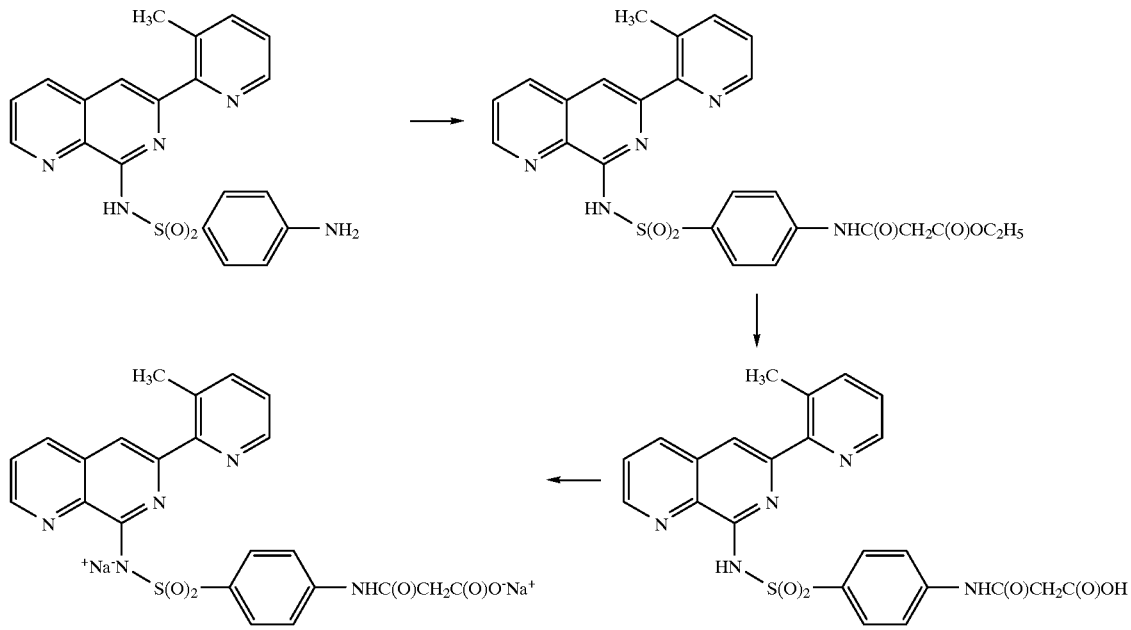

Example 32
Ethyl 3-[[4-[[[6-(3-methyl-2-pyridinyl)-1,7-naphthyridin-8-yl]amino]sulfonyl]-phenyl]amino]-3-oxopropanoate Add a solution of ethyl malonyl chloride (1.02 g, 6.77 mmol) in dichloromethane (5 mL) to a stirred suspension of 8-(p-aminobenzenesulfonamido)-6-(3-methyl-2-pyridinyl)-1,7-naphthyridine (2.56 g, 6.55 mmol), triethylamine (1.0 mL, 7.17 mmol) and 4-dimethylaminopyridine (25 mg) in dichloromethane (45 mL). Stir at room temperature for 72 hours, then reflux for 18.5 hours. Evaporate the solvent under vacuum and replace it with 1,2-dichloroethane (50 mL). Add triethylamine (1.0 mL, 7.17 mmol) and ethyl malonyl chloride (1.02 g, 6.77 mmol), and reflux for 18 hours. Cool the reaction mixture to room temperature, filter and triturate the isolated solids with hot methanol. Cool the mixture to room temperature and filter to obtain the title compound as a dihydrate, $C_{25}H_{23}N_5O_5S \cdot 2H_2O$, mp 237.5–238° C. (dec). FABMS: MH$^+$ 506 (100%).

Example 34
N-[(4-aminophenyl)sulfonyl-N-[6-(3-methyl-2-pyridinyl)-1,7-naphthyridin-8-yl]glycine, ethyl ester

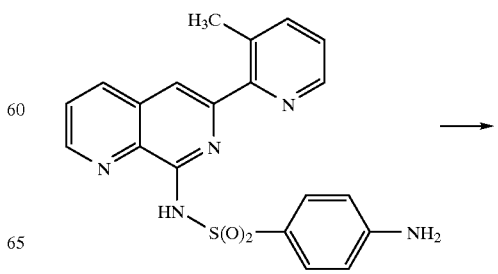

-continued

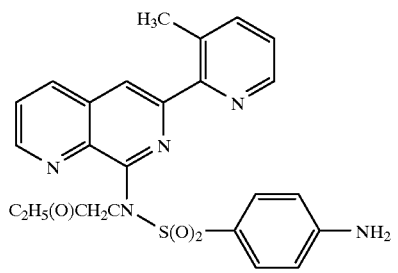

Add a dispersion of sodium hydride in mineral oil (60%; 55 mg, 1.37 mmol) to a stirred solution of 8-(p-aminobenzenesulfonamido)-6-(3-methyl-2-pyridinyl)-1,7-naphthyridine (510 mg, 1.30 mmol) in dry N,N-dimethylformamide (25 mL), stir at room temperature for 30 minutes, then add ethyl bromoacetate (0.08 mL, 0.721 mmol) and stir at room temperature for 5.5 hours. Add a second quantity of ethyl bromoacetate (0.08 mL, 0.721 mmol) and stir for 18 hours at room temperature. Evaporate the mixture at 50° C. under reduced pressure, triturate with ethyl acetate and filter off unchanged starting material. Flash chromatograph the filtrate on silica gel, eluting with a stepped gradient of ethyl acetate to ethyl acetate-methanol (98:2). Triturate the isolated product with diethyl ether, filter and vacuum dry the solids to obtain the title compound, $C_{24}H_{23}N_5O_4S$, mp 170–173° C. (dec). FABMS: MH$^+$ 478 (100%).

Example 35
N-[(4-aminosulfonyl)phenyl-N'-[6-(3-methyl-2-pyridinyl)-1,7-naphthyridin-8-yl]urea Add a suspension of 4-chlorosulfonylphenyl isocyanate (162 mg, 0.743 mmol) in dry dichloromethane (2 mL) to a stirred solution of 8-amino-6-(3-methyl-2-pyridinyl)-1,7-naphthyridine (160 mg, 0.675 mmol) and triethylamine (0.10 mL, 0.743 mmol) in dichloromethane (5 mL) at 4–6° C. Stir at 5–15° C. for 1 hour, then at room temperature for 23 hours. Add a second portion of the isocyanate (16 mg, 0.074 mmol) and stir for another 24 hours at room temperature. Evaporate the reaction mixture under vacuum, and dissolve the residue (251 mg, 0.553 mmol) in dichloromethane (12 mL). Add a saturated solution of ammonia in methanol (3.4 mL), stir for 20 minutes at room temperature, then evaporate the mixture under reduced pressure. Flash chromatograph the residue on silica gel, eluting with a stepped gradient of dichloromethane-methanol-ammonium hydroxide (95:5:0.1→90:9:0.1) to obtain the title compound, $C_{21}H_{18}N_6O_3S$, mp 248.5–249.5° C. (dec). FABMS: MH$^+$ 435 (100%).

Example 36

N-[4-[[[1,2,3,4-tetrahydro-6-(3-methyl-2-pyridinyl)-1,7-naphthyridin-8-yl]amino]sulfonyl]phenyl]acetamide

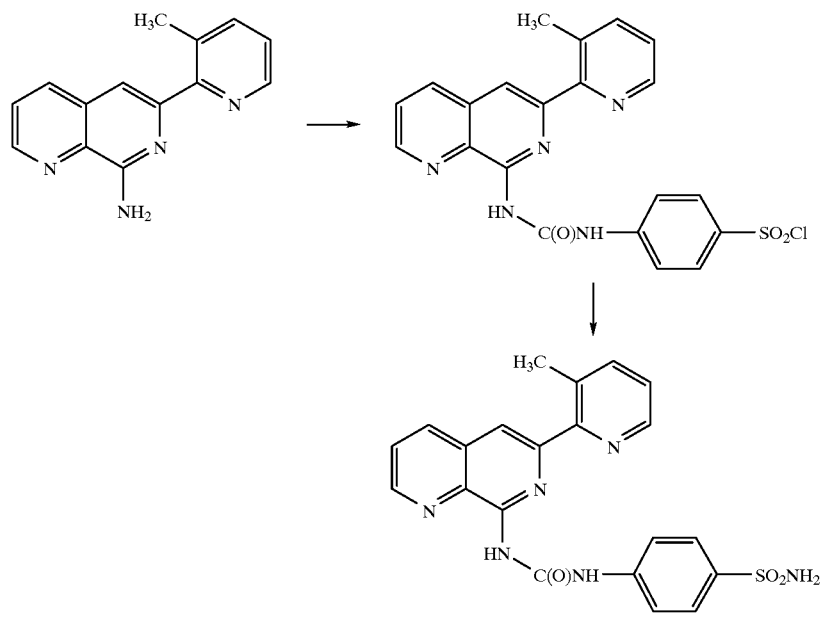

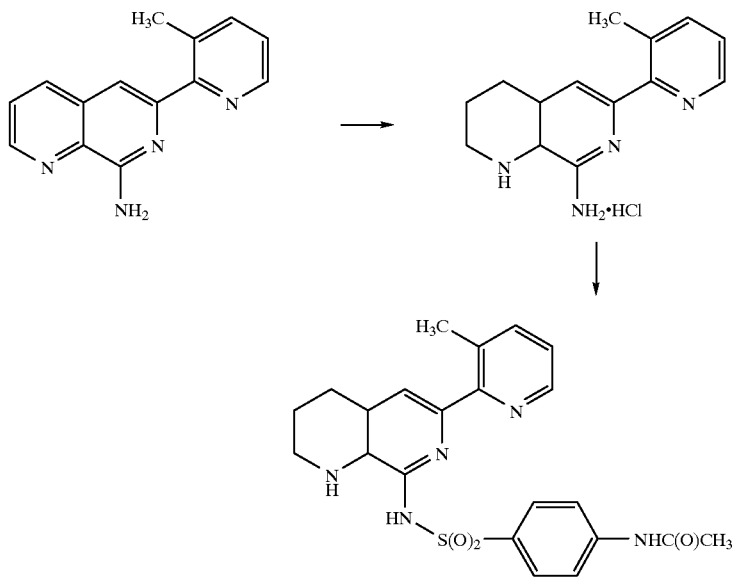

Hydrogenate a mixture of 8-amino-6-(3-methyl-2-pyridinyl)-1,7-naphthyridine (10.0 g, 0.0425 mol) and 5% palladium-on-carbon (0.52 g) in methanol (150 mL) at 50 psi for 18 hours. Acidify with 3.4 M ethereal hydrochloric acid (12.5 mL, 0.0425 mol), dilute with methanol (200 mL) and continue hydrogenation for another 24 hours. Filter the reaction mixture through Celite, evaporate the filtrate under reduced pressure and triturate the residue in diethyl ether (450 mL). Filter and crystallize the isolated solids to obtain the hydrochloride salt of 8-amino-1,2,3,4-tetrahydro-6-(3-methyl-2-pyridinyl)-1,7-naphthyridine as a 0.1 ethanolate, $C_{14}H_{16}N_4$, mp 255–257° C. (dec). CIMS: $MH^+$ 241 (100%).

Treat a solution of 8-amino-1,2,3,4-tetrahydro-6-(3-methyl-2-pyridinyl)-1,7-naphthyridine hydrochloride (1.06 g, 3.83 mmol), triethylamine (1.1 mL, 7.66 mmol) and 4-dimethylaminopyridine (47 mg) in dichloromethane (50 mL) with 4-acetylsulfanilyl chloride (984 mg, 4.21 mmol) and stir for 3 days at room temperature. Add another quantity of 4-acetylsulfanilyl chloride (98 mg, 0.42 mmol), and stir for 4 days at room temperature. Cool the reaction mixture to 0° C., filter and crystallize the isolated solids from ethanol to obtain the title compound as a hemihydrate, $C_{22}H_{23}N_5O_3S \cdot 0.5H_2O$, mp 247–249° C. (dec). FABMS: $MH^+$ 438 (86%).

Example 37
4-amino-N-[1,2,3,4-tetrahydro-6-(3-methyl-2-pyridinyl)-1,7-naphthyridin-8-yl]benzenesulfonamide

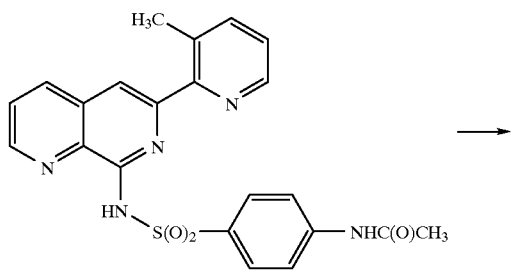

-continued

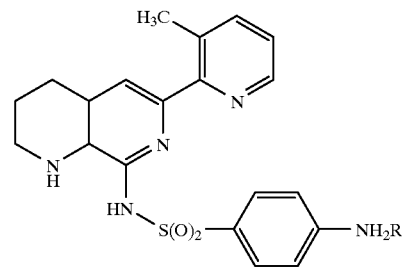

[R = —(O)CCH₃]
[R = —H]

Add 5% palladium-on-carbon to a solution of 8-(p-acetamidobenzenesulfonamido)-6-(3-methyl-2-pyridinyl)-1,7-naphthyridine (1.20 g, 2.77 mmol) and 3.4 M ethereal hydrochloric acid (0.9 mL, 3.06 mol) in methanol (50 mL). Hydrogenate at 56 psi for 20 hours, filter off the catalyst and evaporate the filtrate under reduced pressure. Stir the residue with dichloromethane (25 mL) and 1.1 M aqueous sodium bicarbonate solution (15 mL) for 18 hours. Separate the layers, wash the organic phase with water (2×20 mL), dry over anhydrous magnesium sulfate and remove solvent under reduced pressure to obtain a mixture of the title compound and N-[4-[[[1,2,3,4-tetrahydro-6-(3-methyl-2-pyridinyl)-1,7-naphthyridin-8-yl]amino]sulfonyl]phenyl]acetamide Flash chromatograph the mixture on silica gel, eluting with a stepped gradient of dichloromethane-methanol-ammonium hydroxide (98:2:0.1→95:5:0.1), and crystallize the partially purified title compound from N,N-dimethylformamide (2–2.5 mL). Filter, wash the collected solids successively with ethanol and diethyl ether and vacuum dry to obtain the title compound, $C_{20}H_{21}N_5O_2S$, mp 291–292° C. (dec). FABMS: $MH^+$ 396 (100%).

Example 38
4-[[[(diphenylmethyl)amino]carbonyl]amino]-N-[6-(3-methyl-2-pyridinyl)-1,7-naphthyridin-8-yl]benzenesulfonamide

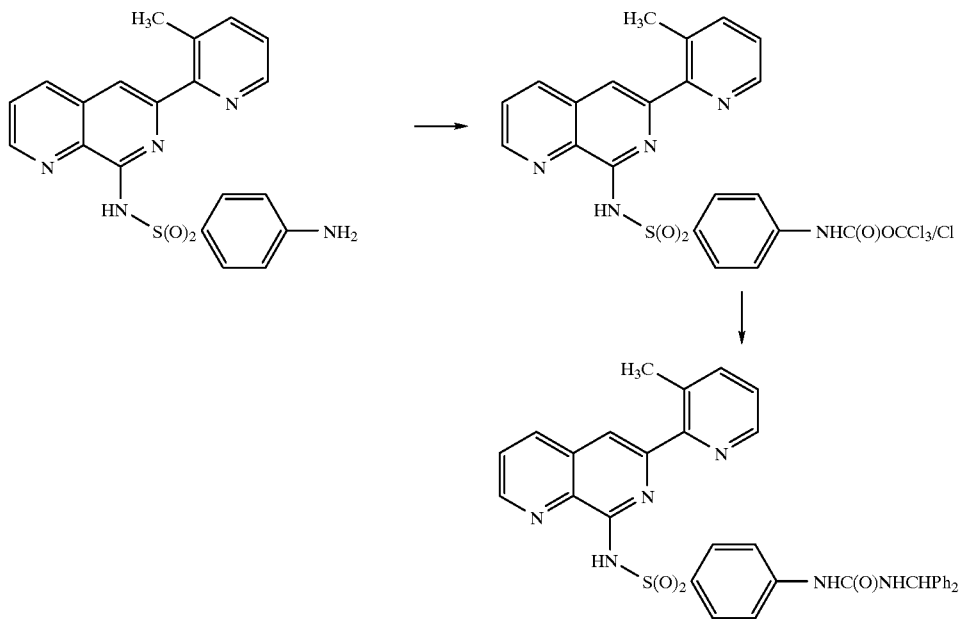

Rapidly add trichloromethylchloroformate (0.16 mL, 1.32 mmol) to a stirred suspension of 8-(p-aminobenzenesulfonamido)-6-(3-methyl-2-pyridinyl)-1,7-naphthyridine (0.43 g, 1.10 mmol), triethylamine (0.183 mL, 1.32 mmol) and 4-dimethylaminopyridine (0.03 g) in dichloromethane (25 mL) at 25° C. Stir for 1 hour at room temperature. Dilute the resultant suspension with dichloromethane (20 mL). Add aminodiphenylmethane (0.50 mL, 2.9 mmol), and stir for 3 days at room temperature. Add another quantity of aminodiphenylmethane (0.25 mL, 1.45 mmol), stir at room temperature for 2.5 hours, add triethylamine (0.61 mL, 4.4 mmol) and reflux for 24 hours. Cool the reaction mixture to room temperature, filter and wash the solids with dichloromethane. Evaporate the combined filtrate and washings under reduced pressure and flash chromatograph the residue on silica gel, eluting with dichloromethane-methanol-ammonium hydroxide (95:5:0.1). Crystallize the isolated product from N,N-dimethylformamide-water, filter, wash the solids successively with water and ethanol and vacuum dry for 18 hours at 65° C. to obtain the title compound, $C_{34}H_{28}N_6O_3S$, mp 255–256.5° C. (dec). FABMS: $MH^+$ 601 (100%).

Example 39

N-[4-[[[3-(3-methyl-4-pyridinyl)-2,6-naphthyridin-1-yl]amino]sulfonyl]phenyl]acetamide

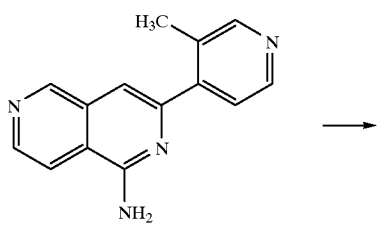

-continued

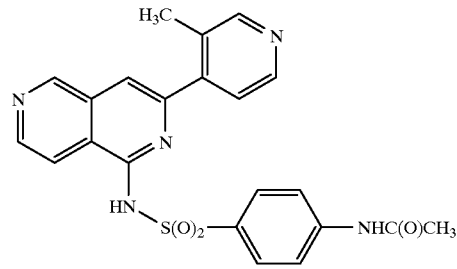

Stir a suspension of 1-amino-3-(3-methyl-4-pyridinyl)-2,6-naphthyridine (814 mg, 3.44 mmol) and N-acetylsulfanilyl chloride (885 mg, 3.79 mmol) in pyridine (25 mL) at room temperature for 20 hours. Add a second quantity of N-acetylsulfanilyl chloride (411 mg, 1.76 mmol), and stir for 24 hours at room temperature. Concentrate the reaction mixture under vacuum, and flash chromatograph the residue on silica gel, eluting with a stepped gradient of dichloromethane-methanol-ammonium hydroxide (95:5:0.1→90:9:0.1). Crystallize the isolated product from ethanol, filter and vacuum dry to obtain the title compound as a 0.25 hydrate, $C_{22}H_{19}N_5O_3S \cdot 0.25\ H_2O$, mp 244.5–245.5° C. FABMS: $MH^+$ 434 (100%).

Example 40

N-[4-[[[3-phenyl-2,7-naphthyridin-1-yl]amino]sulfonyl]phenyl]acetamide

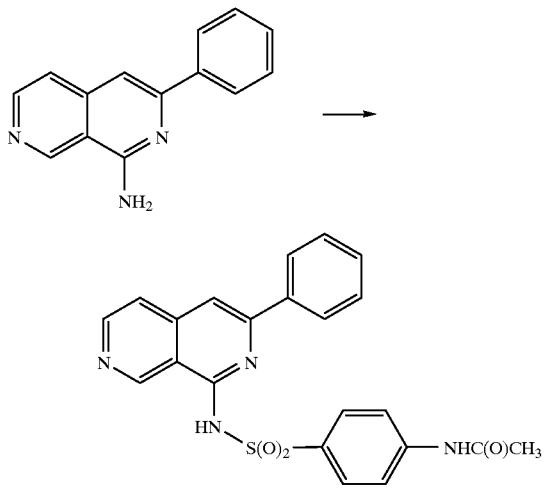

Stir a solution of 1-amino-3-phenyl-2,7-naphthyridine (756 mg, 3.42 mmol) and N-acetylsulfanilyl chloride (798 mg, 3.42 mmol) in pyridine (25 mL) at room temperature for 72 hours. Add another quantity of N-acetylsulfanilyl chloride (200 mg, 0.854 mmol), and stir at room temperature for 2.5 hours. Warm the reaction mixture to 40° C., and stir at that temperature for 7.5 hours. Concentrate the reaction mixture under vacuum, and flash chromatograph the residue on silica gel, eluting with a stepped gradient of dichloromethane-methanol-ammonium hydroxide (95:5:0.1→90:9:0.1). Reflux the isolated product in isopropyl alcohol (100 mL), filter, wash the solids with methanol and vacuum dry to obtain the title compound, $C_{22}H_{18}N_4O_3S$, mp 189.5–190.5° C. (dec). FABMS: MH$^+$ 419 (27%).

Example 41

N-[4-[[[3-(4-methyl-3-pyridinyl)-2,7-naphthyridin-1-yl]amino]sulfonyl]phenyl]acetamide Stir a suspension of 1-amino-3-(4-methyl-3-pyridinyl)-2,6-naphthyridine (929 mg, 3.93 mmol) and N-acetylsulfanilyl chloride (1.01 g, 4.32 mmol) in pyridine (22 mL) at room temperature for 24 hours. Add a second quantity of N-acetylsulfanilyl chloride (102 mg, 0.438 mmol), and stir for 72 hours at room temperature. Add a third portion of N-acetylsulfanilyl chloride (109 mg, 0.468 mmol), and stir at room temperature for 32 hours. Concentrate the reaction mixture under vacuum, partition the residue in a mixture of dichloromethane-water (25 mL/10 mL) and filter the mixture through Celite. Separate the layers of the filtrate, extract the aqueous layer with dichloromethane (2×5 mL) and dry the combined extracts over anhydrous sodium sulfate. Filter, concentrate the filtrate under reduced pressure and flash chromatograph the residue on silica gel, eluting with dichloromethane-methanol-ammonium hydroxide (90:9:0.1). Combine the product-enriched fractions, and rechromatograph, eluting with dichloromethane-methanol-ammonium hydroxide (95:5:0.1) to obtain the title compound as a 0.75 hydrate, $C_{22}H_{19}N_5O_3S \cdot 0.75\ H_2O$, mp 143.5–148.5° C. (dec). CIMS: MH$^+$ 434 (100%).

Example 42

Methyl [[2-[6-(3-methyl-2-pyridinyl)-1,7-naphthyridin-8-yl]hydrazino]sulfonyl]acetate To a stirred solution of 8-hydrazino-6-(3-methyl-2-pyridinyl)-1,7-naphthyridine (1.09 g, 4.34 mmol), triethylamine (0.67 mL, 4.81 mmol) and 4-dimethylaminopyridine (18 mg) in dichloromethane (75 mL), add a solution of methyl 2-chlorosulfonyl acetate (0.83 g, 4.81 mmol) in dichloromethane (25 mL), and stir the resultant mixture at room temperature for 23 hours. Concentrate the reaction mixture under vacuum, triturate the residue with water (50 mL), filter and flash chromatograph the solids on silica gel, eluting with dichloromethane-methanol-ammonium hydroxide (95:5:0.1) to obtain the title compound, $C_{17}H_{17}N_5O_4S$, mp 139.5–140.5° C. (dec). FABMS: MH$^+$ 388 (100%).

Example 43

4-[[2-[6-(3-methyl-2-pyridinyl)-1,7-naphthyridin-8-yl]hydrazino]sulfonyl]benzoic acid

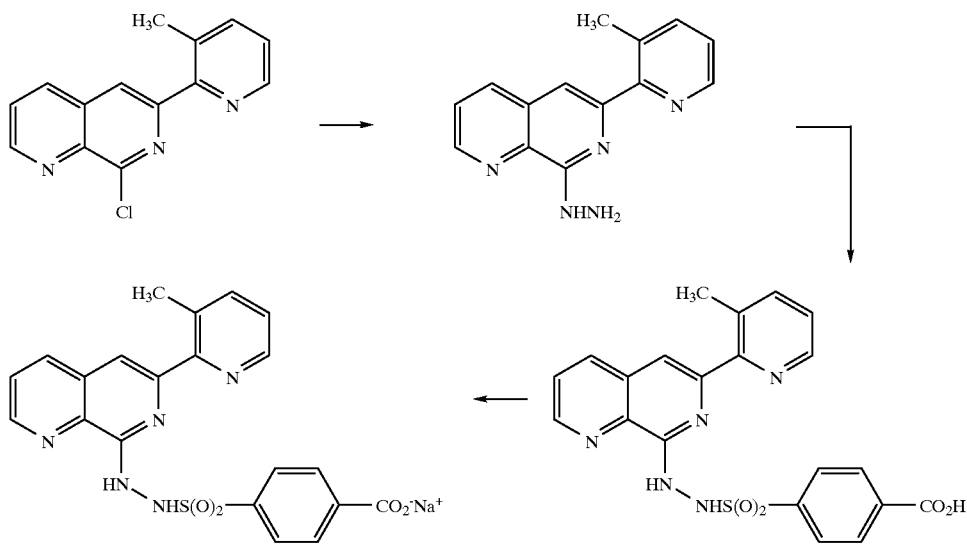

Stir a mixture of 8-hydrazino-6-(3-methyl-2-pyridinyl)-1,7-naphthyridine (257 mg, 1.02 mmol), triethylamine (0.16 mL, 1.12 mmol), 4-chlorosulfonylbenzoic acid (247 mg, 1.12 mmol) and 4-dimethylaminopyridine (24 mg) in dichloromethane (25 mL) for 24 hours at room temperature.

Filter, stir the solids with water (15 mL), refilter and flash chromatograph the isolated solids on silica gel, eluting with acetonitrile-methanol-acetic acid (4:1:0.1). Triturate the product with diethyl ether, filter and vacuum dry to obtain the free acid form of the title compound as a 0.5 hydrate, $C_{21}H_{17}N_5O_4S \cdot 0.5H_2O$. FABMS: MH$^+$ 436 (5%).

Stir a solution of free acid form of the title compound (67 mg, 0.15 mmol) and 1.5 mL of 0.100 N aqueous sodium hydroxide solution (0.15 mmol) in water (20 mL). Lyophilize, and crystallize the residue from ethanol-isopropyl ether to obtain the sodium salt form of the title compound, $C_{21}H_{16}N_5O_4SNa$, mp 217–221° C. (dec). FABMS: MH$^+$ 436; [MNa+H]$^+$ 458. HRMS: [MNa+H]$^+$ 458.0917 (found); 458.0899 (calculated).

Example 44

[[[[6-(3-methyl-2-pyridinyl)-1,7-naphthyridin-8-yl]-amino]sulfonyl]acetyl]amino]acetic acid

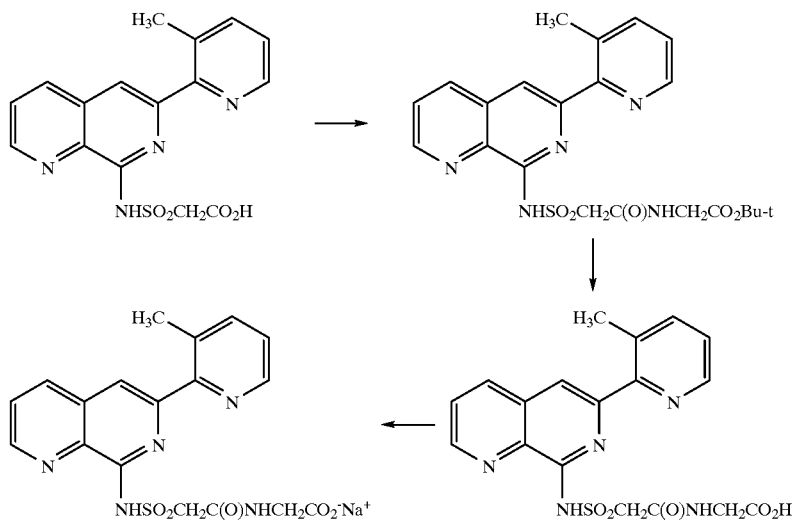

Stir a suspension of [[[6-(3-methyl-2-pyridinyl)-1,7-naphthyridin-8-yl]amino]sulfonyl]acetic acid (572 mg, 1.60 mmol) and triethylamine (0.22 mL, 1.60 mmol) in dichloromethane (50 mL) for 0.5 h. Add 1-(N,N-dimethylaminopropyl)-3-ethyl carbodiimide hydrochloride (367 mg, 1.92 mmol) and stir 48 h at room temperature. Filter to obtain the analytically pure t-butyl ester of the title carboxylic acid. Evaporate the filtrate and crystallize the residue from methanol-isopropyl ether to obtain additional t-butyl ester. FABMS: MH$^+$ 472 (100%).

Stir a solution of the t-butyl ester form of the title compound (350 mg, 0.742 mmol) in trifluoroacetic acid (6.1 mL) for 1 h at room temperature. Remove solvent under reduced pressure and triturate the residue with ethanol (20 mL) to obtain the crude title acid. Crystallize the crude acid from ethanol (25 mL), reflux the crystallized solid in diethyl ether for 30 min, cool to room temperature and filter to obtain the title compound as a 0.125 hydrate, $C_{18}H_{17}N_5O_5S$, mp 217–218° C. (dec). FABMS: $MH^+$ 416 (100%).

Add 0.100M sodium hydroxide (4.24 mL, 0.424 mmol) to a magnetically stirred suspension of the title acid (177 mg, 0.424 mmol) in water (20 mL). Lyophilize the resultant solution to obtain the analytically pure sodium salt form of the title compound as a ⅛ hydrate, $C_{18}H_{16}N_5O_5SNa \cdot 0.125H_2O$, mp ~170° C. (dec). FABMS: $MH^+$ 416 (73%); $MNa^+$ 438 (100%).

Example 45

2-[[[[[6-(3-methyl-2-pyridinyl)-1,7-naphthyridin-8-yl]-amino]sulfonyl]acetyl]amino]butanedioic acid, disodium salt Add 0.10M sodium hydroxide (9.52 mL, 0.952 mmol) to a magnetically stirred suspension of the title free acid (226 mg, 0.476 mmol) in water (50 mL). Lyophilize the resultant solution and vacuum dry the residue over phosphorus pentoxide to obtain the analytically pure disodium salt form of the title compound as a dihydrate, $C_{20}H_{17}N_5O_7SNa_2 \cdot 2H_2O$, mp ~208° C. (dec). FABMS: $MH^+$ 474 (15%); $MNa^+$ 496 (49%).

Example 46

N-[(1,1-Dimethylethoxy)carbonyl]-O-[[[[(3-methyl-2-pyridinyl)-1,7-naphthyridin-8-yl]-amino]sulfonyl]acetyl] serine phenylmethyl ester

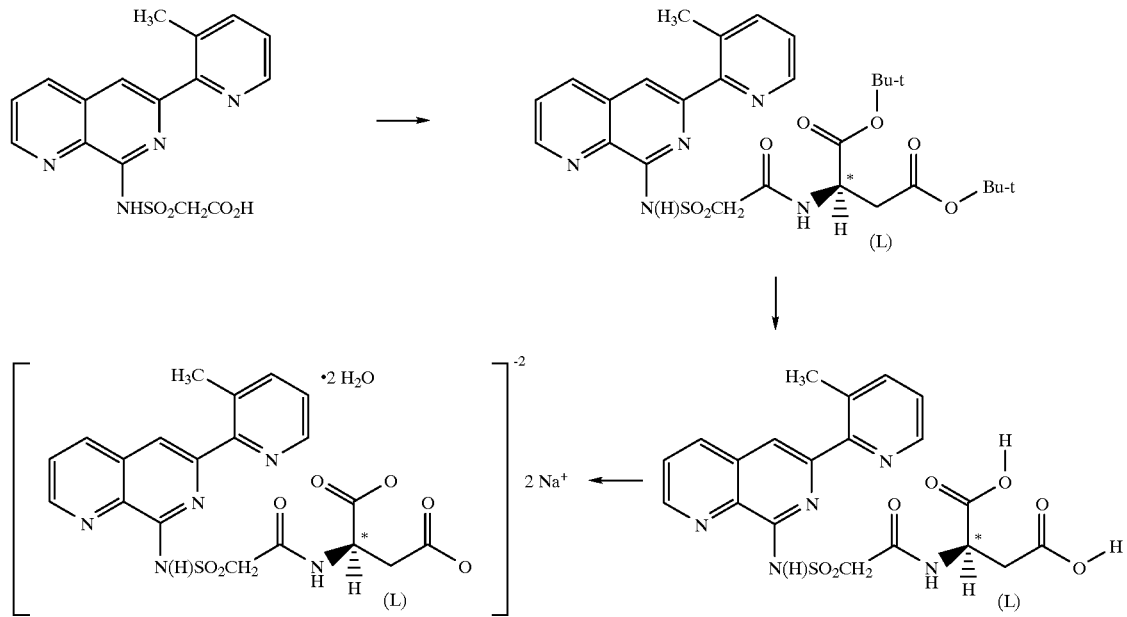

Stir a mixture of [[[6-(3-methyl-2-pyridinyl)-1,7-naphthyridin-8-yl]amino]sulfonyl]acetic acid (457 mg, 1.27 mmol), L-aspartic acid, di-t-butyl ester hydrochloride (358 mg, 1.27 mmol) and triethylamine (0.18 mL, 1.29 mmol) in dry dichloromethane (25 mL) for 10 minutes at room temperature. Add 1-(N,N-dimethylaminopropyl)-3-ethyl carbodiimide hydrochloride (293 mg, 1.53 mmol) and stir 72 h at room temperature. Remove solvent under reduced pressure, and flash chromatograph the residue, eluting with dichloromethane-methanol-concentrated ammonium hydroxide (95:5:0.1) to obtain the crude di-t-butyl ester of the title dicarboxylic acid. Dissolve the di-t-butyl ester (599 mg, 1.02 mmol) in trifluoracetic acid (2 mL) and allow the solution to stand at room temperature for 18 h. Remove solvent under reduced pressure, and partition the residue between water (5 mL) and dichloromethane (5 mL). Wash the aqueous layer successively with dichloromethane (5 mL) and diethyl ether (3 mL). Strip water from the aqueous layer under reduced pressure to obtain the crude title acid (free form). Crystallize from methanol-isopropyl ether, then reflux in methanol (25 mL), cool to room temperature and filter to obtain the analytically pure free form of the title acid, $C_{20}H_{19}N_5O_7S$, mp 207–208° C. (dec). FABMS: $MH^+$ 474 (12%).

-continued

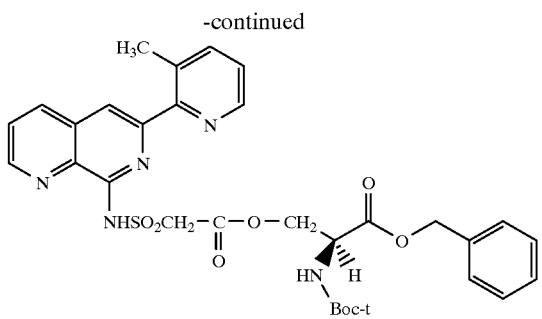

Stir a suspension of [[[6-(3-methyl-2-pyridinyl)-1,7-naphthyridin-8-yl]amino]sulfonyl]acetic acid (533 mg, 1.49 mmol), N-t-Boc-L-serine, benzyl ester (483 mg, 1.63 mmol), 1-(N,N-dimethylaminopropyl)-3-ethyl carbodiimide hydrochloride (DEC.HCl, 314 mg, 1.63 mmol) and 4-N,N-dimethylaminopyridine (21 mg) in dry dichloromethane (50 mL) for 3 days at room temperature. Reflux and add further quantities of protected serine, followed by DEC.HCl, according to the following schedule: after 7.5 h, protected serine (75 mg, 0.253 mmol), followed by DEC.HCl (48 mg, 0.253 mmol); after 23.5 h, protected serine (136 mg, 0.459 mmol), followed by DEC.HCl (88 mg, 0.456 mmol). Stir 18 h at room temperature, add another quantity of protected serine (48 mg, 0.163 mmol), followed by DEC.HCl (31 mg, 0.163 mmol), and stir at room temperature for a further 5 days. Flash chromatograph the reaction mixture on silica gel, eluting with dichloromethane-methanol-ammonium hydroxide (95:5:0.1). Rechromatograph the principal fraction on silica gel, eluting with ethyl acetate-hexanes (1:1), to obtain the title compound as a ¼ hydrate, $C_{31}H_{33}N_5O_8S \cdot 0.25H_2O$, mp 77–81.5° C. FABMS: MH$^+$ 636 (9%).

Example 47
N-[4-[[Methyl-6-(3-methylpyridin-2-yl)-1,7-naphthyridin-8-yl]-amino]sulfonyl]phenyl]acetamide

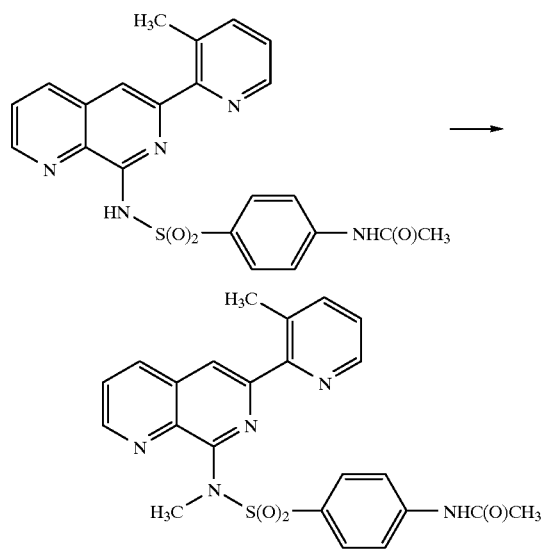

Add 60% sodium hydride-mineral oil dispersion (85.4 mg, 2.14 mmol) to a stirred suspension of N-[4-[[[6-(3-methyl-2-pyridinyl)-1,7-naphthyridin-8-yl]amino]sulfonyl] phenyl]acetamide (841 mg, 1.94 mmol) in dry N,N-dimethylformamide (19 mL). Stir at room temperature for 20 minutes. Add iodomethane (303 mg, 2.13 mmol) and stir at room temperature for 21 hours. Add a second portion of iodomethane (83 mg, 0.582 mmol), stir for 5 hours at room temperature, and remove solvent under reduced pressure. Flash chromatograph the gummy residue on silica gel, eluting with a stepped gradient of dichloromethane-methanol-ammonium hydroxide (98:2:0.125→95:5:0.125) to obtain the title compound, $C_{23}H_{21}N_5O_3S$, mp 227–228.5° C. FABMS: MH$^+$ 448 (34%).

Example 48
N-[4-[[[6-(3-methylpyridin-2-yl)-1,7-naphthyridin-8-yl]-amino]sulfonyl]phenyl]acetamide-N'N-oxide

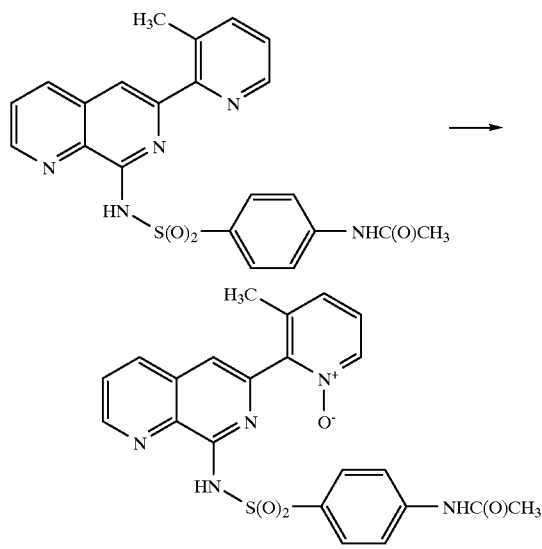

Reflux a stirred suspension of N-[4-[[[6-(3-methyl-2-pyridinyl)-1,7-naphthyridin-8-yl]amino]sulfonyl]phenyl] acetamide (1.09 g, 2.51 mmol) and 80–85% m-chloroperoxybenzoic acid (m-CPBA; 600 mg, 2.87 mmol) in dry dichloromethane (325 mL) for 46 hours. Add three additional portions of m-CPBA as follows: after 10 hours, 30 mg (0.146 mmol); after 26 hours, 120 mg (0.574 mmol); after 42 hours, 86 mg (0.412 mmol). Cool the reaction mixture to room temperature, wash it successively with 10% sodium bisulfite solution (100 mL) and water (2×50 mL), and dry over anhydrous sodium sulfate. Filter out drying agent, remove solvent in vacuo, and flash chromatograph the residue on silica gel, eluting with dichloromethane-methanol-ammonium hydroxide (80:18:0.25) to obtain the title compound, $C_{22}H_{19}N_5O_4S$, mp 230–231.5° C. (dec). FABMS: MH$^+$ 450 (100%).

Example 49
N-[4-[[[6-(3-methylpyridin-2-yl)-1,7-naphthyridin-8-yl]-amino]sulfinyl]phenyl]acetamide

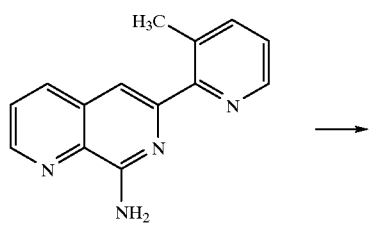

-continued

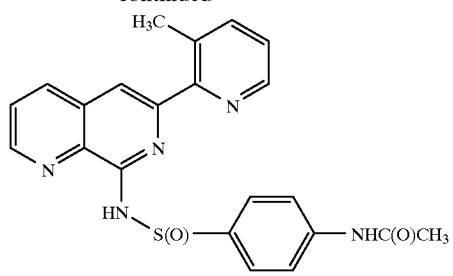

Add successively 4-(acetylamino)benzenesulfinyl chloride (974 mg, 4.48 mmol) and 4-N,N-dimethylaminopyridine (DMAP; 50 mg, 0.410 mol) to a stirred solution of 8-amino-6-(3-methyl-2-pyridinyl)-1,7-naphthyridine (962 mg, 4.07 mol) and triethylamine (453 mg, 4.48 mmol) in dry dichloromethane (28 mL) at room temperature. Stir the reaction mixture for 2 hours at room temperature, reflux for 20 hours, then allow it to cool to room temperature. Add another portion each of triethylamine (114 mg, 1.12 mmol) and 4-(acetylamino)benzenesulfinyl chloride (244 mg, 1.12 mmol), and stir at room temperature for 18.5 hours. Add third portions of triethylamine (57 mg, 0.56 mmol) and 4-(acetylamino)benzenesulfinyl chloride (122 mg, 0.56 mmol), respectively, and stir at room temperature for 4 days. Dilute the reaction mixture with water (10 mL), separate the layers, and wash the organic phase with water (2×10 mL). Dry the organic phase over anhydrous magnesium sulfate. Filter out drying agent, remove solvent in vacuo, and flash chromatograph the residue on silica gel, eluting with dichloromethane-methanol-ammonium hydroxide (90:9:0.125) to obtain the title compound, $C_{22}H_{19}N_5O_2S$, mp 206–207° C. (dec). FABMS: MH$^+$ 418 (67%).

Example 50
N-[6-(3-methyl-2-pyridinyl)-1,7-naphthyridin-8-yl]-4-[(2-phenylethyl)amino]benzenesulfonamide

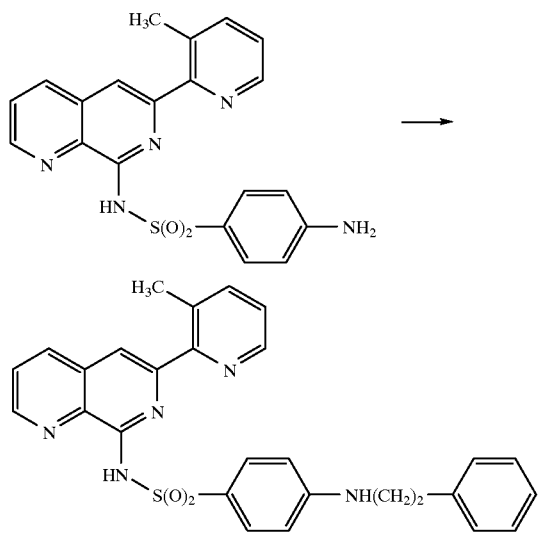

Prepare an intimate mixture of 8-(p-aminobenzenesulfonamido)-6-(3-methyl-2-pyridinyl)-1,7-naphthyridine (590 mg, 1.51 mmol) and tetrabutylammonium bromide (4.28 g), transfer the mixture to round-bottomed flask, add 2-bromoethylbenzene (0.23 mL, 1.66 mmol) and heat in an oil bath at 115° C. for 3 hours. Add diisopropylethylamine (0.30 mL, 1.72 mmol) and heat for an additional 2 hours at 115° C. Cool the mixture to room temperature, and triturate the residue with water (2×25 mL). Filter and flash chromatograph the isolated solid on silica gel, eluting with dichloromethane-methanol-ammonium hydroxide (98:2:0.1) to obtain the title compound, $C_{28}H_{25}N_5O_2S$, mp 152–153.5° C. FABMS: MH$^+$ 496 (100%).

Example 51
2-(2-Methoxyethoxy)ethyl [[[6-(3-methyl-2-pyridinyl)-1,7-naphthyridin-8-yl]amino]sulfonyl]acetate

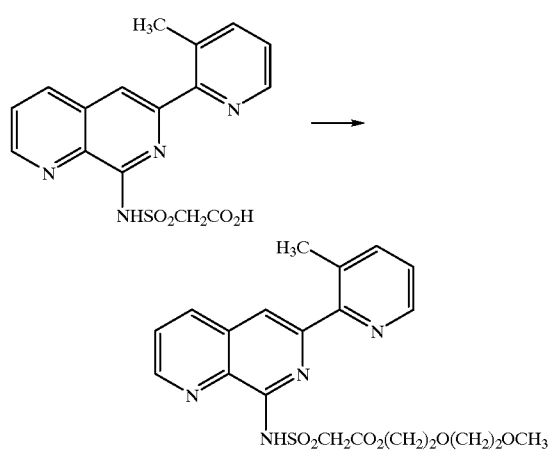

Heat at 80° C. for 2 hours a solution of [[[6-(3-methyl-2-pyridinyl)-1,7-naphthyridin-8-yl]amino]sulfonyl]acetic acid (660 mg, 1.84 mmol) in 2-(2-methoxyethoxy)ethanol (15 mL) containing concentrated sulfuric acid (0.5 mL). Concentrate the reaction solution at 75–80° C. under reduced pressure (1–2 Torr) to a volume of approximately 3 mL. Dissolve this concentrate in dichloromethane (15 mL) and neutralize by washing the solution with saturated aqueous sodium carbonate solution. Separate and wash the organic layer with water (3×5 mL), dry over anhydrous sodium sulfate, filter out the drying agent and evaporate the filtrate under vacuum. Flash chromatograph the residue on silica gel, eluting with dichloromethane-methanol-ammonium hydroxide (90:9:0.1) to obtain the title compound as a viscous oil. Triturate this oil successively with hexanes, then isopropyl ether (5 mL), to obtain the title compound as a solid, $C_{21}H_{24}N_4O_6S$, mp 89.5–92° C. (dec). FABMS: MH$^+$ 461 (46%).

Example 52
N-Hydroxy-2-[[[6-(3-methyl-2-pyridinyl)-1,7-naphthyridin-8-yl]amino]sulfonyl]acetamide

NHSO₂CH₂C(O)NHOH

↓

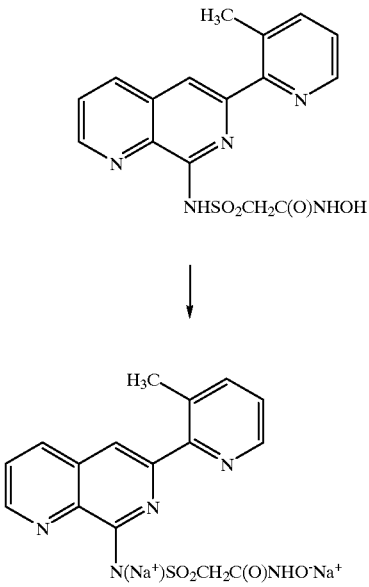

N(Na⁺)SO₂CH₂C(O)NHO⁻Na⁺

Stir a solution of [[[6-(3-methyl-2-pyridinyl)-1,7-naphthyridin-8-yl]amino]sulfonyl]acetic acid, methyl ester (252 mg, 0.675 mmol), hydroxylamine hydrochloride (235 mg, 3.38 mmol) and triethylamine (1.03 g, 10.1 mmol) in water (40 mL) at room temperature for 42 hours. Remove water at ≦50° C. under vacuum, stir the residue with dichloromethane (50 mL) and filter. Reflux the isolated solid in methanol (100 mL) for 2 hours, cool to room temperature, and filter to obtain the title compound in its free acid form as a 1.75 hydrate, $C_{16}H_{15}N_5O_4S \cdot 1.75 H_2O$, mp 168.5–169° C. (dec). FABMS: MH⁺ 374 (5%).

To a stirred suspension of the title acid (76 mg, 0.202 mmol) in water (5 mL) add 0.100 N sodium hydroxide solution (4.04 mL, 4.04 mmol). Remove water from the resultant solution by azeotroping with ethanol at 55° C. under reduced pressure. Triturate the residue with diethyl ether and filter to obtain the title compound in its disodium salt form, $C_{16}H_{13}N_5O_4SNa_2$, mp 217–218.5° C. (dec). FABMS: MH⁺ 418 (85%) for 2Na⁺ salt.

Example 53

2-[[[[[6-(3-methyl-2-pyridinyl)-1,7-naphthyridin-8-yl]amino]sulfonyl]acetyl]amino]ethanesulfonic acid, sodium salt

NHSO₂CH₂CO₂H

→

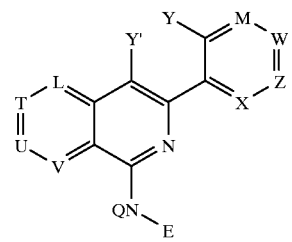

NHSO₂CH₂C(O)NH(CH₂)₂SO₃⁻Na⁺

To a stirred solution (cloudy) of [[[6-(3-methyl-2-pyridinyl)-1,7-naphthyridin-8-yl]amino]sulfonyl]acetic acid (409 mg, 1.14 mmol) in N,N-dimethylformamide (25 mL) add successively 1-(3-N,N-dimethylaminopropyl)-3-ethylcarbodiimide hydrochloride (DEC.HCl; 328 mg, 1.71 mmol) and the sodium salt of taurine (168 mg, 1.14 mmol; prepared from the acid by treatment with an equivalent of aqueous sodium hydroxide and removal of water by lyophilization). Stir the reaction mixture at room temperature for 4 hours. Remove solvent under reduced pressure, stir the residual gum with methanol (2 mL), dilute with ether (25 mL), and decant the supernatant. Triturate the residue with diethyl ether (25 mL) and decant. Dissolve the residue in water (15 mL), wash with dichloromethane (4×5 mL) and remove solvent at 55–60° C. under reduced pressure. Crystallize the residue from methanol-acetonitrile. Flash chromatograph the partially purified solid on silica gel, eluting with acetonitrile-acetic acid-water in a stepped gradient (50:1:1→20:1:1→10:1:1→5:1:1). Crystallize the main fraction from methanol (30 mL) to obtain the title compound as a 1.25 hydrate, $C_{18}H_{18}N_5O_6S_2Na \cdot 1.25 H_2O$, mp 256.5–258° C. (dec). FABMS: MH⁺ 466 (47%), MNa⁺ 488 (69%).

What is claimed is:

1. A compound of the formula:

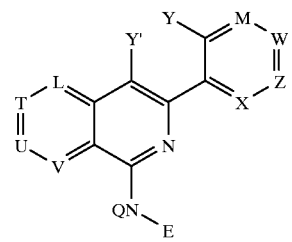

wherein E is

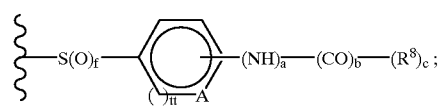

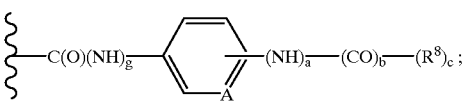

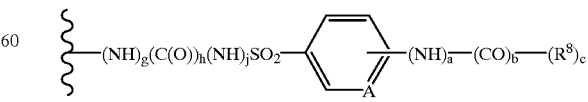

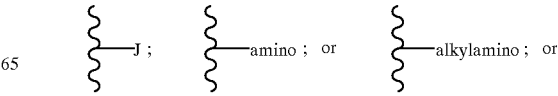

-continued $$-N=\underset{H}{C}-WW,$$

wherein WW is aryl or heteroaryl; and
wherein A is CH, S, N or N→O wherein L, T, U and V are each independently CH, N or N→O, with the proviso that only one of said L, T, U and V can be N or N→O;

wherein M, X, Z and W are each independently CH, N or N→O, with the proviso that only one of said M, X, Z and W can be N or N→O;

Y is H or —CH$_3$;

Y' is H, lower alkyl, phenyl, phenyl-lower alkyl;

Q is H, lower alkyl O(O)CCH$_2$—, lower alkyl, or lower alkyl (O)C—, a, b, c, g, h, and j is each independently 0 or 1;

f is 1 or 2;

n is 1 to 6;

tt is 0 or 1;

R$^8$ is H, OH, halo when a and b are both 0, C$_1$–C$_{10}$ alkyl, C$_1$–C$_6$ alkoxy, —OCH$_2$Ph, —CH$_2$Ph, —CH$_2$CH$_2$Ph, cyclohexyl, CH$_2$C(O)OC$_2$H$_5$; —O(CH$_2$)$_2$O—(CH$_2$)$_2$OCH$_3$, —CO$_2$H when a and b are both 0; NHCH$_2$Ph, NH(CO)CH$_3$, —NH$_2$, —OH when a is 0, aryl, —CH$_2$C(O)OH, —CH$_2$C(O)ONa,

[structures: CHPh$_2$ and N(CH$_3$)HCHPh$_2$]

or —SO$_2$NH$_2$
phenyl, substituted phenyl,
when a and b are both 0;

J is SO$_2$CH$_2$CONH(CH$_2$)$_2$SO$_3^-$Na$^+$, —SO$_2$CH$_2$Ph, —SO$_2$CH$_2$C(O)NHOH, —SO$_2$CH$_2$CO$_2$H, —SO$_2$CH$_2$CO$_2$Na, —SO$_2$CH$_2$CO$_2$(CH$_2$)$_2$O(CH$_2$)$_2$OCH$_3$, —SO$_2$(CH$_2$)$_2$CH$_3$, —S(O)$_2$CH$_2$CO$_2$CH$_3$, —S(O)$_2$CH$_2$C(O)NHCH$_2$C(O)OH, SO$_2$CH$_3$, —S(O)$_2$CH$_2$C(O)NHCH$_2$C(O)Na, —S(O)$_2$CH$_2$C(O)NH(CH$_2$)$_2$SO$_3$Na, —S(O)$_2$CH$_2$CO$_2$Na, —SO$_2$CH$_2$CH$_2$OH, —SO$_2$(CH$_2$)$_n$C(O)-amino acid, —SO$_2$(CH$_2$)$_n$C(O)-protected amino acid; —SO$_2$(CH$_2$)$_n$ X'; wherein X' is an ester or an amide and n is 1 to 6;

or a pharmaceutically acceptable salt thereof.

2. A compound according to claim 1 wherein E is

[structure: —S(O)$_f$—phenyl(A)—(NH)$_a$—(CO)$_b$—(R$^8$)$_c$]

3. A compound according to claim 1 wherein E is

[structure: —C(O)(NH)$_g$—phenyl(A)—(NH)$_a$—(CO)$_b$—(R$^8$)$_c$]

4. A compound according to claim 1

[structure: —(NH)$_g$(C(O))$_h$(NH)$_j$SO$_2$—phenyl(A)—(NH)$_a$—(CO)$_b$—(R$^8$)$_c$]

5. A compound according to claim 1 wherein E is

—J ; —amino ; —alkylamino ; or —N=C(H)—WW, wherein WW is aryl or heteroaryl.

6. A compound according to claim 1 of the formula

I'

[structure of 3-(3-methylpyridin-2-yl)-1,7-naphthyridine with HN—S(O)$_2$—phenyl—(NH)$_a$—(CO)$_b$—R$^8$]

wherein a is 0 or 1;
b is 0 or 1; and
R$^8$ is C$_1$–C$_6$ alkyl, C$_1$–C$_6$ alkoxy, —OCH$_2$Ph, or —CH$_2$Ph, or a pharmaceutically acceptable salt thereof.

7. A compound according to claim 6 wherein a is 1, b is 1, and R$^8$ is —CH$_3$.

8. A compound according to claim 6 wherein R$^8$ is —C$_1$–C$_6$ alkyl.

9. A compound according to claim 6 wherein R$^8$ is —OCH$_2$Ph.

10. A compound according to claim 6 wherein R$^8$ is —CH$_2$Ph.

11. A compound according to claim 1 selected from the group consisting of

[structure with HN—SO$_2$—CH$_2$CO$_2$H]

or the sodium salt of the carboxylic acid;

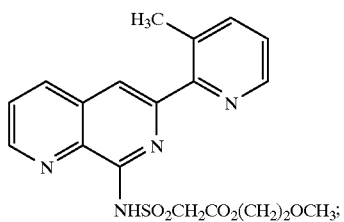
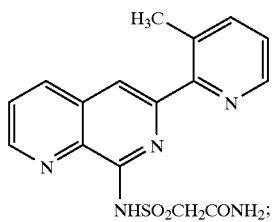
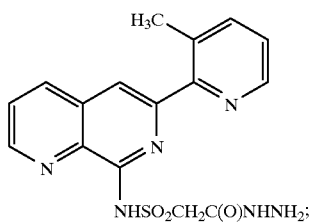
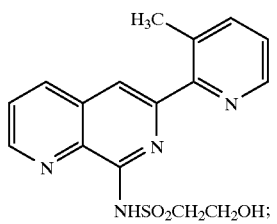
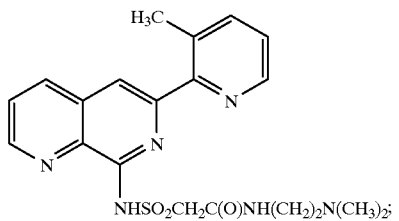
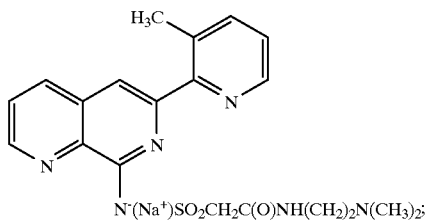
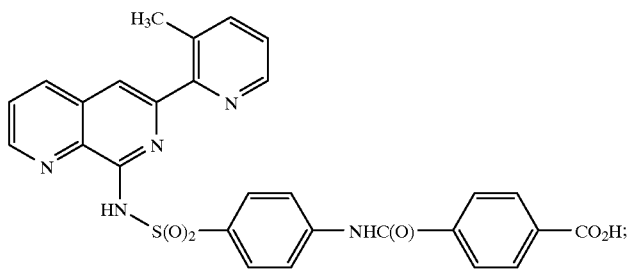

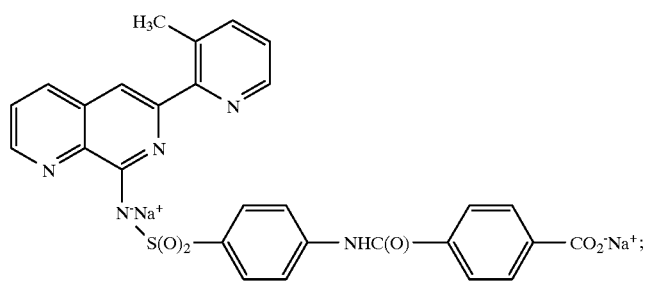
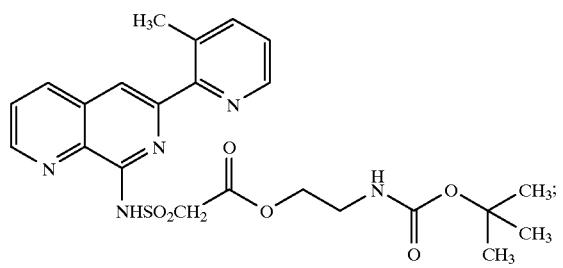
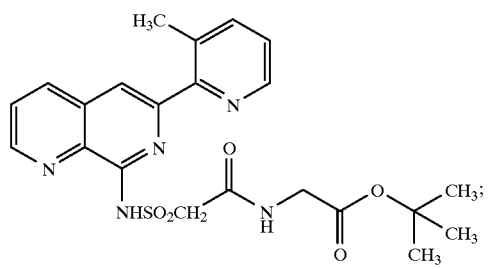
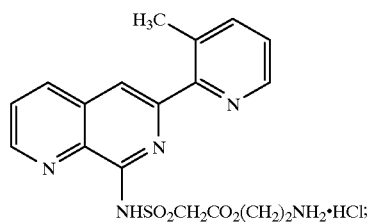
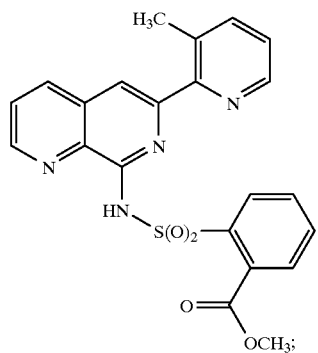

-continued
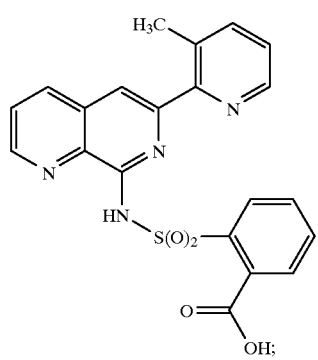
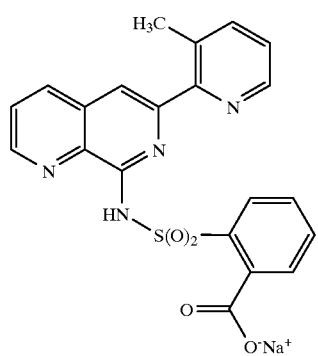
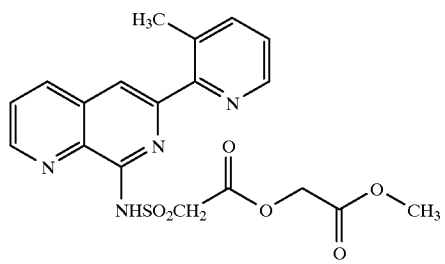
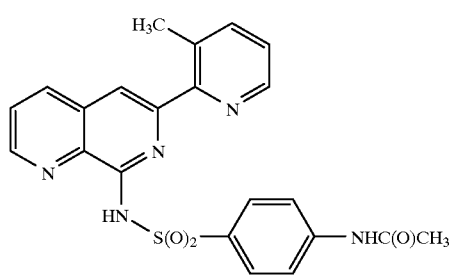
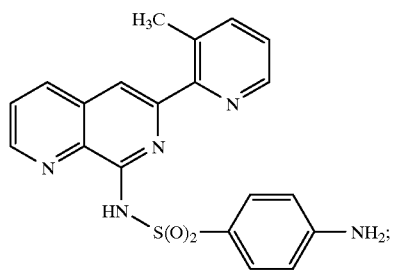

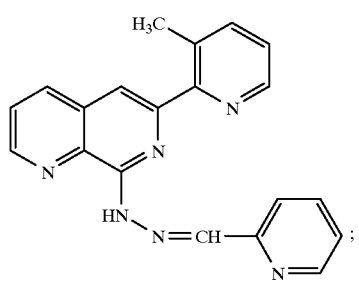
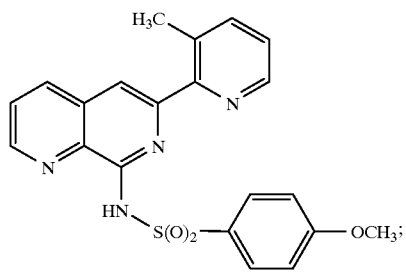
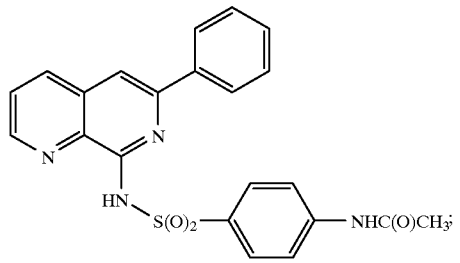
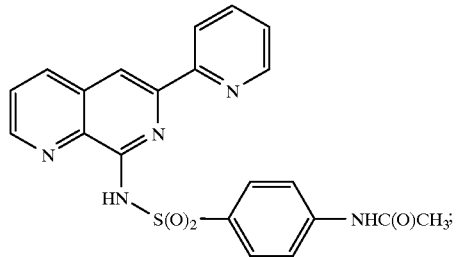
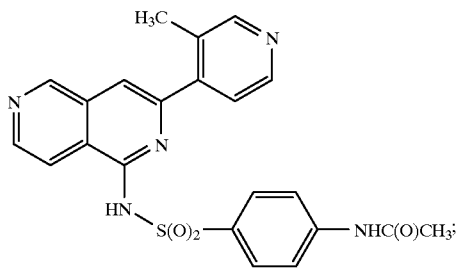
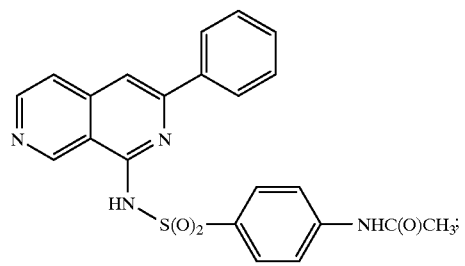

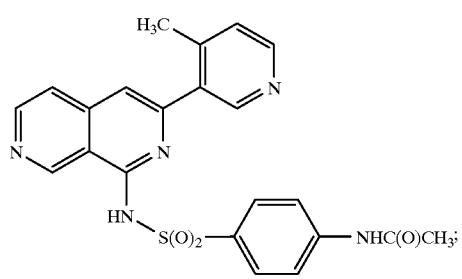
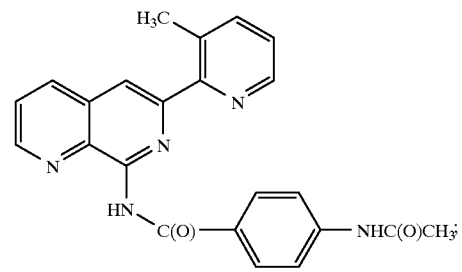
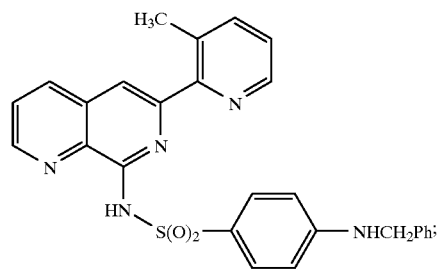
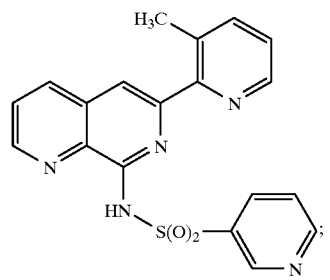
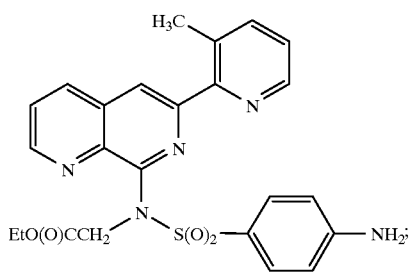
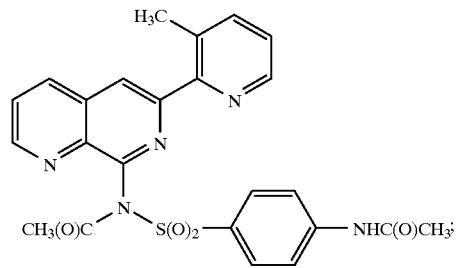

-continued
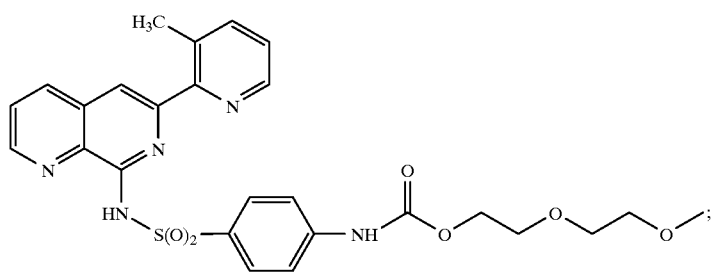
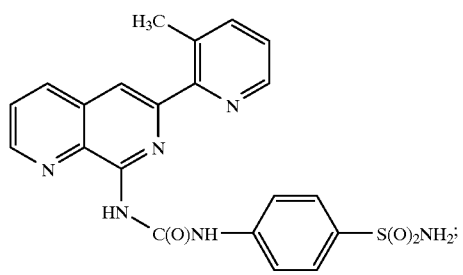
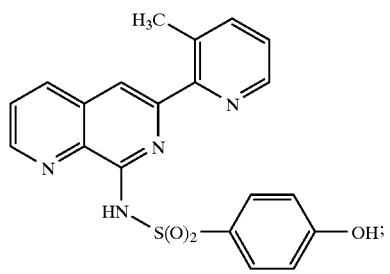
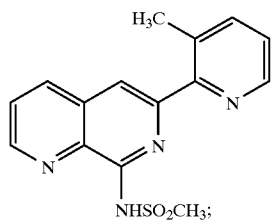
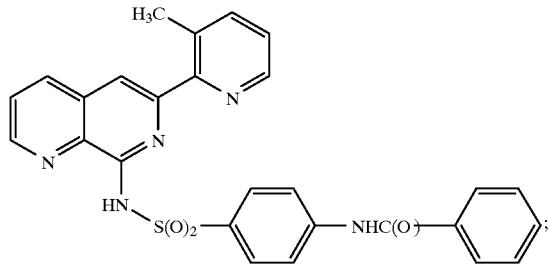
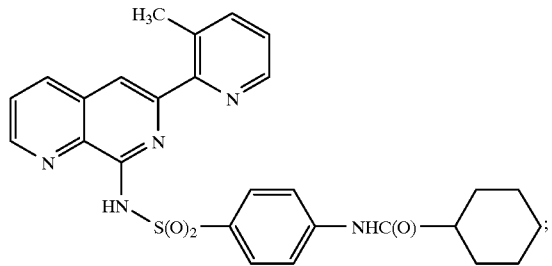

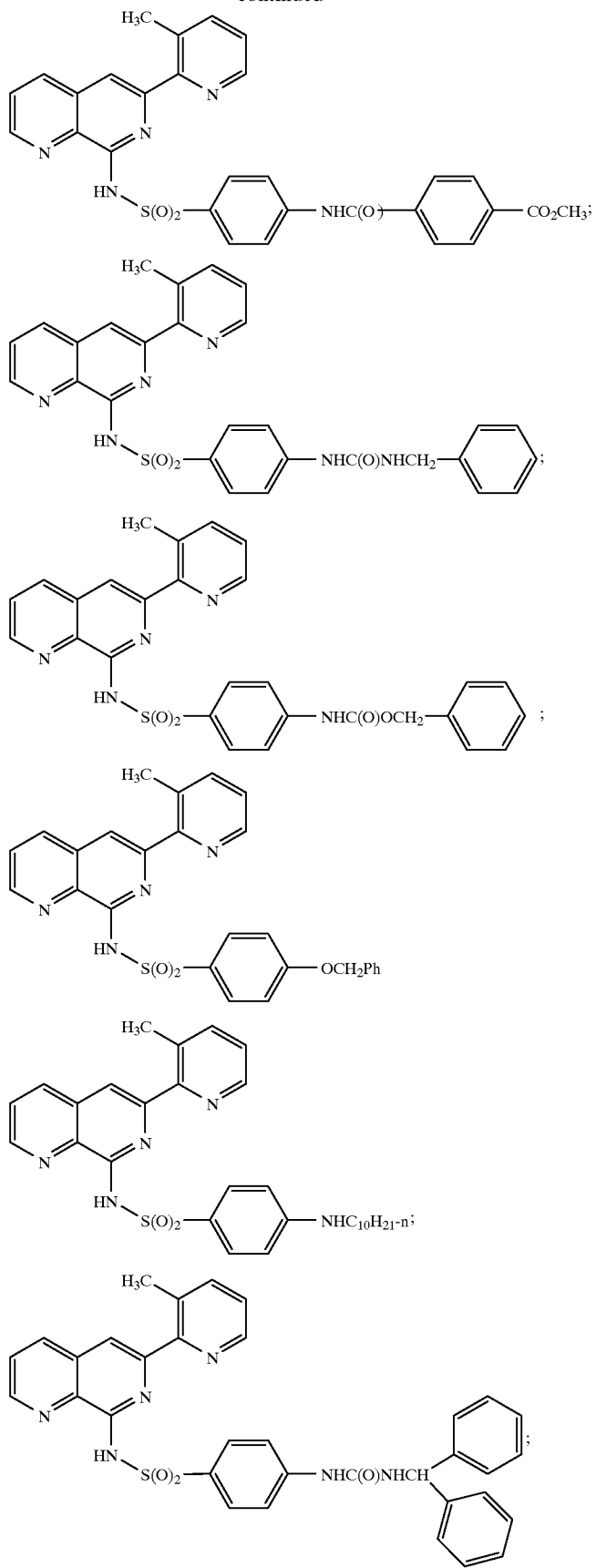

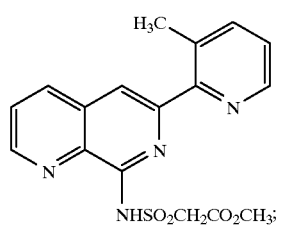
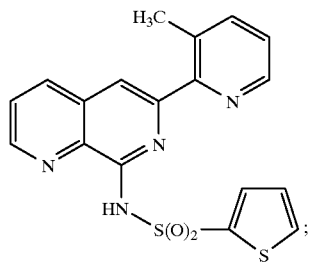
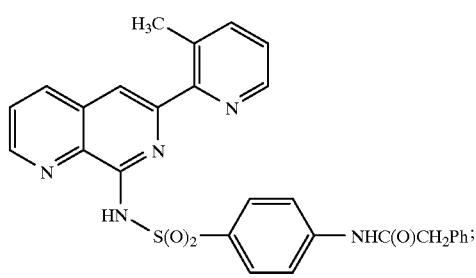
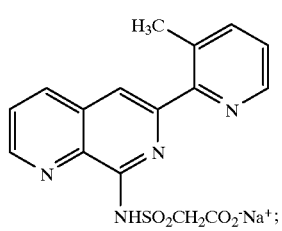
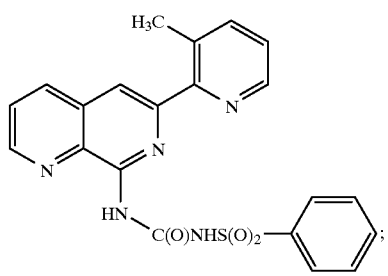
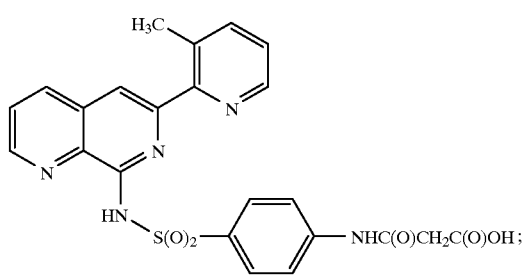

-continued
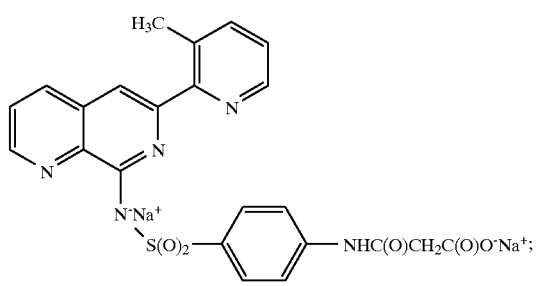
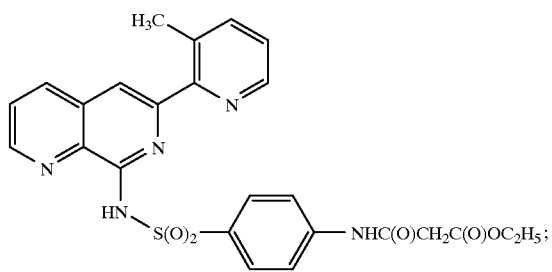
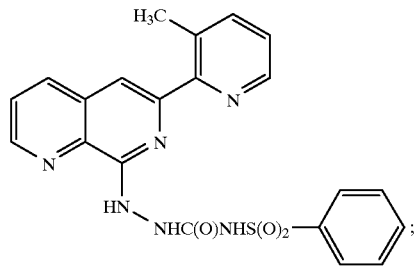
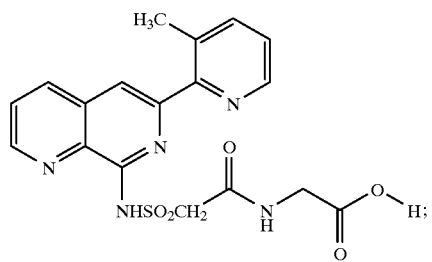
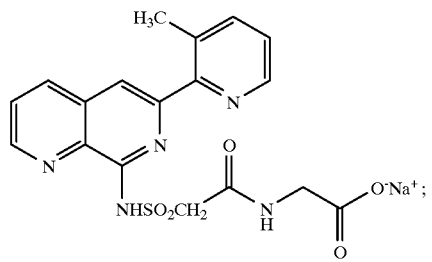
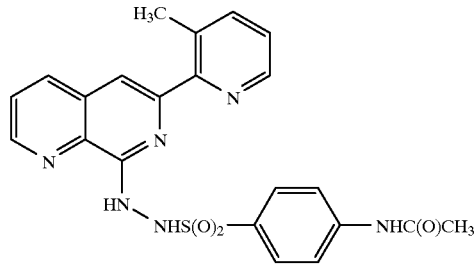

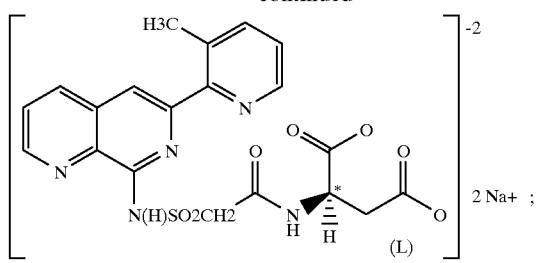
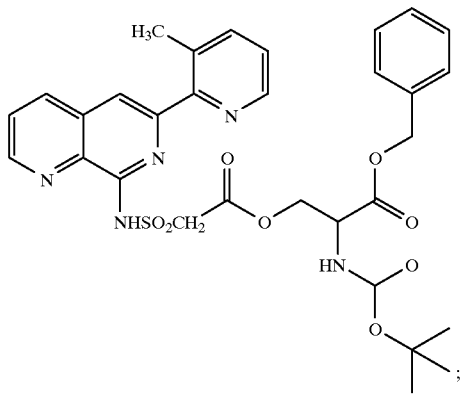
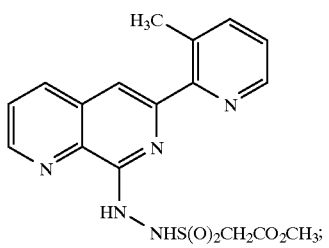
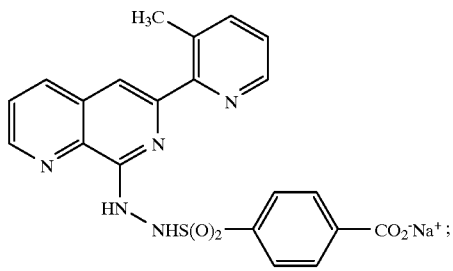
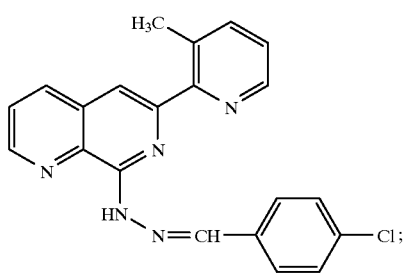
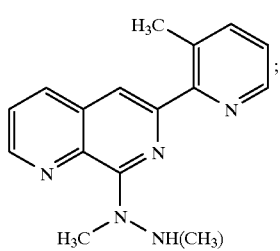

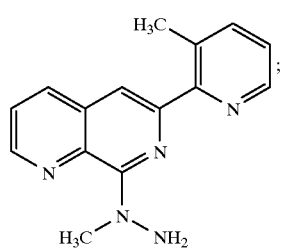
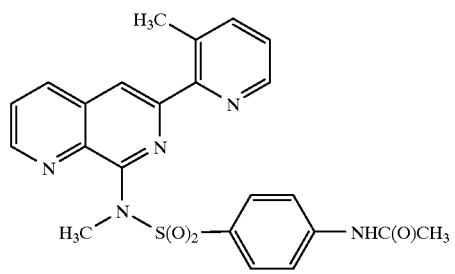
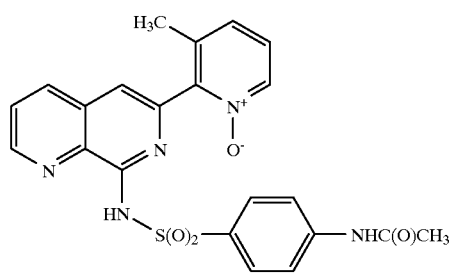
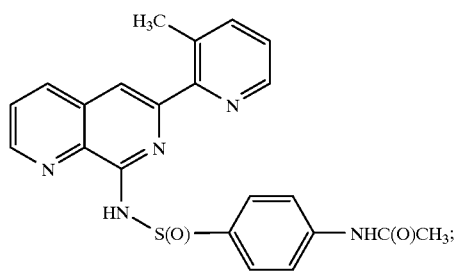
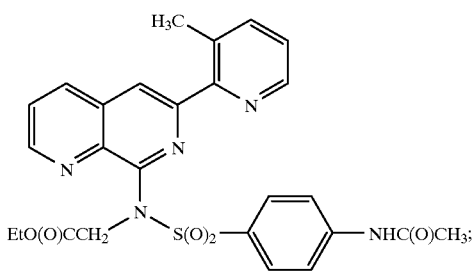
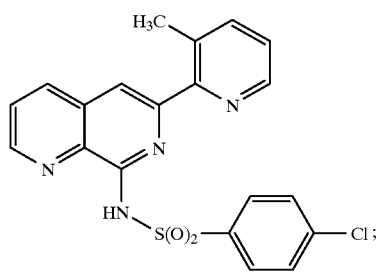

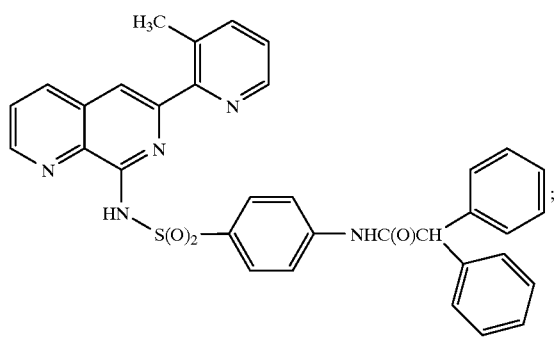
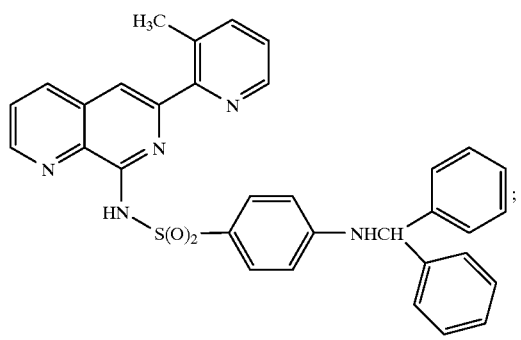
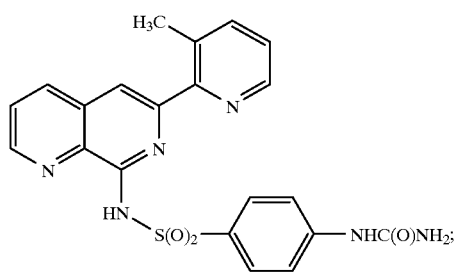
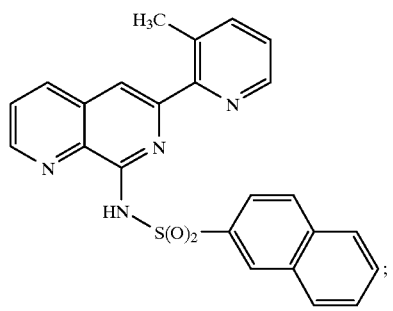
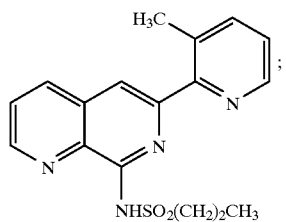

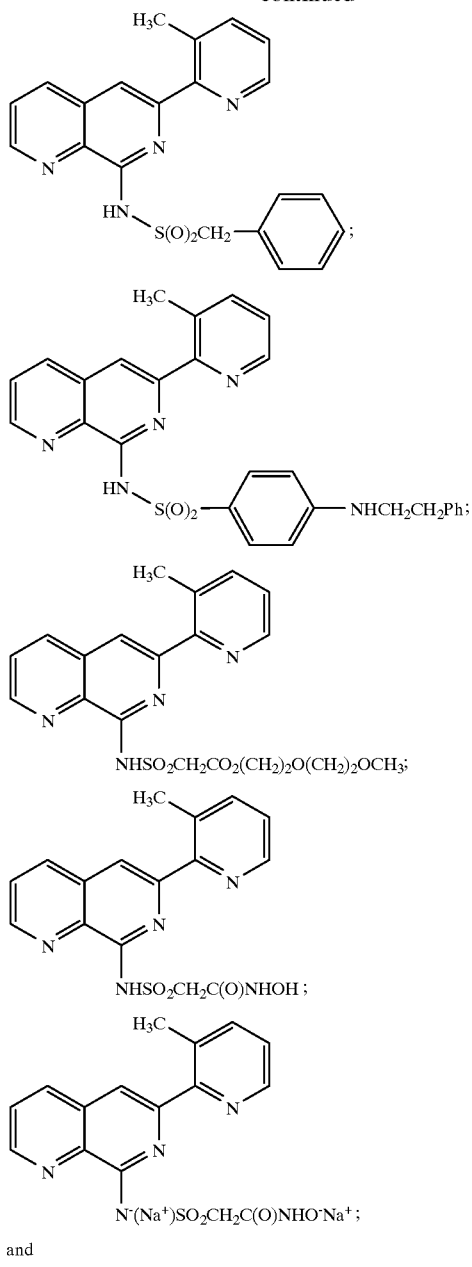
and
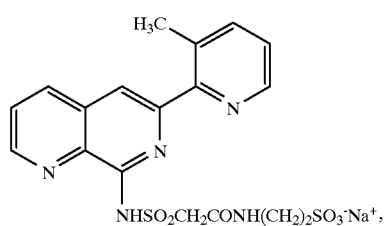
or a pharmaceutically acceptable salt thereof.

12. The compound according to claim 1,

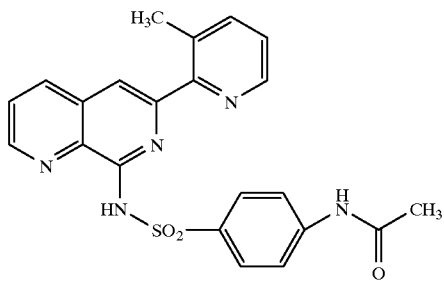

or a pharmaceutically acceptable salt thereof.

13. The compound according to claim 1,

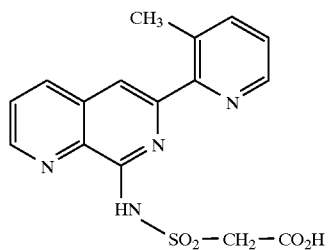

or a pharmaceutically acceptable salt thereof.

14. The compound according to claim 1,

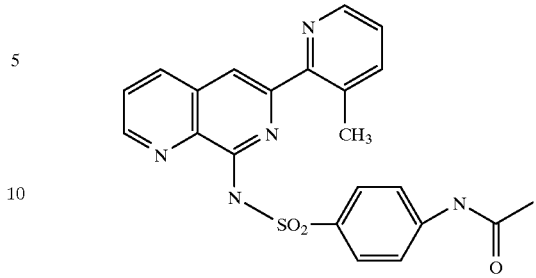

or a pharmaceutically acceptable salt thereof.

15. A pharmaceutical composition comprising a therapeutically effective amount of a compound as defined in claim 1, in combination with a pharmaceutically acceptable carrier.

16. A method for treating allergy, inflammation, autoimmune diseases, B-cell lymphomas, tumors, or the aftereffects of bone marrow transplantation which comprises administering to a mammal in need of such treatment a therapeutically effective amount of a compound according to claim 1.

* * * * *